(12) United States Patent
Singh

(10) Patent No.: US 9,663,570 B2
(45) Date of Patent: May 30, 2017

(54) SINGLE DOMAIN ANTIBODIES DIRECTED AGAINST KRAS

(71) Applicant: SINGH MOLECULAR MEDICINE, LLC, Tampa, FL (US)

(72) Inventor: Sunanda Singh, Lutz, FL (US)

(73) Assignee: Singh Molecular Medicine, LLC, Tampa, FL (US)

( * ) Notice: Subject to any disclaimer, the term of this patent is extended or adjusted under 35 U.S.C. 154(b) by 0 days.

(21) Appl. No.: 14/922,098

(22) Filed: Oct. 23, 2015

(65) Prior Publication Data

US 2016/0115244 A1 Apr. 28, 2016

Related U.S. Application Data

(60) Provisional application No. 62/210,795, filed on Aug. 27, 2015, provisional application No. 62/188,353, filed on Jul. 2, 2015, provisional application No. 62/148,656, filed on Apr. 16, 2015, provisional application No. 62/067,908, filed on Oct. 23, 2014.

(51) Int. Cl.
| | | |
|---|---|---|
| C07K 16/24 | (2006.01) |
| A61K 39/395 | (2006.01) |
| A61K 45/06 | (2006.01) |
| G01N 33/68 | (2006.01) |
| C07K 16/32 | (2006.01) |
| C07K 16/42 | (2006.01) |
| C07K 16/18 | (2006.01) |
| C07K 16/30 | (2006.01) |
| C07K 16/40 | (2006.01) |
| G01N 33/574 | (2006.01) |
| G01N 33/94 | (2006.01) |
| A61K 39/00 | (2006.01) |

(52) U.S. Cl.
CPC ........ *C07K 16/241* (2013.01); *A61K 39/3955* (2013.01); *A61K 39/39558* (2013.01); *A61K 45/06* (2013.01); *C07K 16/18* (2013.01); *C07K 16/303* (2013.01); *C07K 16/3015* (2013.01); *C07K 16/3069* (2013.01); *C07K 16/32* (2013.01); *C07K 16/40* (2013.01); *C07K 16/42* (2013.01); *C07K 16/4241* (2013.01); *G01N 33/574* (2013.01); *G01N 33/686* (2013.01); *G01N 33/6854* (2013.01); *G01N 33/6872* (2013.01); *G01N 33/94* (2013.01); *A61K 2039/505* (2013.01); *C07K 2317/569* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,004,697 A | 4/1991 | Pardridge |
| 7,638,122 B2 | 12/2009 | Yu et al. |
| 8,703,131 B2 | 4/2014 | Beirnaert |
| 8,715,659 B2 | 5/2014 | Muruganandam et al. |
| 9,067,991 B2 | 6/2015 | Beirnaert |
| 2004/0052762 A1 | 3/2004 | Yu et al. |
| 2005/0226863 A1 | 10/2005 | Colby et al. |
| 2005/0255113 A1 | 11/2005 | Huston et al. |
| 2005/0272120 A1 | 12/2005 | Rabbitts et al. |
| 2006/0034845 A1 | 2/2006 | Silence et al. |
| 2007/0077249 A1 | 4/2007 | Silence et al. |
| 2009/0022721 A1 | 1/2009 | Silence et al. |
| 2009/0238829 A1 | 9/2009 | Silence et al. |
| 2010/0021459 A1 | 1/2010 | Silence et al. |
| 2010/0143371 A1 | 6/2010 | Zhu |
| 2011/0027281 A1 | 2/2011 | Silence et al. |
| 2011/0195509 A1 | 8/2011 | Pardoll et al. |
| 2011/0250211 A1 | 10/2011 | Lafaye et al. |
| 2012/0202977 A1 | 8/2012 | Silence et al. |
| 2013/0177979 A1 | 7/2013 | Turkson |
| 2014/0335101 A1 | 11/2014 | Beirnaert |
| 2016/0115226 A1 | 4/2016 | Singh |
| 2016/0115247 A1 | 4/2016 | Singh |
| 2016/0115248 A1 | 4/2016 | Singh |

FOREIGN PATENT DOCUMENTS

| | | |
|---|---|---|
| BE | WO2004/041862 A2 | 5/2004 |
| DE | WO01/78785 A2 | 10/2001 |
| EP | WO2011/051327 A2 | 5/2011 |

(Continued)

OTHER PUBLICATIONS

Tanaka et al. (EMBO, 26:3250-3259, 2007).*
Roth et al. (Journal of Clinical Oncology, 28(3):466-474).*
Tanaka et al. (J. Mol. Biol., 331:1109-1120, 2003).*
Kijanka, M. et al., "Nanobody-based Cancer Therapy of Solid Tumors," Nanomedicine 2015; 10(1):161-174 (26 pages).
Ablynx NV, "Nanobody Advantages," http://www.ablynx.com/en/research-development, Jan. 1, 2013 (2 pages).
Weeks, Don, "Developing Surface Nanobodies Specific to Chlamydomonas Reinhardtii," University of Nebraska-Lincoln, Algal Biomass Summit, Sep. 27, 2012 (32 pages).

(Continued)

*Primary Examiner* — Brad Duffy
*Assistant Examiner* — Nelson B Moseley, II
(74) *Attorney, Agent, or Firm* — Laura M. Lloyd; Leech Tishman Fuscaldo & Lampl

(57) ABSTRACT

This invention provides compositions and methods to treat a condition or disease without the use of exogenous targeting sequences or chemical compositions. The present invention relates to single-domain antibodies (sdAbs), proteins and polypeptides comprising the sdAbs that are directed against intracellular components that cause a condition or disease. The invention also includes nucleic acids encoding the sdAbs, proteins and polypeptides, and compositions comprising the sdAbs. The invention includes the use of the compositions, sdAbs, and nucleic acids encoding the sdAbs for prophylactic, therapeutic or diagnostic purposes.

10 Claims, 14 Drawing Sheets

(56) References Cited

FOREIGN PATENT DOCUMENTS

| WO | 2009004495 A2 | 1/2009 |
|---|---|---|
| WO | WO2011/163423 A2 | 12/2011 |
| WO | 2015031837 A1 | 3/2015 |
| WO | 2015007186 A1 | 5/2015 |
| WO | WO2015071857 A1 | 5/2015 |
| WO | WO2015114538 A1 | 8/2015 |
| WO | 2016065323 A2 | 4/2016 |

OTHER PUBLICATIONS

Bowman, Tammy, et al., "STATs in Oncogenesis," Oncogene vol. 19, 2000 (pp. 2474-2488).

GLG Pharma, LLC, "A Speciality Pharmaceutical Company . . . developing the next generation of targeted drugs," (22 pages).

Jähnichen, Sven, et al., "CXCR4 Nanobodies (VHH-based single variable domains) Potently Inhibit Chemotaxis and HIV-1 Replication and Mobilize Stem Cells," PNAS, vol. 107, No. 47, Nov. 23, 2010 (pp. 20565-20570).

Jove, Richard, "Preface: STAT Signaling," Oncogene vol. 19, 2000 (pp. 2466-2467).

Kirchhofer, Axel, et al., "Modulation of Protein Properties in Living Cells Using Nanobodies," Nature Structural & Molecular Biology, vol. 17, No. 1, Jan. 2010 (19 pages).

Maussang, David, et al., "Molecular Bases of Disease: Llama-derived Single Variable Domains (Nanobodies) Directed Against Chemokine Receptor CXCR7 Reduce Head and Neck Cancer Growth in Vivo," The Journal of Biological Chemistry, vol. 288, No. 41, Oct. 11, 2013 (pp. 29562-29572).

Turkson et al., "A Novel Platinum Compound Inhibits Constitutive Stat3 Signaling and Induces Cell Cycle Arrest and Apoptosis of Malignant Cells," Journal of Biological Chemistry, vol. 280, No. 38, Sep. 23, 2005, pp. 32979-32988 (10 pages).

Van Impe K. et al., Nanobody Lab, "Use of Camelid Nanobodies as Protein Function Inhibitors in Cancer, Inflammation and Amyloid Diseases, Thus Establishing the Therapeutic of Drug Targets," Universiteit Gent, Department of Biochemistry, Oct. 24, 2012 (2 pages).

Nguyen, Viet Khong, et al., "Camel Heavy-Chain Antibodies: Diverse Germline VHH and Specific Mechanisms Enlarge the Antigen-Binding Repertoire," The EMBO Journal, vol. 19, No. 5, (pp. 921-930).

Rothbauer, Ulrich, et al., "Targeting and Tracing Antigens in Live Cells With Fluorescent Nanobodies," Nature Methods, vol. 3, No. 11, Nov. 2006 (pp. 887-889).

Siddiquee, Khandaker A.Z., "An Oxazole-Based Small-Molecule Stat3 Inhibitor Modulates Stat3 Stability and Processing and Induces Antitumor Cell Effects," ACS Chemical Biology, vol. 2, No. 12 (pp. 787-798).

Siddiquee, Khandaker, "Selective Chemical Probe Inhibitor of Stat3, Identified Through Structure-Based Virtual Screening, Induces Antitumor Activity," PNAS, vol. 104, No. 18, May 1, 2007 (pp. 7391-7396).

Wiecek, Andrew S., "Nanobodies: Going Single-domain," BioTechniques, The International Journal of Life Science Methods, May 4, 2010, (3 pages).

Wolfson, Wendy, "Ablynx Makes Nanobodies from Llama Bodies," Innovations, Chemistry & Biology, vol. 13, Dec. 2006 (pp. 1243-1244).

Li, T. et al., "Cell-penetrating anti-GFAP VHH and corresponding fluorescent fusion protein VHH-GFP spontaneously cross the blood-brain barrier and specifically recognize astrocytes: application to brain imaging." The FASEB Journal, www.fasebj.org., vol. 26, Oct. 2012, pp. 1-11.

Wesolowski, J. et al., "Single domain antibodies: promising experimental and therapeutic tools in infection and immunity," Med. Microbiol. Immunol. (2009) 198:157-174.

Abulrob, A., et al., "The blood-brain barrier transmigrating single domain antibody: mechanisms of transport and antigenic epitopes in human brain endothelial cells," J. Neurochem. (2005) 95, 1201-1214.

USPTO, Non-Final Office Action on the Merits issued in related U.S. Appl. No. 14/922,100 on Jun. 17, 2016 (18 pages).

Gueorguieva, D., et al., "Identification of single-domain, Bax-specific intrabodies that confer resistance to mammalian cells against oxidative-stress-induced apoptosis," The FASEB Journal, 2006, vol. 20, pp. E2209-E2219.

Nguyen, Viet Khong, et al., "Camel Heavy-Chain Antibodies: Diverse Germline VHH and Specific Mechanisms Enlarge the Antigen-Binding Repertoire," The EMBO Journal, vol. 19, No. 5, 2000, (pp. 921-930).

Siddiquee, Khandaker A.Z., "An Oxazole-Based Small-Molecule Stat3 Inhibitor Modulates Stat3 Stability and Processing and Induces Antitumor Cell Effects," ACS Chemical Biology, vol. 2, No. 12, Dec. 21, 2007 (pp. 787-798).

Sommer et al., Constitutively Active Mutant gp130 Receptor Protein from Inflammatory Hepatocellular Adenoma Is Inhibited by an Anti-gp130 Antibody That Specifically Neutralizes Interleukin 11 Signaling, J. Biol. Chem., Apr. 20, 2012, vol. 287, No. 17, pp. 13743-13751.

USPTO, Restriction Requirement and Non-Final Office Action on the Merits issued in related U.S. Appl. No. 14/922,081 on Feb. 25, 2016 (26 pages).

USPTO, Non-Final Office Action on the Merits issued in related U.S. Appl. No. 14/922,100 on Apr. 18, 2016 (18 pages).

USPTO, International Search Report (ISR) and Written Opinion issued by the International Searching Authority/US in related International Patent Application No. PCT/US2015/57223 on Apr. 22, 2016.

USPTO, Non-Final Office Action on the Merits issued in related U.S. Appl. No. 14/922,093 on Jun. 27, 2016 (25 pages).

USPTO, International Preliminary Report on Patentability (IPRP) issued by the International Searching Authority/US in related International Patent Application No. PCT/US2015/57223 on Aug. 12, 2016.

USPTO, Final Office Action on the Merits issued in related U.S. Appl. No. 14/922,081 on Sep. 6, 2016 (16 pages).

\* cited by examiner

Lanes:
M- Marker
1- STAT3 VHH13 (mammalian)
2- STAT3 VHH14 (mammalian)
3- STAT3 VHH13 (bacterial)
4- STAT3- VHH14 (bacterial)
5- Positive control (STAT-3)
6- Negative control (STAT-1)

Lanes:
M= Marker
1= PANC-1 with anti-STAT3 B VHH13
2= DU145 with anti-STAT3 B VHH13
3= HeLa + IFN-gamma with anti-STAT3 B VHH13
4= 4T1 with anti-STAT3 B VHH13
5= PANC-1 with anti-KRAS (G12D) VHH
6= PC-3 (negative control) with anti-STAT3 B VHH13

Top curve: G1 is control group with vehicle only IP; given twice daily
Second curve: G2 is given anti-STAT3 B VHH13 IP; 1mg/kg/twice daily
Third curve at the beginning: G3 is given anti-STAT3 B VHH13 IP; 2mg/kg/twice daily
Bottom curve at the beginning: G4 is given anti-STAT3 B VHH13 2mg/kg/once daily

SEQUENCE LISTING

<160> NUMBER OF SEQ ID NOS: 81

<210> SEQ ID NO 1
<211> LENGTH: 372
<212> TYPE: DNA
<213> ORGANISM: Artificial Sequence
<220> FEATURE:
<223> OTHER INFORMATION: Camelid

<400> SEQUENCE: 1

```
gaggtgcagc tggtggagtc tgggggaggc tcggtgcaga ctggagggtc tctgagactc      60
tcctgtgcag tttctggaaa tatcggcagc agctactgca tgggctggtt ccgccaggct     120
ccagggaaga gcgcgaggc ggtcgcacgt attgtacgtg atggtgccac tggctacgca      180
gactacgtga agggccgatt caccatctcc cgagacagcg ccaagaacac tctgtatctg     240
caaatgaaca ggctgatacc tgaggacact gccatctact actgtgcggc agacctgccc     300
ccaggttgtt tgactcaggc gatttggaat tttggttatc ggggccaggg aaccctggtc     360
accgtctcct ca                                                         372
```

<210> SEQ ID NO 2
<211> LENGTH: 124
<212> TYPE: PRT
<213> ORGANISM: Artificial Sequence
<220> FEATURE:
<223> OTHER INFORMATION: Camelid

<400> SEQUENCE: 2

Glu Val Gln Leu Val Glu Ser Gly Gly Gly Ser Val Gln Thr Gly Gly
1               5                   10                  15

Ser Leu Arg Leu Ser Cys Ala Val Ser Gly Asn Ile Gly Ser Ser Tyr
            20                  25                  30

Cys Met Gly Trp Phe Arg Gln Ala Pro Gly Lys Lys Arg Glu Ala Val
        35                  40                  45

Ala Arg Ile Val Arg Asp Gly Ala Thr Gly Tyr Ala Asp Tyr Val Lys
    50                  55                  60

Gly Arg Phe Thr Ile Ser Arg Asp Ser Ala Lys Asn Thr Leu Tyr Leu
65                  70                  75                  80

Gln Met Asn Arg Leu Ile Pro Glu Asp Thr Ala Ile Tyr Tyr Cys Ala
                85                  90                  95

Ala Asp Leu Pro Pro Gly Cys Leu Thr Gln Ala Ile Trp Asn Phe Gly
            100                 105                 110

Tyr Arg Gly Gln Gly Thr Leu Val Thr Val Ser Ser
        115                 120

<210> SEQ ID NO 3
<211> LENGTH: 127
<212> TYPE: PRT
<213> ORGANISM: Artificial Sequence
<220> FEATURE:
<223> OTHER INFORMATION: Camelid

<400> SEQUENCE: 3

His Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
            50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                    85                  90                  95

Ala Thr Ser Arg Phe Asp Cys Tyr Arg Gly Ser Trp Phe Asn Arg Tyr
                100                 105                 110

Met Tyr Asn Ser Trp Gly Gln Gly Thr Gln Val Thr Val Ser Ser
                115                 120                 125

<210> SEQ ID NO 4
<211> LENGTH: 126
<212> TYPE: PRT
<213> ORGANISM: Artificial Sequence
<220> FEATURE:
<223> OTHER INFORMATION: Camelid

<400> SEQUENCE: 4

Gln Val Gln Leu Val Glu Ser Gly Gly Gly Ser Val Gln Ala Gly Gly
 1               5                  10                  15

Ser Leu Arg Leu Ser Cys Val Ala Ser Thr Tyr Thr Gly Cys Met Gly
                20                  25                  30

Trp Phe Arg Gln Ala Pro Gly Lys Glu Arg Glu Gly Val Ala Ala Leu
                35                  40                  45

Ser Ser Arg Gly Phe Ala Gly His Tyr Thr Asp Ser Val Lys Gly Arg
            50                  55                  60

Phe Ser Ile Ser Arg Asp Tyr Val Lys Asn Ala Val Tyr Leu Gln Met
 65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
                100                 105                 110

His Thr Tyr Trp Gly Gln Gly Thr Leu Val Thr Val Ser Ser
                115                 120                 125

<210> SEQ ID NO 5
<211> LENGTH: 126
<212> TYPE: PRT
<213> ORGANISM: Artificial Sequence
<220> FEATURE:
<223> OTHER INFORMATION: Camelid

<400> SEQUENCE: 5

Asp Val Gln Leu Val Glu Ser Gly Gly Gly Ser Val Gln Ala Gly Gly
 1               5                  10                  15

Ser Leu Arg Leu Ser Cys Val Ala Ser Thr Tyr Thr Gly Cys Met Gly
                20                  25                  30

Trp Phe Arg Gln Ala Pro Gly Lys Glu Arg Glu Gly Val Ala Ala Leu
                35                  40                  45

Ser Ser Arg Gly Phe Ala Gly His Tyr Thr Asp Ser Val Lys Gly Arg
            50                  55                  60

Phe Ser Ile Ser Arg Asp Tyr Val Lys Asn Ala Val Tyr Leu Gln Met
 65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
                100                 105                 110

His Thr Tyr Trp Gly Gln Gly Thr Gln Val Thr Val Ser Ser
        115                 120                 125

<210> SEQ ID NO 6
<211> LENGTH: 126
<212> TYPE: PRT
<213> ORGANISM: Artificial Sequence
<220> FEATURE:
<223> OTHER INFORMATION: Camelid

<400> SEQUENCE: 6

Asp Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Trp Leu Asp Arg Thr Ala Gly Gly
            100                 105                 110

His Thr Tyr Trp Gly Gln Gly Thr Gln Val Thr Val Ser Ser
        115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Camelid

<400> SEQUENCE: 7

His Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Trp Leu Asp Arg Thr Ala Gly Gly
            100                 105                 110

His Thr Tyr Trp Gly Gln Gly Thr Gln Val Thr Val Ser Ser
        115                 120                 125

<210> SEQ ID NO 8
<211> LENGTH: 126
<212> TYPE: PRT
<213> ORGANISM: Artificial Sequence
<220> FEATURE:
<223> OTHER INFORMATION: Camelid

<400> SEQUENCE: 8

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125
```

<210> SEQ ID NO 9
<211> LENGTH: 126
<212> TYPE: PRT
<213> ORGANISM: Artificial Sequence
<220> FEATURE:
<223> OTHER INFORMATION: Camelid

<400> SEQUENCE: 9

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125
```

<210> SEQ ID NO 10
<211> LENGTH: 126
<212> TYPE: PRT
<213> ORGANISM: Artificial Sequence
<220> FEATURE:
<223> OTHER INFORMATION: Camelid

<400> SEQUENCE: 10

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45
```

Ser Ser Arg Gly Phe Ala Gly His Tyr Thr Asp Ser Val Lys Gly Arg
            50                  55                  60

Phe Ser Ile Ser Arg Asp Tyr Val Lys Asn Ala Val Tyr Leu Gln Met
 65                  70                  75                  80

Asn Thr Val Lys Pro Glu Asp Ala Ala Met Tyr Tyr Cys Ala Ala Arg
                 85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
            115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Camelid

<400> SEQUENCE: 11

Gln Val Gln Leu Val Glu Ser Gly Gly Gly Ser Val Gln Ala Gly Gly
 1               5                  10                  15

Ser Leu Arg Leu Ser Cys Val Ala Ser Thr Tyr Thr Gly Cys Met Gly
             20                  25                  30

Trp Phe Arg Gln Ala Pro Gly Lys Glu Arg Glu Gly Val Ala Ala Leu
         35                  40                  45

Ser Ser Arg Gly Phe Ala Gly His Tyr Thr Asp Ser Val Lys Gly Arg
     50                  55                  60

Phe Ser Ile Ser Arg Asp Tyr Val Lys Asn Ala Val Tyr Leu Gln Met
 65                  70                  75                  80

Asn Thr Val Lys Pro Glu Asp Ala Ala Met Tyr Tyr Cys Ala Ala Arg
                 85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
            115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Camelid

<400> SEQUENCE: 12

Gln Val Gln Leu Val Glu Ser Gly Gly Gly Ser Val Gln Ala Gly Gly
 1               5                  10                  15

Ser Leu Arg Leu Ser Cys Val Ala Ser Thr Tyr Thr Gly Cys Met Gly
             20                  25                  30

Trp Phe Arg Gln Ala Pro Gly Lys Glu Arg Glu Gly Val Ala Ala Leu
         35                  40                  45

Ser Ser Arg Gly Phe Ala Gly His Tyr Thr Asp Ser Val Lys Gly Arg
     50                  55                  60

Phe Ser Ile Ser Arg Asp Tyr Val Lys Asn Ala Val Tyr Leu Gln Met
 65                  70                  75                  80

Asn Thr Val Lys Pro Glu Asp Ala Ala Met Tyr Tyr Cys Ala Ala Arg
                 85                  90                  95

Glu Gly Trp Glu Cys Gly Glu Thr Trp Leu Asp Arg Thr Ala Gly Ser

His Thr Tyr Trp Gly Gln Gly Thr Leu Val Thr Val Ser Ser
        115                 120                 125

<210> SEQ ID NO 13
<211> LENGTH: 126
<212> TYPE: PRT
<213> ORGANISM: Artificial Sequence
<220> FEATURE:
<223> OTHER INFORMATION: Camelid

<400> SEQUENCE: 13

Glu Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125

<210> SEQ ID NO 14
<211> LENGTH: 126
<212> TYPE: PRT
<213> ORGANISM: Artificial Sequence
<220> FEATURE:
<223> OTHER INFORMATION: Camelid

<400> SEQUENCE: 14

Asp Val Gln Leu Val Glu Ser Gly Gly Gly Ser Val Gln Ala Gly Asp
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125

<210> SEQ ID NO 15
<211> LENGTH: 127
<212> TYPE: PRT
<213> ORGANISM: Artificial Sequence
<220> FEATURE:

<223> OTHER INFORMATION: Camelid

<400> SEQUENCE: 15

Gln Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 16
<211> LENGTH: 127
<212> TYPE: PRT
<213> ORGANISM: Artificial Sequence
<220> FEATURE:
<223> OTHER INFORMATION: Camelid

<400> SEQUENCE: 16

Gln Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Thr Asn Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 17
<211> LENGTH: 127
<212> TYPE: PRT
<213> ORGANISM: Artificial Sequence
<220> FEATURE:
<223> OTHER INFORMATION: Camelid

<400> SEQUENCE: 17

Glu Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val

```
            35                  40                  45
Ser Gly Ile Ser Thr Gly Gly Leu Ile Thr Tyr Tyr Ala Asp Ser Val
 50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
            115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Camelid

<400> SEQUENCE: 18

Asp Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
             20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
 50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
            115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Camelid

<400> SEQUENCE: 19

Asp Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
             20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
 50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95
```

```
Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Camelid

<400> SEQUENCE: 20

Asp Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 21
<211> LENGTH: 127
<212> TYPE: PRT
<213> ORGANISM: Artificial Sequence
<220> FEATURE:
<223> OTHER INFORMATION: Camelid

<400> SEQUENCE: 21

His Val Gln Leu Val Glu Ser Glu Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 22
<211> LENGTH: 127
<212> TYPE: PRT
<213> ORGANISM: Artificial Sequence
```

<220> FEATURE:
<223> OTHER INFORMATION: Camelid

<400> SEQUENCE: 22

Gln Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Camelid

<400> SEQUENCE: 23

Gln Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125

<210> SEQ ID NO 24
<211> LENGTH: 127
<212> TYPE: PRT
<213> ORGANISM: Artificial Sequence
<220> FEATURE:
<223> OTHER INFORMATION: Camelid

<400> SEQUENCE: 24

Glu Val Gln Leu Val Glu Ser Gly Gly Gly Ser Val Gln Ala Gly Gly
1               5                   10                  15

Ser Leu Arg Leu Ser Cys Ala Ser Gly Ala Asn Gly Gly Arg Ser
            20                  25                  30

```
Cys Met Gly Trp Phe Arg Gln Val Pro Gly Lys Glu Arg Glu Gly Val
         35                  40                  45

Ser Gly Ile Ser Thr Gly Gly Leu Ile Thr Tyr Tyr Ala Asp Ser Val
 50                  55                  60

Lys Gly Arg Phe Thr Ile Ser Gln Asp Asn Thr Lys Asn Thr Leu Tyr
 65                  70                  75                  80

Leu Gln Met Ser Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
                100                 105                 110

Met Tyr Asn Ser Trp Gly Gln Gly Thr Gln Val Thr Val Ser Ser
         115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Camelid

<400> SEQUENCE: 25

Asp Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
             20                  25                  30

Cys Met Gly Trp Phe Arg Gln Val Pro Gly Lys Glu Arg Glu Gly Val
         35                  40                  45

Ser Gly Ile Ser Thr Gly Gly Leu Ile Thr Tyr Tyr Ala Asp Ser Val
 50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
                100                 105                 110

Met Tyr Asn Ser Trp Gly Gln Gly Thr Gln Val Thr Val Ser Ser
         115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Camelid

<400> SEQUENCE: 26

His Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
             20                  25                  30

Cys Met Gly Trp Phe Arg Gln Val Pro Gly Lys Glu Arg Glu Gly Val
         35                  40                  45

Ser Gly Ile Ser Thr Gly Gly Leu Ile Thr Tyr Tyr Ala Asp Ser Val
 50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95
```

```
Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Camelid

<400> SEQUENCE: 27

His Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125

<210> SEQ ID NO 28
<211> LENGTH: 127
<212> TYPE: PRT
<213> ORGANISM: Artificial Sequence
<220> FEATURE:
<223> OTHER INFORMATION: Camelid

<400> SEQUENCE: 28

His Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125

<210> SEQ ID NO 29
<211> LENGTH: 127
<212> TYPE: PRT
```

<213> ORGANISM: Artificial Sequence
<220> FEATURE:
<223> OTHER INFORMATION: Camelid

<400> SEQUENCE: 29

```
His Val Gln Leu Val Glu Ser Gly Gly Ser Val Gln Ala Gly Gly
 1               5                  10                  15
Ser Leu Arg Leu Ser Cys Ala Ala Ser Gly Ala Asn Gly Gly Arg Ser
            20                  25                  30
Cys Met Gly Trp Phe Arg Gln Val Pro Gly Lys Glu Arg Glu Gly Val
        35                  40                  45
Ser Gly Ile Ser Thr Gly Gly Leu Ile Thr Tyr Tyr Ala Asp Ser Val
    50                  55                  60
Lys Gly Arg Phe Thr Ile Ser Gln Asp Asn Thr Lys Asn Thr Leu Tyr
65                  70                  75                  80
Leu Gln Met Asn Ser Leu Lys Pro Glu Asp Thr Ala Met Tyr Tyr Cys
                85                  90                  95
Ala Thr Ser Arg Phe Asp Cys Tyr Arg Gly Ser Trp Phe Asn Arg Tyr
            100                 105                 110
Met Tyr Asn Ser Trp Gly Gln Gly Thr Gln Val Thr Val Ser Ser
        115                 120                 125
```

<210> SEQ ID NO 30
<211> LENGTH: 378
<212> TYPE: DNA
<213> ORGANISM: Artificial Sequence
<220> FEATURE:
<223> OTHER INFORMATION: Camelid

<400> SEQUENCE: 30

```
gatgtgcagc tggtggagtc tgggggaggc tcggtgcagg ctggaggctc tctgagactc      60
tcctgtgtag cctctacata caccggctgc atgggctggt tccgccaggc tcctggaaag    120
gagcgcgagg gagtcgcagc tcttagtagc cgtggttttg ccgggcacta taccgactcc    180
gtgaagggcc gattctccat ctcccgagac tacgtcaaga atgcggtgta tctgcaaatg    240
aacactgtga aacctgagga cgctgccatg tactactgtg cagcacggga gggatgggag    300
tgcggtgaga cctggttgga ccggaccgcc gggggccata cctactgggg ccaggggacc    360
caggtcaccg tctcctca                                                  378
```

<210> SEQ ID NO 31
<211> LENGTH: 378
<212> TYPE: DNA
<213> ORGANISM: Artificial Sequence
<220> FEATURE:
<223> OTHER INFORMATION: Camelid

<400> SEQUENCE: 31

```
caggtgcagc tggtggagtc tgggggaggc tcggtgcagg ctggaggctc tctgagactc      60
tcctgtgtag cctctacata caccggctgc atgggctggt tccgccaggc tcctggaaag    120
gagcgcgagg gagtcgcagc tcttagtagc cgtggttttg ccgggcacta taccgactcc    180
gtgaagggcc gattctccat ctcccgagac tacgtcaaga atgcggtgta tctgcaaatg    240
aacactgtga aacctgagga cgctgccatg tactactgtg cagcacggga gggatgggag    300
tgcggtgaga cctggttgga ccggaccgcc gggggccata cctactgggg ccaggggacc    360
ctggtcaccg tctcctca                                                  378
```

```
<210> SEQ ID NO 32
<211> LENGTH: 381
<212> TYPE: DNA
<213> ORGANISM: Artificial Sequence
<220> FEATURE:
<223> OTHER INFORMATION: Camelid

<400> SEQUENCE: 32
caggtgcagc tggtggagtc tgggggaggc tcggtgcagg ctggagggtc tctgagactc      60
tcctgtgcag cctctggagc caatggtggt cggagctgca tgggctggtt ccgccaggtt     120
ccagggaagg agcgcgaggg ggtttctggt atttcaaccg gtggtcttat tacatactat     180
gccgactccg tgaagggccg attcaccatc tcccaagaca acaccaagaa cacgctgtat     240
ctgcaaatga acagcctgaa acctgaggac actgccatgt actactgtgc gacgagtcgg     300
tttgactgct atagaggctc ttggttcaac cgatatatgt ataacagttg gggccagggg     360
accctggtca ccgtctcctc a                                               381

<210> SEQ ID NO 33
<211> LENGTH: 381
<212> TYPE: DNA
<213> ORGANISM: Artificial Sequence
<220> FEATURE:
<223> OTHER INFORMATION: Camelid

<400> SEQUENCE: 33
catgtgcagc tggtggagtc tgggggaggc tcggtgcagg ctggagggtc tctgagactc      60
tcctgtgcag cctctggagc caacggtggt cggagctgca tgggctggtt ccgccaggtt     120
ccagggaagg agcgcgaggg ggtttctggt atttcaaccg gtggtcttat tacatactat     180
gccgactccg tgaagggccg attcaccatc tcccaagaca acaccaagaa cacgctgtat     240
ctgcaaatga acagcctgaa acctgaggac actgccatgt actactgtgc gacgagtcgg     300
tttgactgct atagaggctc ttggttcaac cgatatatgt ataacagttg gggccagggg     360
acccaggtca ctgtctcctc a                                               381

<210> SEQ ID NO 34
<211> LENGTH: 381
<212> TYPE: DNA
<213> ORGANISM: Artificial Sequence
<220> FEATURE:
<223> OTHER INFORMATION: Camelid

<400> SEQUENCE: 34
gatgtgcagc tggtggagtc tgggggaggc tcggtgcagg ctggagggtc tctgagactc      60
tcctgtgcag cctctggagc caatggtggt cggagctgca tgggctggtt ccgccaggtt     120
ccagggaagg agcgcgaggg ggtttctggt atttcaaccg gtggtcttat tacatactat     180
gccgactccg tgaagggccg attcaccatc tcccaagaca acaccaagaa cacgctgtat     240
ctgcaaatga acagcctgaa acctgaggac actgccatgt actactgtgc gacgagtcgg     300
tttgactgct atagaggctc ttggttcaac cgatatatgt ataacagttg gggccagggg     360
accctggtca ccgtctcctc a                                               381

<210> SEQ ID NO 35
<211> LENGTH: 378
<212> TYPE: DNA
<213> ORGANISM: Artificial Sequence
<220> FEATURE:
<223> OTHER INFORMATION: Camelid
```

```
<400> SEQUENCE: 35
caggtgcagc tggtggagtc tgggggaggc tcggtgcagg ctggaggctc tctgagactc      60
tcctgtgtag cctctacata caccggctgc atgggctggt tccgccaggc tcctggaaag     120
gagcgcgagg gagtcgcagc tcttagcagc cgtggttttg ccgggcacta taccgactcc     180
gtgaagggcc gattctccat ctcccgagac tacgtcaaga atgcggtgta tctgcaaatg     240
aacactgtga aacctgagga cgctgccatg tactactgtg cagcacggga gggatgggag     300
tgcggtgaga cctggttgga ccggaccgcc gggagccata cctactgggg ccaggggacc     360
ctggtcaccg tctcctca                                                   378

<210> SEQ ID NO 36
<211> LENGTH: 378
<212> TYPE: DNA
<213> ORGANISM: Artificial Sequence
<220> FEATURE:
<223> OTHER INFORMATION: Camelid

<400> SEQUENCE: 36
gaggtgcagc tggtggagtc tgggggaggc tcggtgcagg ctggaggctc tctgagactc      60
tcctgtgtag cctctacata caccggctgc atgggctggt tccgccaggc tcctggaaag     120
gagcgcgagg gagtcgcagc tcttagtagc cgtggttttg ccgggcacta taccgactcc     180
gtgaagggcc gattctccat ctcccgagac tacgtcaaga atgcggtgta tctgcaaatg     240
aacactgtga aacctgagga cgctgccatg tactactgtg cagcacggga gggatgggag     300
tgcggtgaga cctggttgga ccgaaccgcc ggggccata cctactgggg ccaggggacc      360
ctggtcaccg tctcctca                                                   378

<210> SEQ ID NO 37
<211> LENGTH: 381
<212> TYPE: DNA
<213> ORGANISM: Artificial Sequence
<220> FEATURE:
<223> OTHER INFORMATION: Camelid

<400> SEQUENCE: 37
gaggtgcagc tggtggagtc tgggggaggc tcggtgcagg ctggagggtc tctgagactc      60
tcctgtgcag cctctggagc caatggtggt cggagctgca tgggctggtt ccgccaggtt     120
ccagggaagg agcgcgaggg ggtttctggt atttcaaccg gtggtcttat tacatactat     180
gccgactccg tgaagggtcg attcaccatc tcccaagaca acaccaagaa cacgctgtat     240
ctgcaaatga gcagcctgaa acctgaggac actgccatgt actactgtgc gacgagtcgg     300
tttgactgct atagaggctc ttggttcaac cgatatatgt ataacagttg gggccagggg     360
acccaggtca ccgtctcctc a                                               381

<210> SEQ ID NO 38
<211> LENGTH: 378
<212> TYPE: DNA
<213> ORGANISM: Artificial Sequence
<220> FEATURE:
<223> OTHER INFORMATION: Camelid

<400> SEQUENCE: 38
catgtgcagc tggtggagtc tggggggggc tcggtgcagg ctggaggctc tctgagactc      60
tcctgtgtag cctctacata caccggctgc atgggctggt tccgccaggc tcctggaaag     120
gagcgcgagg gagtcgcagc tcttagtagc cgtggttttg ccgggcacta taccgactcc     180
```

| | |
|---|---|
| gtgaagggcc gattctccat ctcccgagac tacgtcaaga atgcggtgta tctgcaaatg | 240 |
| aacactgtga aacctgagga cgctgccatg tactactgtg cagcacggga gggatgggag | 300 |
| tgcggtgaga cctggttgga ccggaccgcc gggggccata cctactgggg ccaggggacc | 360 |
| caggtcaccg tctcctca | 378 |

<210> SEQ ID NO 39
<211> LENGTH: 381
<212> TYPE: DNA
<213> ORGANISM: Artificial Sequence
<220> FEATURE:
<223> OTHER INFORMATION: Camelid

<400> SEQUENCE: 39

| | |
|---|---|
| gatgtgcagc tggtggagtc tgggggaggc tcggtgcagg ctggagggtc tctgagactc | 60 |
| tcctgtgcag cctctggagc caatggtggt cggagctgca tgggctggtt ccgccaggtt | 120 |
| ccagggaagg agcgcgaggg ggtttctggt atttcaaccg gtggtcttat tacatactat | 180 |
| gccgactccg tgaagggccg attcaccatc tcccaagaca acaccaagaa cacgctgtat | 240 |
| ctgcaaatga acagcctgaa acctgaggac actgccatgt actactgtgc gacgagtcgg | 300 |
| tttgactgct atagaggctc ttggttcaac cgatatatgt ataacagttg gggccagggg | 360 |
| acccaggtca ccgtctcctc a | 381 |

<210> SEQ ID NO 40
<211> LENGTH: 381
<212> TYPE: DNA
<213> ORGANISM: Artificial Sequence
<220> FEATURE:
<223> OTHER INFORMATION: Camelid

<400> SEQUENCE: 40

| | |
|---|---|
| caggtgcagc tggtggagtc tgggggaggc tcggtgcagg ctggagggtc tctgagactc | 60 |
| tcctgtgcag cctctggagc caatggtggt cggagctgca tgggctggtt ccgccaggtt | 120 |
| ccagggaagg agcgcgaggg ggtttctggt atttcaaccg gtggtcttat tacatactat | 180 |
| gccgactccg tgaagggccg attcaccatc tcccaagaca acaccaagaa cacgctgtat | 240 |
| ctgcaaatga acagcctgaa acctgaggac actgccatgt actactgtgc gacgagtcgg | 300 |
| tttgactgct atagaggctc ttggttcaac cgatatatgt ataacagttg gggccagggg | 360 |
| acccaggtca ccgtctcctc a | 381 |

<210> SEQ ID NO 41
<211> LENGTH: 378
<212> TYPE: DNA
<213> ORGANISM: Artificial Sequence
<220> FEATURE:
<223> OTHER INFORMATION: Camelid

<400> SEQUENCE: 41

| | |
|---|---|
| gatgtgcagc tggtggagtc tgggggaggc tcggtgcagg ctggagactc tctgagactc | 60 |
| tcctgtgtag cctctacata caccggctgc atgggctggt ccgccaggc tcctggaaag | 120 |
| gagcgcgagg gagtcgcagc tcttagtagc cgtggttttg ccgggcacta taccgactcc | 180 |
| gtgaagggcc gattctccat ctcccgagac tacgtcaaga atgcggtgta tctgcaaatg | 240 |
| aacactgtga aacctgagga cgctgccatg tactactgtg cagcacggga gggatgggag | 300 |
| tgcggtgaga cctggttgga ccggaccgcc gggggccata cctactgggg ccaggggacc | 360 |

```
ctggtcactg tctcctca                                              378
```

<210> SEQ ID NO 42
<211> LENGTH: 378
<212> TYPE: DNA
<213> ORGANISM: Artificial Sequence
<220> FEATURE:
<223> OTHER INFORMATION: Camelid

<400> SEQUENCE: 42

```
gtgcagctgg tggagtctgg gggaggctcg gtgcaggctg agggtctct gagactctcc    60
tgtgcagcct ctggagccaa tggtggtcgg agctgcatgg gctggttccg ccaggttcca   120
gggaaggagc gtgaggggggt ttctggtatt tcaaccggtg gtcttattac atactatgcc  180
gactccgtga agggccgatt caccatctcc aagacaaca ccaagaacac gctgtatctg    240
caaatgaaca gcctgaaacc tgaggacact gccatgtact actgtgcgac gagtcggttt   300
gactgctata gaggctcttg gttcaaccga tatatgtata acagttgggg ccaggggacc   360
ctggtcactg tctcctca                                                 378
```

<210> SEQ ID NO 43
<211> LENGTH: 378
<212> TYPE: DNA
<213> ORGANISM: Artificial Sequence
<220> FEATURE:
<223> OTHER INFORMATION: Camelid

<400> SEQUENCE: 43

```
gtgcagctgg tggagtctga gggaggctcg gtgcaggctg agggtctct gagactctcc    60
tgtgcagcct ctggagccaa tggtggtcgg agctgcatgg gctggttccg ccaggttcca   120
gggaaggagc gcgaggggt ttctggtatt tcaaccggtg gtcttattac atactatgcc    180
gactccgtga agggccgatt caccatctcc aagacaaca ccaagaacac gctgtatctg    240
caaatgaaca gcctgaaacc tgaggacact gccatgtact actgtgcgac gagtcggttt   300
gactgctata gaggctcttg gttcaaccga tatatgtata acagttgggg ccaggggacc   360
ctggtcaccg tctcctca                                                 378
```

<210> SEQ ID NO 44
<211> LENGTH: 378
<212> TYPE: DNA
<213> ORGANISM: Artificial Sequence
<220> FEATURE:
<223> OTHER INFORMATION: Camelid

<400> SEQUENCE: 44

```
gtgcagctgg tggagtctgg gggaggctcg gtgcaggctg agggtctct gagactctcc    60
tgtgcagcct ctggagccaa tggtggtcgg agctgcatgg gctggttccg ccaggttcca   120
gggaaggagc gcgaggggt ttctggtatt tcaaccggtg gtcttattac atactatgcc    180
gactccgtga agggccgatt caccatctcc aagacaaca ccaataacac gctgtatctg    240
caaatgaaca gcctgaaacc tgaggacact gccatgtact actgtgcgac gagtcggttt   300
gactgctata gaggctcttg gttcaaccga tatatgtata acagttgggg ccaggggacc   360
ctggtcactg tctcctca                                                 378
```

<210> SEQ ID NO 45
<211> LENGTH: 123
<212> TYPE: PRT
<213> ORGANISM: Artificial Sequence

```
<220> FEATURE:
<223> OTHER INFORMATION: Camelid

<400> SEQUENCE: 45

His Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Leu Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120

<210> SEQ ID NO 46
<211> LENGTH: 124
<212> TYPE: PRT
<213> ORGANISM: Artificial Sequence
<220> FEATURE:
<223> OTHER INFORMATION: Camelid

<400> SEQUENCE: 46

Glu Val Gln Leu Val Glu Ser Gly Gly Gly Ser Val Leu Ala Gly Gly
1               5                   10                  15

Ser Leu Arg Leu Ser Cys Val Ala Ser Gly Phe Thr Ser Arg Tyr Asn
            20                  25                  30

Tyr Met Ala Trp Phe Arg Gln Ala Pro Gly Lys Glu Arg Glu Gly Val
        35                  40                  45

Ala Thr Ile Gly Thr Ala Ser Gly Ser Ala Asp Tyr Tyr Gly Ser Val
    50                  55                  60

Lys Asp Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Tyr Gly Thr Ile Ser Leu Thr Pro Ser Asp Tyr Arg
            100                 105                 110

Tyr Trp Gly Gln Gly Thr Leu Val Thr Val Ser Ser
        115                 120

<210> SEQ ID NO 47
<211> LENGTH: 129
<212> TYPE: PRT
<213> ORGANISM: Artificial Sequence
<220> FEATURE:
<223> OTHER INFORMATION: Camelid

<400> SEQUENCE: 47

Gln Val Gln Leu Val Glu Ser Gly Gly Gly Pro Val Gln Ala Gly Glu
1               5                   10                  15

Thr Leu Arg Leu Ser Cys Thr Ala Ser Gly Phe Thr Phe Ala Glu Ala
            20                  25                  30
```

Asp Met Gly Trp Tyr Arg Gln Ala Pro Gly His Glu Cys Glu Leu Val
        35                  40                  45

Ser Thr Ile Thr Thr Glu Gly Ile Thr Ser Ala Ser Ser Tyr Tyr
 50                  55                  60

Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                 85                  90                  95

Val Tyr Tyr Cys Ala Pro Asp Pro Tyr Ala Tyr Ser Thr Tyr Ser Asp
                100                 105                 110

Tyr Cys Ser Trp Ala Gly Thr Gln Gly Thr Leu Val Thr Val Ser
        115                 120                 125

Ser

<210> SEQ ID NO 48
<211> LENGTH: 123
<212> TYPE: PRT
<213> ORGANISM: Artificial Sequence
<220> FEATURE:
<223> OTHER INFORMATION: Camelid

<400> SEQUENCE: 48

Gln Val Gln Leu Val Glu Ser Gly Gly Gly Val Glu Ala Gly Arg
 1               5                  10                  15

Ser Leu Arg Leu Ser Cys Ala Ala Ser Gly Phe Arg Tyr Ala Ala Tyr
                 20                  25                  30

Cys Met Gly Trp Phe Arg Gln Ala Asp Gly Lys Glu Arg Glu Gly Val
        35                  40                  45

Ala Thr Ile Asp Ile Asp Gly Gln Thr Thr His Ala Asp Ser Val Lys
 50                  55                  60

Gly Arg Phe Thr Ile Ser Arg Asp Asn Ala Lys Asn Thr Leu Ser Leu
 65                  70                  75                  80

Gln Met Asn Asp Leu Lys Pro Glu Asp Thr Ala Met Tyr Tyr Cys Ala
                 85                  90                  95

Ala Asp Arg Asp Arg Cys Gly Ser Ile Trp Thr Tyr Ala Tyr Lys Tyr
                100                 105                 110

Arg Gly Gln Gly Thr Gln Val Thr Val Ser Ser
        115                 120

<210> SEQ ID NO 49
<211> LENGTH: 123
<212> TYPE: PRT
<213> ORGANISM: Artificial Sequence
<220> FEATURE:
<223> OTHER INFORMATION: Camelid

<400> SEQUENCE: 49

Gln Val Gln Leu Val Glu Ser Gly Gly Gly Ser Val Glu Ala Gly Gly
 1               5                  10                  15

Ser Leu Arg Leu Ser Cys Ala Ala Ser Gly Phe Arg Tyr Ala Ala Tyr
                 20                  25                  30

Cys Met Gly Trp Phe Arg Gln Ala Asp Gly Lys Glu Arg Glu Gly Val
        35                  40                  45

Ala Thr Ile Asp Ile Asp Gly Gln Thr Thr His Ala Asp Ser Val Lys
 50                  55                  60

Gly Arg Phe Thr Ile Ser Arg Asp Asn Val Lys Asn Thr Leu Ser Leu
 65                  70                  75                  80

Gln Met Asn Asp Leu Lys Pro Glu Asp Thr Ala Met Tyr Tyr Cys Ala
            85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
            115                 120

<210> SEQ ID NO 50
<211> LENGTH: 123
<212> TYPE: PRT
<213> ORGANISM: Artificial Sequence
<220> FEATURE:
<223> OTHER INFORMATION: Camelid

<400> SEQUENCE: 50

Gln Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
            35                  40                  45

Ala Thr Ile Asp Ile Asp Gly Leu Thr Thr His Ala Asp Ser Val Lys
        50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
            85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
            115                 120

<210> SEQ ID NO 51
<211> LENGTH: 123
<212> TYPE: PRT
<213> ORGANISM: Artificial Sequence
<220> FEATURE:
<223> OTHER INFORMATION: Camelid

<400> SEQUENCE: 51

Gln Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
            35                  40                  45

Ala Thr Ile Asp Ile Asp Gly Gln Thr Thr His Ala Asp Ser Val Lys
        50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
            85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
            115                 120

<210> SEQ ID NO 52

```
<211> LENGTH: 123
<212> TYPE: PRT
<213> ORGANISM: Artificial Sequence
<220> FEATURE:
<223> OTHER INFORMATION: Camelid

<400> SEQUENCE: 52

Glu Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120

<210> SEQ ID NO 53
<211> LENGTH: 123
<212> TYPE: PRT
<213> ORGANISM: Artificial Sequence
<220> FEATURE:
<223> OTHER INFORMATION: Camelid

<400> SEQUENCE: 53

Glu Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Leu Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120

<210> SEQ ID NO 54
<211> LENGTH: 123
<212> TYPE: PRT
<213> ORGANISM: Artificial Sequence
<220> FEATURE:
<223> OTHER INFORMATION: Camelid

<400> SEQUENCE: 54

Asp Val Gln Leu Val Glu Ser Gly Gly Gly Ser Val Glu Ala Gly Gly
1               5                   10                  15
```

```
Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Gln Thr Thr His Ala Asp Ser Val Lys
 50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120
```

<210> SEQ ID NO 55
<211> LENGTH: 123
<212> TYPE: PRT
<213> ORGANISM: Artificial Sequence
<220> FEATURE:
<223> OTHER INFORMATION: Camelid

<400> SEQUENCE: 55

```
His Val Gln Leu Val Glu Ser Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Leu Thr Thr His Ala Asp Ser Val Lys
 50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120
```

<210> SEQ ID NO 56
<211> LENGTH: 123
<212> TYPE: PRT
<213> ORGANISM: Artificial Sequence
<220> FEATURE:
<223> OTHER INFORMATION: Camelid

<400> SEQUENCE: 56

```
His Val Gln Leu Val Glu Ser Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Leu Ala Thr His Ala Asp Ser Val Lys
 50                  55                  60

Gly Arg Phe Thr Ile Ser Arg Asp Asn Ala Lys Asn Thr Leu Ser Leu
65                  70                  75                  80
```

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120

<210> SEQ ID NO 57
<211> LENGTH: 123
<212> TYPE: PRT
<213> ORGANISM: Artificial Sequence
<220> FEATURE:
<223> OTHER INFORMATION: Camelid

<400> SEQUENCE: 57

His Val Gln Leu Val Glu Ser Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Arg Lys Glu Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120

<210> SEQ ID NO 58
<211> LENGTH: 123
<212> TYPE: PRT
<213> ORGANISM: Artificial Sequence
<220> FEATURE:
<223> OTHER INFORMATION: Camelid

<400> SEQUENCE: 58

His Val Gln Leu Val Glu Ser Gly Gly Ser Val Gln Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Val Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120

```
<210> SEQ ID NO 59
<211> LENGTH: 123
<212> TYPE: PRT
<213> ORGANISM: Artificial Sequence
<220> FEATURE:
<223> OTHER INFORMATION: Camelid

<400> SEQUENCE: 59

Gln Val Gln Leu Val Glu Ser Gly Gly Gly Ser Val Gln Ala Gly Gly
1               5                   10                  15

Ser Leu Arg Leu Ser Cys Ala Ala Ser Gly Phe Ile Asp Ser Phe Gly
            20                  25                  30

Val Met Ala Trp Phe Arg Gln Ala Pro Gly Lys Glu Arg Glu Gly Val
        35                  40                  45

Ala Ala Val Tyr Arg Arg Ala Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Met Tyr Tyr Cys
                85                  90                  95

Ala Ala Arg Thr Tyr Gly Ser Val Ser Ser Trp Thr Gly Tyr Lys Tyr
            100                 105                 110

Trp Gly Gln Gly Thr Gln Val Thr Val Ser Ser
        115                 120

<210> SEQ ID NO 60
<211> LENGTH: 123
<212> TYPE: PRT
<213> ORGANISM: Artificial Sequence
<220> FEATURE:
<223> OTHER INFORMATION: Camelid

<400> SEQUENCE: 60

Asp Val Gln Leu Val Glu Ser Gly Gly Gly Ser Val Gln Ala Gly Gly
1               5                   10                  15

Ser Leu Arg Leu Ser Cys Ala Ala Ser Gly Phe Ile Asp Ser Phe Gly
            20                  25                  30

Val Met Ala Trp Phe Arg Gln Thr Pro Gly Lys Glu Arg Glu Gly Val
        35                  40                  45

Ala Ala Val Tyr Arg Arg Ala Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Met Tyr Tyr Cys
                85                  90                  95

Ala Ala Arg Thr Tyr Gly Ser Val Ser Ser Trp Thr Gly Tyr Lys Tyr
            100                 105                 110

Trp Gly Gln Gly Thr Gln Val Thr Val Ser Ser
        115                 120

<210> SEQ ID NO 61
<211> LENGTH: 123
<212> TYPE: PRT
<213> ORGANISM: Artificial Sequence
<220> FEATURE:
<223> OTHER INFORMATION: Camelid

<400> SEQUENCE: 61

Asp Val Gln Leu Val Glu Ser Gly Gly Gly Ser Val Gln Val Gly Gly
1               5                   10                  15
```

Ser Leu Thr Leu Ser Cys Ala Val Ser Gly Tyr Thr Asp Ser Tyr Gly
            20                  25                  30

Val Met Ala Trp Phe Arg Gln Ala Pro Gly Lys Glu Arg Glu Gly Val
        35                  40                  45

Ala Ser Ile Tyr Arg Asn Ser Gly Ile Thr Tyr Tyr Pro Asp Ser Val
    50                  55                  60

Lys Gly Arg Phe Thr Ile Ser Arg Asp Asn Ala Lys Asn Thr Val Leu
65                  70                  75                  80

Leu Gln Met Asn Ser Leu Lys Pro Glu Asp Ser Ala Thr Tyr Tyr Cys
                85                  90                  95

Ala Val Arg Ser Phe Gly Ser Val Ser Thr Trp Ala Gly Tyr Val Tyr
            100                 105                 110

Trp Gly Gln Gly Thr Gln Val Thr Val Ser Ser
            115                 120

<210> SEQ ID NO 62
<211> LENGTH: 123
<212> TYPE: PRT
<213> ORGANISM: Artificial Sequence
<220> FEATURE:
<223> OTHER INFORMATION: Camelid

<400> SEQUENCE: 62

Asp Val Gln Leu Val Glu Ser Gly Gly Gly Ser Val Gln Ala Gly Gly
1               5                   10                  15

Ser Leu Arg Leu Ser Cys Ala Ala Ser Gly Phe Ile Asp Ser Phe Gly
            20                  25                  30

Val Met Ala Trp Phe Arg Gln Ala Pro Gly Lys Glu Arg Glu Gly Val
        35                  40                  45

Ala Ala Val Tyr Arg Arg Ala Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Met Tyr Tyr Cys
                85                  90                  95

Ala Ala Arg Thr Tyr Gly Ser Val Ser Ser Trp Thr Gly Tyr Lys Tyr
            100                 105                 110

Trp Gly Arg Gly Thr Gln Val Thr Val Ser Ser
            115                 120

<210> SEQ ID NO 63
<211> LENGTH: 125
<212> TYPE: PRT
<213> ORGANISM: Artificial Sequence
<220> FEATURE:
<223> OTHER INFORMATION: Camelid

<400> SEQUENCE: 63

Asp Val Gln Leu Val Glu Ser Gly Gly Gly Ser Val Arg Ala Gly Gly
1               5                   10                  15

Ser Leu Arg Leu Ser Cys Thr Ala Ser Gly Asp Thr Ser Lys Ser Asp
            20                  25                  30

Cys Met Ala Trp Phe Arg Gln Ala Pro Gly Lys Glu Arg Glu Arg Val
        35                  40                  45

Gly Ala Ile Tyr Thr Arg Asn Gly Tyr Thr His Tyr Ala Asp Ser Val
    50                  55                  60

Asn Gly Arg Phe Thr Ile Ser Gln Asp Asn Ala Lys Asn Ala Leu Tyr

```
               65                  70                  75                  80
Leu Gln Met Ser Gly Leu Lys Pro Glu Asp Thr Ala Met Tyr Tyr Cys
                85                  90                  95

Ala Ala Arg Phe Arg Ile Tyr Gly Gln Cys Val Glu Asp Asp Ile
            100                 105                 110

Asp Tyr Trp Gly Gln Gly Thr Leu Val Thr Val Ser Ser
            115                 120                 125
```

<210> SEQ ID NO 64
<211> LENGTH: 124
<212> TYPE: PRT
<213> ORGANISM: Artificial Sequence
<220> FEATURE:
<223> OTHER INFORMATION: Camelid

<400> SEQUENCE: 64

```
Glu Val Gln Leu Val Glu Ser Gly Gly Gly Ser Val Leu Ala Gly Gly
1               5                   10                  15

Ser Leu Arg Leu Ser Cys Val Ala Ser Gly Phe Thr Arg Tyr Asn
            20                  25                  30

Tyr Met Ala Trp Phe Arg Gln Ala Pro Gly Lys Glu Arg Glu Gly Val
        35                  40                  45

Ala Thr Ile Gly Thr Ala Ser Gly Ser Ala Asp Tyr Tyr Gly Ser Val
    50                  55                  60

Lys Asp Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Tyr Gly Thr Ile Ser Leu Thr Pro Ser Asp Tyr Arg
            100                 105                 110

Tyr Trp Gly Gln Gly Thr Leu Val Thr Val Ser Ser
            115                 120
```

<210> SEQ ID NO 65
<211> LENGTH: 128
<212> TYPE: PRT
<213> ORGANISM: Artificial Sequence
<220> FEATURE:
<223> OTHER INFORMATION: Camelid

<400> SEQUENCE: 65

```
Gln Val Gln Val Val Glu Tyr Gly Gly Gly Ser Val Gln Ala Gly Glu
1               5                   10                  15

Thr Val Arg Leu Ser Cys Thr Ala Ser Gly Phe Thr Phe Ala Glu Ala
            20                  25                  30

Asp Met Gly Trp Tyr Arg Gln Ala Pro Gly His Glu Trp Glu Leu Val
        35                  40                  45

Ser Asn Ile Thr Thr Glu Gly Ile Thr Ser Glu Ala Ser Ser Ser Tyr
    50                  55                  60

Ala Asp Ser Val Arg Gly Arg Phe Thr Ile Phe Asp Asn Ala Lys Asn
65                  70                  75                  80

Met Val Tyr Leu Gln Met Asn Ser Leu Lys His Glu Asp Thr Ala Val
                85                  90                  95

Tyr Tyr Cys Ala Pro Asp Pro Tyr Ala Tyr Ser Thr Tyr Arg Glu Tyr
            100                 105                 110

Cys Thr Trp Ala Gln Gly Thr Gln Gly Thr Leu Val Thr Val Ser Ser
            115                 120                 125
```

```
<210> SEQ ID NO 66
<211> LENGTH: 129
<212> TYPE: PRT
<213> ORGANISM: Artificial Sequence
<220> FEATURE:
<223> OTHER INFORMATION: Camelid

<400> SEQUENCE: 66

Gln Val Gln Leu Val Glu Ser Gly Gly Gly Pro Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Leu Val Thr Val Ser
        115                 120                 125

Ser

<210> SEQ ID NO 67
<211> LENGTH: 129
<212> TYPE: PRT
<213> ORGANISM: Artificial Sequence
<220> FEATURE:
<223> OTHER INFORMATION: Camelid

<400> SEQUENCE: 67

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Leu Val Thr Val Ser
        115                 120                 125

Ser

<210> SEQ ID NO 68
<211> LENGTH: 129
<212> TYPE: PRT
<213> ORGANISM: Artificial Sequence
<220> FEATURE:
<223> OTHER INFORMATION: Camelid
```

<400> SEQUENCE: 68

Gln Val Gln Pro Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Ala Gln Gly Thr Leu Val Thr Val Ser
        115                 120                 125

Ser

<210> SEQ ID NO 69
<211> LENGTH: 129
<212> TYPE: PRT
<213> ORGANISM: Artificial Sequence
<220> FEATURE:
<223> OTHER INFORMATION: Camelid

<400> SEQUENCE: 69

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Gln Val Thr Val Ser
        115                 120                 125

Ser

<210> SEQ ID NO 70
<211> LENGTH: 129
<212> TYPE: PRT
<213> ORGANISM: Artificial Sequence
<220> FEATURE:
<223> OTHER INFORMATION: Camelid

<400> SEQUENCE: 70

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala

```
                    20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Gln Val Thr Val Ser
            115                 120                 125

Ser

<210> SEQ ID NO 71
<211> LENGTH: 129
<212> TYPE: PRT
<213> ORGANISM: Artificial Sequence
<220> FEATURE:
<223> OTHER INFORMATION: Camelid

<400> SEQUENCE: 71

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Leu Val Thr Val Ser
            115                 120                 125

Ser

<210> SEQ ID NO 72
<211> LENGTH: 129
<212> TYPE: PRT
<213> ORGANISM: Artificial Sequence
<220> FEATURE:
<223> OTHER INFORMATION: Camelid

<400> SEQUENCE: 72

His Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
    50                  55                  60
```

```
Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                 85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Gln Val Thr Val Ser
        115                 120                 125

Ser

<210> SEQ ID NO 73
<211> LENGTH: 129
<212> TYPE: PRT
<213> ORGANISM: Artificial Sequence
<220> FEATURE:
<223> OTHER INFORMATION: Camelid

<400> SEQUENCE: 73

Glu Val Gln Leu Val Glu Ser Gly Gly Gly Ser Val Gln Ala Gly Glu
  1               5                  10                  15

Thr Leu Arg Leu Ser Cys Thr Ala Ser Gly Phe Thr Phe Ala Glu Ala
                 20                  25                  30

Asp Met Gly Trp Tyr Arg Gln Ala Pro Gly His Glu Cys Glu Leu Val
             35                  40                  45

Ser Thr Ile Thr Thr Glu Gly Ile Thr Ser Glu Ala Ser Ser Tyr Tyr
         50                  55                  60

Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                 85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Ala Leu Val Thr Val Ser
        115                 120                 125

Ser

<210> SEQ ID NO 74
<211> LENGTH: 129
<212> TYPE: PRT
<213> ORGANISM: Artificial Sequence
<220> FEATURE:
<223> OTHER INFORMATION: Camelid

<400> SEQUENCE: 74

Glu Val Gln Leu Val Glu Ser Gly Gly Gly Ser Val Gln Ala Gly Glu
  1               5                  10                  15

Thr Leu Arg Leu Ser Cys Thr Ala Ser Gly Phe Thr Phe Ala Glu Ala
                 20                  25                  30

Asp Met Gly Trp Tyr Arg Gln Ala Pro Gly His Glu Cys Glu Leu Val
             35                  40                  45

Ser Thr Ile Thr Thr Glu Gly Ile Thr Ser Glu Ala Ser Ser Tyr Tyr
         50                  55                  60

Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                 85                  90                  95
```

-continued

Val Tyr Tyr Cys Ala Pro Asp Pro Tyr Ala Tyr Ser Thr Tyr Ser Asp
                100                 105                 110

Tyr Cys Thr Trp Ala Gln Gly Thr Gln Gly Thr Leu Val Thr Val Ser
        115                 120                 125

Ser

<210> SEQ ID NO 75
<211> LENGTH: 129
<212> TYPE: PRT
<213> ORGANISM: Artificial Sequence
<220> FEATURE:
<223> OTHER INFORMATION: Camelid

<400> SEQUENCE: 75

Glu Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
                100                 105                 110

Tyr Cys Ser Trp Ala Gln Gly Thr Gln Gly Thr Gln Val Thr Val Ser
        115                 120                 125

Ser

<210> SEQ ID NO 76
<211> LENGTH: 129
<212> TYPE: PRT
<213> ORGANISM: Artificial Sequence
<220> FEATURE:
<223> OTHER INFORMATION: Camelid

<400> SEQUENCE: 76

Glu Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
                100                 105                 110

Tyr Cys Thr Trp Ala Gln Gly Thr Gln Gly Thr Gln Val Thr Val Ser
        115                 120                 125

Ser

<210> SEQ ID NO 77
<211> LENGTH: 129
<212> TYPE: PRT
<213> ORGANISM: Artificial Sequence
<220> FEATURE:
<223> OTHER INFORMATION: Camelid

<400> SEQUENCE: 77

```
Asp Val Gln Leu Val Glu Ser Arg Gly Gly Ser Val Gln Ala Gly Glu
1               5                   10                  15
Thr Leu Arg Leu Ser Cys Thr Ala Ser Gly Phe Thr Phe Ala Glu Ala
            20                  25                  30
Asp Met Gly Trp Tyr Arg Gln Ala Pro Gly His Glu Cys Glu Leu Val
        35                  40                  45
Ser Thr Ile Thr Thr Glu Gly Ile Thr Ser Glu Ala Ser Ser Tyr Tyr
    50                  55                  60
Ala Asp Ser Val Arg Gly Arg Phe Thr Ile Ser Arg Asp Asn Ala Lys
65                  70                  75                  80
Asn Met Val Tyr Leu Gln Met Asn Ser Leu Lys Pro Glu Asp Thr Ala
                85                  90                  95
Val Tyr Tyr Cys Ala Pro Asp Pro Tyr Ala Tyr Ser Thr Tyr Ser Asp
            100                 105                 110
Tyr Cys Thr Trp Ala Gln Gly Thr Gln Gly Thr Leu Val Thr Val Ser
        115                 120                 125
Ser
```

<210> SEQ ID NO 78
<211> LENGTH: 129
<212> TYPE: PRT
<213> ORGANISM: Artificial Sequence
<220> FEATURE:
<223> OTHER INFORMATION: Camelid

<400> SEQUENCE: 78

```
Asp Val Gln Leu Val Glu Ser Gly Gly Gly Ser Val Gln Ala Gly Glu
1               5                   10                  15
Thr Leu Arg Leu Ser Cys Thr Ala Ser Gly Phe Thr Phe Ala Glu Ala
            20                  25                  30
Asp Met Gly Trp Tyr Arg Gln Ala Pro Gly His Val Cys Glu Leu Val
        35                  40                  45
Ser Thr Ile Thr Thr Glu Gly Ile Thr Ser Glu Ala Ser Ser Tyr Tyr
    50                  55                  60
Ala Asp Ser Val Arg Gly Arg Phe Thr Ile Ser Arg Asp Asn Ala Lys
65                  70                  75                  80
Asn Met Val Tyr Leu Gln Met Asn Ser Leu Lys Pro Glu Asp Thr Ala
                85                  90                  95
Val Tyr Tyr Cys Ala Pro Asp Pro Tyr Ala Tyr Ser Thr Tyr Ser Asp
            100                 105                 110
Tyr Cys Ser Trp Ala Gln Gly Thr Gln Gly Thr Gln Val Thr Val Ser
        115                 120                 125
Ser
```

<210> SEQ ID NO 79
<211> LENGTH: 128
<212> TYPE: PRT
<213> ORGANISM: Artificial Sequence
<220> FEATURE:

<223> OTHER INFORMATION: Camelid

<400> SEQUENCE: 79

```
Asp Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly Leu Glu Cys Glu Leu Val
        35                  40                  45

Ser Thr Ile Thr Thr Glu Gly Ile Thr Ser Glu Ala Ser Ser Tyr Ala
    50                  55                  60

Asp Ser Val Arg Gly Arg Phe Thr Ile Ser Arg Asp Asn Ala Lys Asn
65                  70                  75                  80

Met Val Tyr Leu Gln Met Asn Ser Leu Lys Pro Glu Asp Thr Ala Val
                85                  90                  95

Tyr Tyr Cys Ala Pro Asp Pro Tyr Ala Tyr Ser Thr Tyr Ser Glu Tyr
            100                 105                 110

Cys Thr Trp Ala Gln Gly Thr Gln Gly Thr Leu Val Thr Val Ser Ser
        115                 120                 125
```

<210> SEQ ID NO 80
<211> LENGTH: 129
<212> TYPE: PRT
<213> ORGANISM: Artificial Sequence
<220> FEATURE:
<223> OTHER INFORMATION: Camelid

<400> SEQUENCE: 80

```
Asp Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Leu Val Thr Val Ser
        115                 120                 125

Ser
```

<210> SEQ ID NO 81
<211> LENGTH: 129
<212> TYPE: PRT
<213> ORGANISM: Artificial Sequence
<220> FEATURE:
<223> OTHER INFORMATION: Camelid

<400> SEQUENCE: 81

```
Asp Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30
```

```
Asp Met Gly Trp Tyr Arg Gln Ala Pro Gly His Glu Cys Glu Leu Val
        35                  40                  45

Ser Thr Ile Thr Thr Glu Gly Ile Thr Ser Val Ala Ser Ser Tyr Tyr
        50                  55                  60

Ala Asp Ser Val Arg Gly Arg Phe Thr Ile Ser Arg Asp Asn Ala Lys
 65              70                  75                      80

Asn Met Val Tyr Leu Gln Met Asn Ser Leu Lys Pro Glu Asp Thr Ala
                 85                  90                  95

Val Tyr Tyr Cys Ala Pro Asp Pro Tyr Ala Tyr Ser Thr Tyr Ser Asp
                100                 105             110

Tyr Cys Thr Trp Ala Gln Gly Thr Gln Gly Thr Gln Val Thr Val Ser
            115                 120                 125

Ser
```

SINGLE DOMAIN ANTIBODIES DIRECTED AGAINST KRAS

CROSS REFERENCE TO RELATED APPLICATIONS

This application claims the benefit of U.S. Provisional Patent Application No. 62/067,908, filed on Oct. 23, 2014, U.S. Provisional Patent Application No. 62/148,656, filed on Apr. 16, 2015, U.S. Provisional Patent Application No. 62/188,353 filed on Jul. 2, 2015, and U.S. Provisional Patent Application No. 62/210,795, filed on Aug. 27, 2015, the contents of which are incorporated herein by reference in their entirety.

SEQUENCE LISTING

The present application is being filed along with a Sequence Listing in electronic format. The Sequence Listing is provided as a file titled "Sequence_Listing_STP25.txt," created Sep. 30, 2015, last modified Oct. 22, 2015, and is 83,000 bytes in size. The information in the electronic format of the Sequence Listing is incorporated herein by reference in its entirety.

BACKGROUND

The use of single-domain antibodies (sdAbs) as single antigen-binding proteins or as an antigen-binding domain in larger protein or polypeptide offers a number of significant advantages over the use of conventional antibodies or antibody fragments. The advantages of sdAbs include: only a single domain is required to bind an antigen with high affinity and with high selectivity; sdAbs can be expressed from a single gene and require no post-translational modification; sdAbs are highly stable to heat, pH, proteases and other denaturing agents or conditions; sdAbs are inexpensive to prepare; and sdAbs can access targets and epitopes not accessible to conventional antibodies.

There are a number of diseases or conditions, such as cancer, that are caused by aberrant intracellular or transmembrane components such as nucleotides and proteins. Elimination of the aberrant components can be used to prevent or treat the diseases or conditions. There are a number of pharmacological compounds available for treatment, but the compounds can be ineffective, undeliverable, or toxic to unaffected cells.

Other treatments include the use of therapeutic proteins or agents that contain an exogenous targeting sequence so that the therapeutic agent can be recognized by receptors in the cell membrane, enabling the therapeutic agent to cross the cell membrane and enter the cell. Once the therapeutic agent is inside the cell, the therapeutic agent can interact with the target component in order to treat the disease. However, the use of exogenous targeting sequence can limit the cell type that is targeted by the therapeutic agent, and adds to the cost of manufacturing the therapeutic agent.

For the foregoing reasons, there is a need for compositions and methods to treat or prevent a disease that do not rely on exogenous targeting sequences or chemical compositions in order to enter the cell, and that are effective in targeting only the affected cells in the body.

The present invention relates to single-domain antibodies (sdAbs), proteins and polypeptides comprising the sdAbs. The sdAbs are directed against intracellular components that cause a condition or disease. The invention also includes nucleic acids encoding the sdAbs, proteins and polypeptides, and compositions comprising the sdAbs. The invention includes the use of the compositions, sdAbs, proteins or polypeptides for prophylactic, therapeutic or diagnostic purposes. The invention also includes the use of monoclonal antibodies directed towards the sdAbs of the invention.

SUMMARY

One embodiment of the invention is a single-domain antibody (sdAb) directed against an intracellular component. The intracellular component can be, for example, a protein, nucleic acid, lipid, carbohydrate, STAT1, STAT2, STAT3, STAT4, STAT5a, STAT5b, STAT6, TNF-alpha, and KRAS.

In another embodiment, the invention is directed towards an anti-STAT3 sdAb. Optionally, the anti-STAT3 sdAb comprises an amino acid sequence set forth in SEQ ID NO:3 or SEQ ID NO:4.

In another embodiment, the invention is directed towards an isolated polypeptide comprising an amino acid sequence encoding an anti-STAT sdAb, such as, for example, the polypeptide set forth in SEQ ID NO:3 or SEQ ID NO:4.

In yet another embodiment, the invention is directed towards a host cell, and the host cell expresses the amino acid sequence of the sdAb such as, for example, the amino acid set forth in SEQ ID NO:3 or SEQ ID NO:4.

One embodiment of the invention is a pharmaceutical composition comprising a sdAb, or a polypeptide, and a pharmaceutically acceptable carrier. Optionally, the sdAb comprises an anti-STAT3 sdAb comprising an amino acid sequence set forth in SEQ ID NO:3 or SEQ ID NO:4, and the polypeptide comprises an isolated polypeptide comprising an amino acid sequence set forth in SEQ ID NO:3 or SEQ ID NO:4.

Another embodiment of the invention is a method to diagnose a disorder mediated by STAT3 in a subject, the method comprising the steps of a) contacting a biological sample with the sdAb, or a polypeptide; b) determining the amount of STAT3 in the biological sample; and c) comparing the amount determined in step (b) with a standard, a difference in amount indicating the presence of the disorder.

Another embodiment of the invention is a method of preventing or treating a disease or disorder, or preventing recurrence of a disease mediated by STAT3, or for use in the treatment of cancer, or diseases caused by abnormal cellular proliferation, comprising administering an anti-STAT3 sdAb, or a polypeptide, to a subject in need thereof. Optionally, the sdAb comprises an anti-STAT3 sdAb comprising an amino acid sequence set forth in SEQ ID NO:3 or SEQ ID NO:4 and the polypeptide comprises an isolated polypeptide comprising an amino acid sequence set forth in SEQ ID NO:3 or SEQ ID NO:4.

One embodiment of the invention is an anti-TNF-alpha sdAb. Optionally, the anti-TNF-alpha sdAb comprises an amino acid sequence set forth in SEQ ID NO:5, SEQ ID NO:6 or SEQ ID NO:7. The invention also comprises an isolated polypeptide comprising an amino acid sequence set forth in SEQ ID NO:5, SEQ ID NO:6 or SEQ ID NO:7.

Another embodiment of the invention is a host cell expressing the amino acid sequence set forth in SEQ ID NO:5, SEQ ID NO:6 or SEQ ID NO:7.

In another embodiment, the invention is also a pharmaceutical composition comprising a sdAb or a polypeptide and a pharmaceutically acceptable carrier. Optionally, the sdAb comprises an anti-TNF-alpha sdAb comprising an amino acid sequence set forth in SEQ ID NO:5, SEQ ID NO:6 or SEQ ID NO:7 and the polypeptide comprises an isolated polypeptide comprising an amino acid sequence set forth in SEQ ID NO:5, SEQ ID NO:6 or SEQ ID NO:7.

Another embodiment of the invention is a method to diagnose a disorder mediated by TNF-alpha in a subject, the method comprising the steps of a) contacting a biological sample with a sdAb or a polypeptide; b) determining the amount of TNF-alpha in the biological sample; and c) comparing the amount determined in step (b) with a standard, a difference in amount indicating the presence of the disorder.

In one embodiment, the invention describes a method of preventing or treating a disease or disorder or recurrence of a disease or disorder mediated by TNF-alpha, or for use in the treatment of cancer, or diseases caused by abnormal cellular proliferation, comprising administering an anti-TNF-alpha sdAb, or a polypeptide, to a mammal in need thereof. Optionally, the anti-TNF-alpha sdAb comprises an amino acid sequence set forth in SEQ ID NO:5, SEQ ID NO:6 or SEQ ID NO:7 and the polypeptide comprises isolated polypeptide, the isolated polypeptide comprising an amino acid sequence set forth in SEQ ID NO:5, SEQ ID NO:6 or SEQ ID NO:7.

One embodiment of the invention is an anti-KRAS sdAb. Optionally, the anti-KRAS sdAb comprises an amino acid sequence set forth in SEQ ID NO:2. In one aspect, the invention comprises an isolated polypeptide, wherein the isolated polypeptide comprises an amino acid sequence set forth in SEQ ID NO:2. In another aspect, the invention comprises a host cell expressing the amino acid sequence set forth in SEQ ID NO:2.

Another embodiment of the invention is a pharmaceutical composition, comprising a sdAb or a polypeptide, and a pharmaceutically acceptable carrier. Optionally, the sdAb comprises an anti-KRAS sdAb comprising an amino acid sequence set forth in SEQ ID NO:2 and the polypeptide comprises isolated polypeptide comprising an amino acid sequence set forth in SEQ ID NO:2.

An additional embodiment of the invention is method to diagnose a disorder mediated by KRAS in a subject, the method comprising the steps of a) contacting a biological sample with a sdAb or a polypeptide; b) determining the amount of KRAS in said biological sample; and c) comparing the amount determined in step (b) with a standard, a difference in amount indicating the presence of the disorder. Optionally, the sdAb comprises an anti-KRAS sdAb comprising an amino acid sequence set forth in SEQ ID NO: 2 and the polypeptide comprises isolated polypeptide comprising an amino acid sequence set forth in SEQ ID NO:2.

The invention also comprises a method of treating a disease using an anti-KRAS sdAb, the method comprising administering an effective amount of an anti-KRAS sdAb to a subject in need thereof.

In one embodiment, the invention describes a method of preventing or treating a disease or disorder, or the recurrence of a disease or disorder, mediated by KRAS, or for use in the treatment of cancer, or diseases caused by abnormal cellular proliferation, comprising administering an anti-KRAS sdAb or a polypeptide, to a mammal in need thereof. Optionally, the anti-KRAS sdAb comprises an amino acid sequence set forth in SEQ ID NO: 2 and the polypeptide comprises isolated polypeptide comprising an amino acid sequence set forth in SEQ ID NO: 2.

In one embodiment, the invention describes a method of administering the sdAb of the invention, the method comprising intravenous administration, intramuscular administration, oral administration, rectal administration, intraocular administration, enteral administration, parenteral administration, subcutaneous administration, transdermal administration, administered as eye drops, administered as nasal spray, administered by inhalation or nebulization, topical administration, and administered as an implantable drug.

In another embodiment, the invention describes a method of treating a disease, preventing a disease or preventing the reoccurrence of a disease using the sdAb of the invention in combination with one or more compounds. Optionally, the one or more compounds is a transcriptional inhibitor.

In another embodiment, the invention describes a method of measuring the levels of a sdAb, the method comprising the steps of a) generating a mouse monoclonal antibody directed against one or more domains of the sdAb; b) performing an immunoassay to determine the amount of sdAb in a subject; and c) quantifying the amount of sdAb in the subject.

DRAWINGS

These and other features, aspects, and advantages of the present invention will become better understood with regard to the following description, appended claims, and accompanying drawings where:

Figure 6:
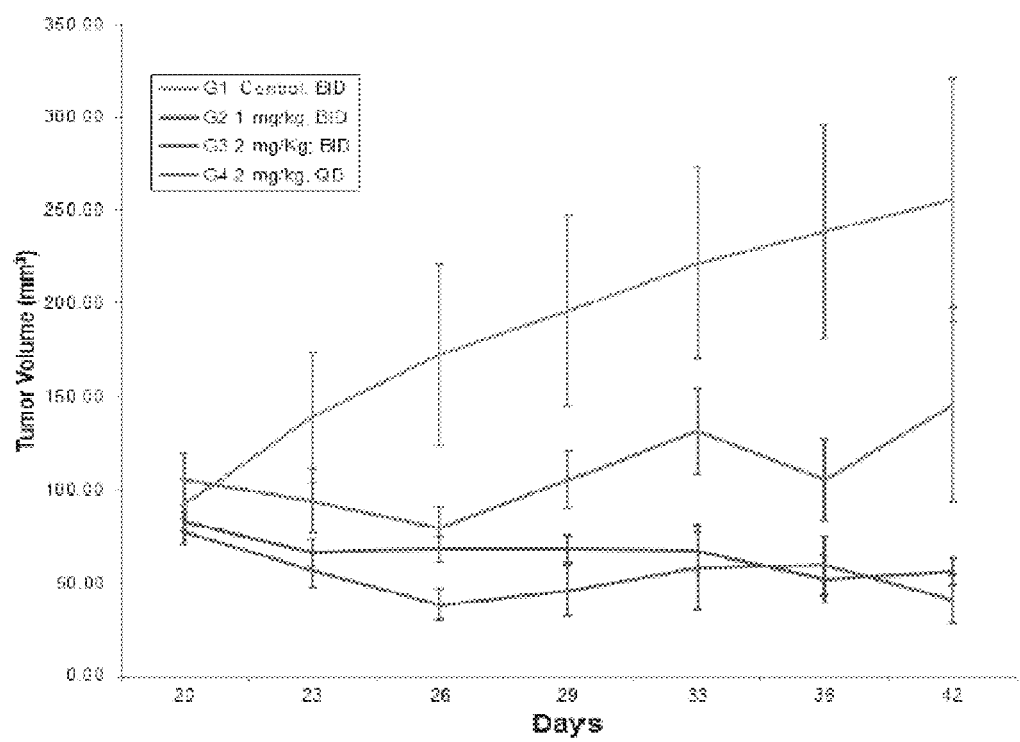
Figure 7:
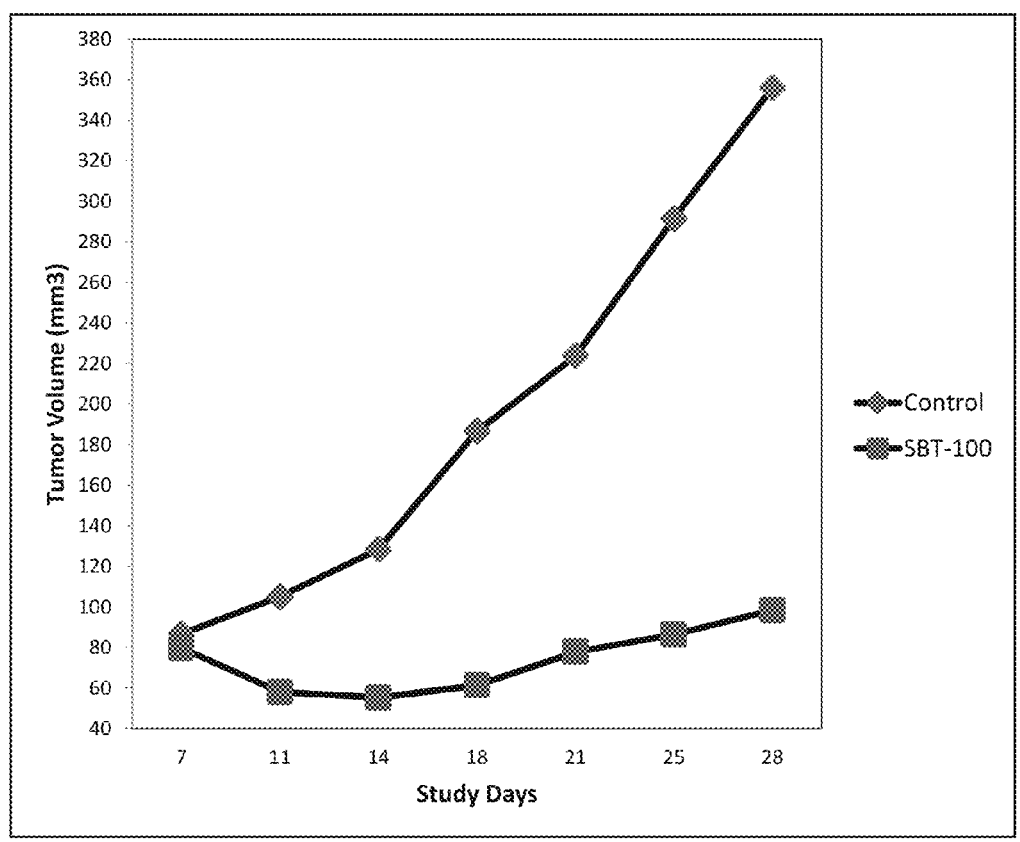
Figure 8:
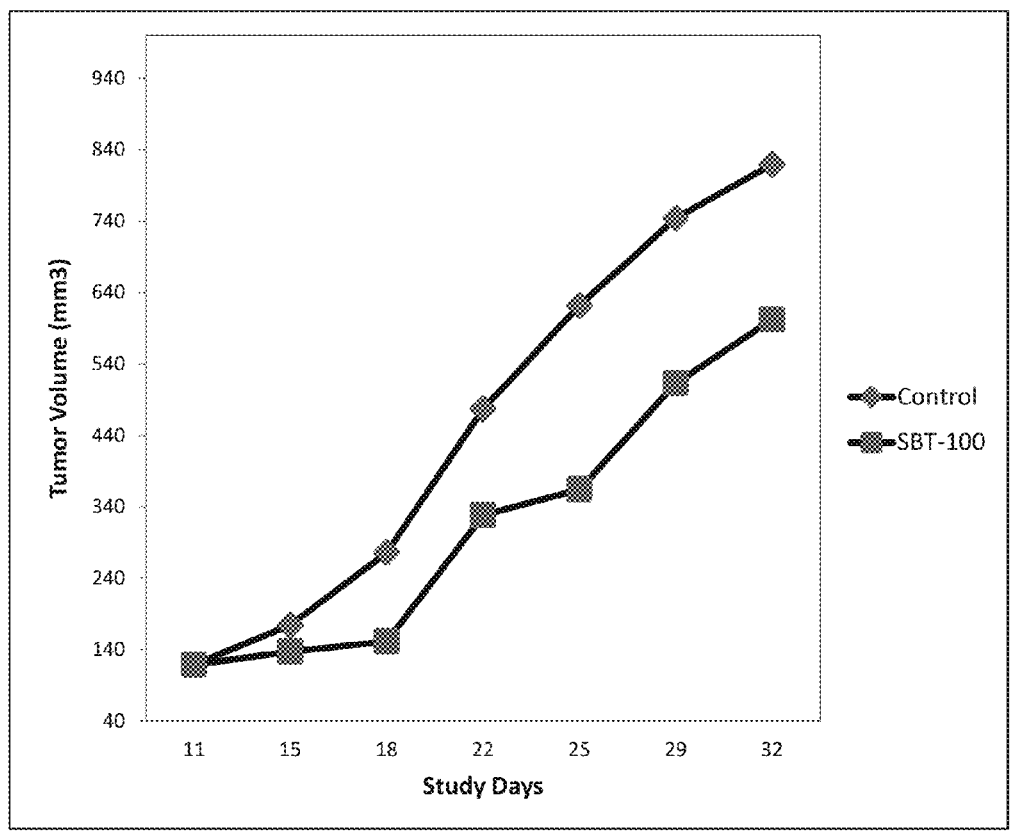
Figure 9:
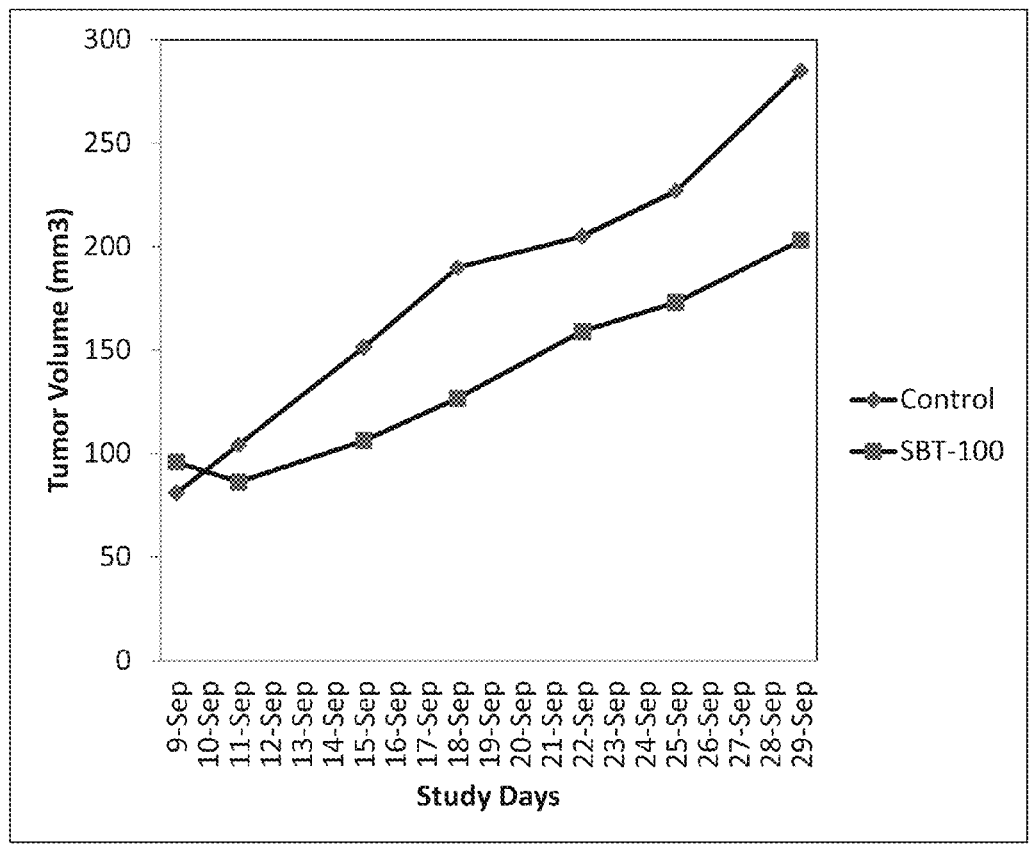
Figure 10:
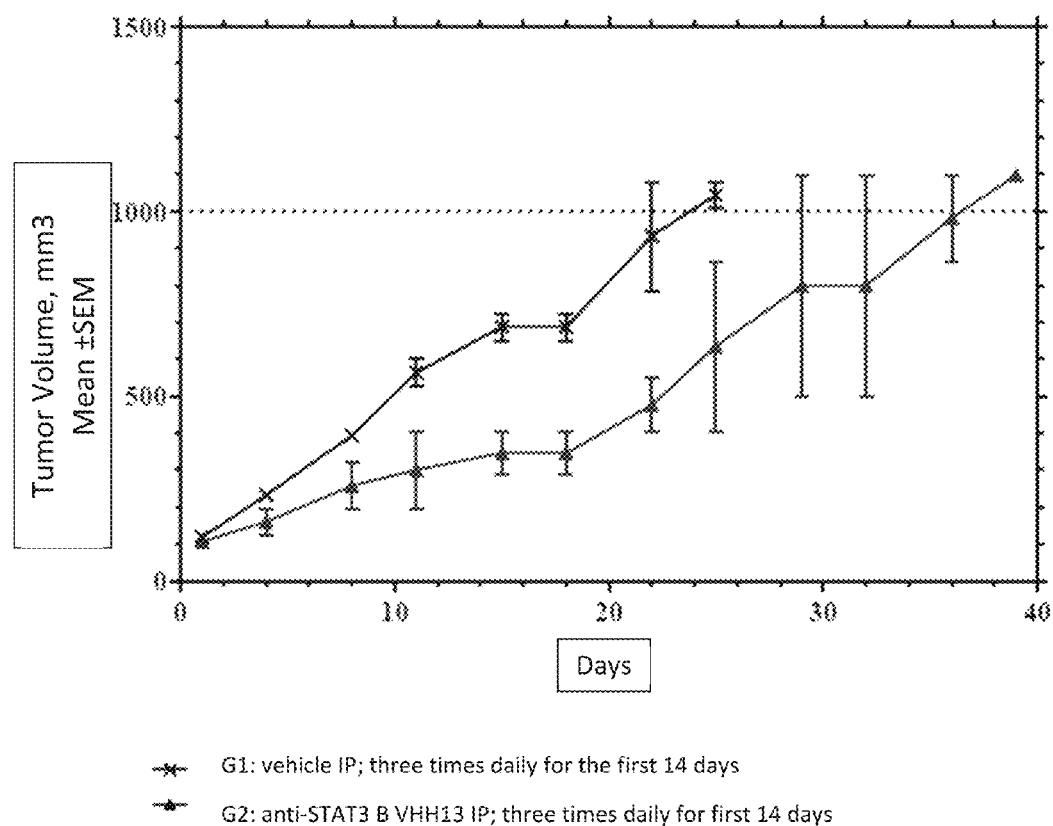
Figure 11:
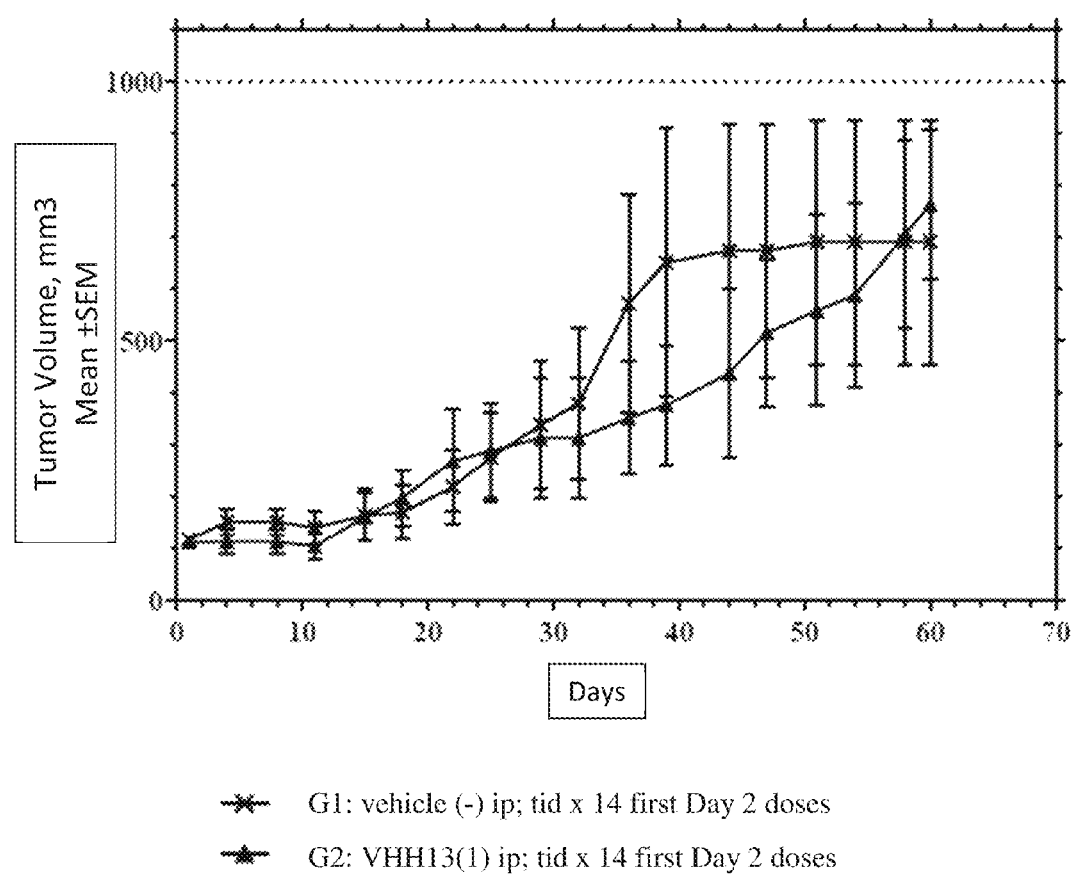
Figure 12:
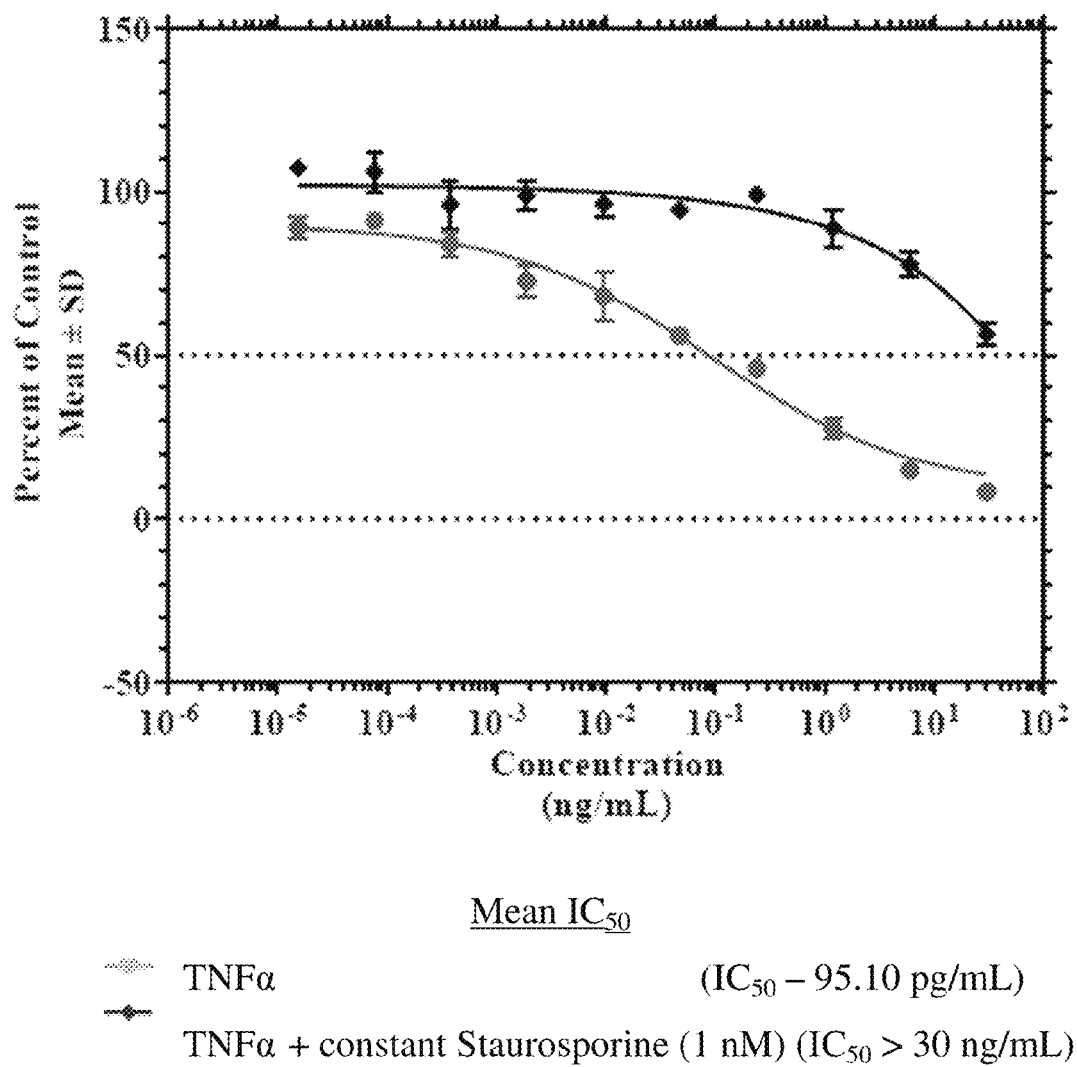
Figure 13:
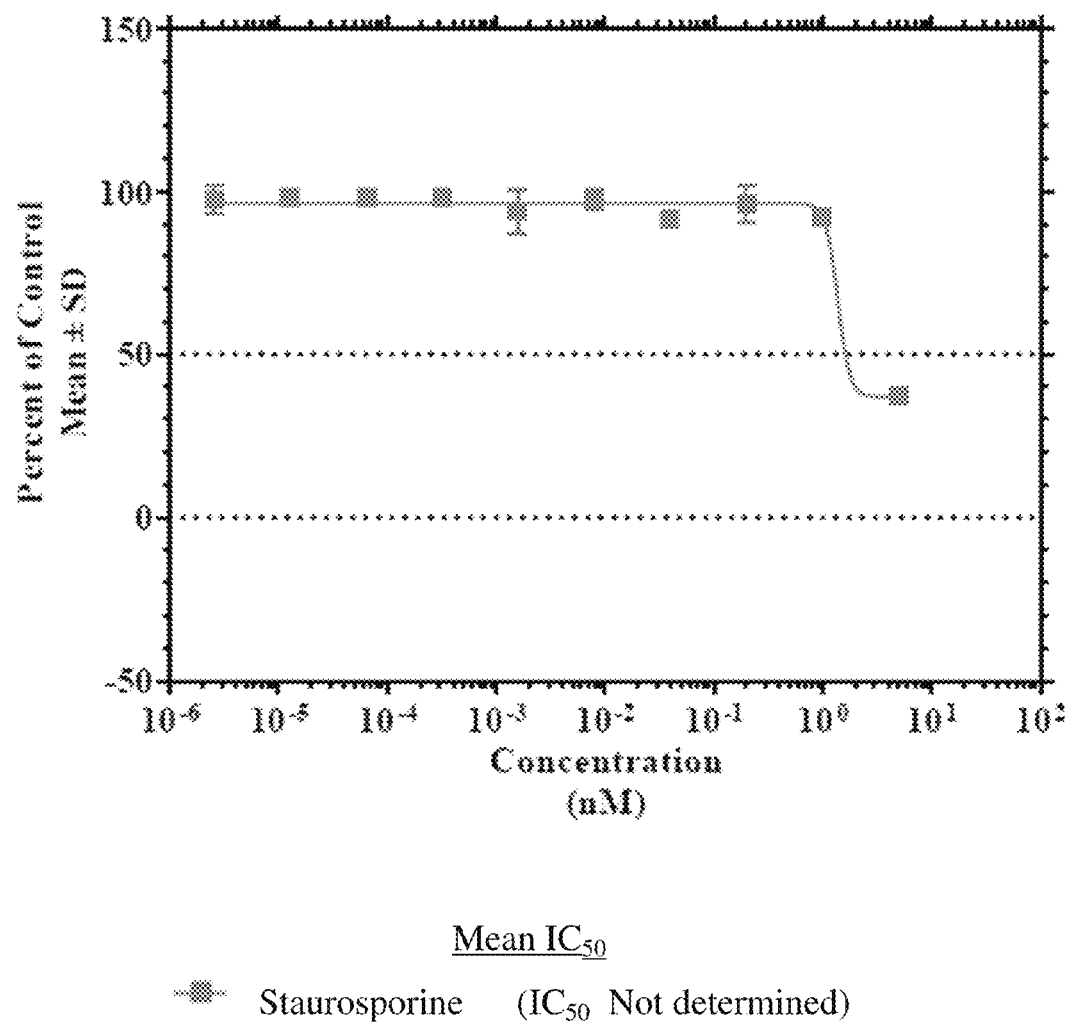

FIG. 6 illustrates the growth inhibition of anti-STAT3 bacterial VHH13 (SEQ. ID. NO. 3) sdAb in MDA-MB-231 xenograft model at doses ranging from 1 mg/kg twice daily to 2 mg/kg twice daily or 2 mg/kg/day;

FIG. 7 illustrates the growth inhibition of anti-STAT3 bacterial VHH13 (SEQ ID NO:3) sdAb in the MDA-MB-231 xenograft model, dosed at 5 mg/kg/twice daily;

FIG. 8 illustrates the growth inhibition of anti-STAT3 bacterial VHH13 (SEQ ID NO:3) sdAb in the DU145 xenograft model, dosed at 5 mg/kg/twice daily;

FIG. 9 illustrates the growth inhibition of anti-STAT3 bacterial VHH13 (SEQ ID NO:3) sdAb in the PANC-1 xenograft model, dosed at 5 mg/kg/twice daily;

FIG. 10 illustrates the growth inhibition of anti-STAT3 bacterial VHH13 (SEQ ID NO:3) sdAb in the MCF-7 xenograft model, dosed at 1 mg/kg/three times daily;

FIG. 11 illustrates the growth inhibition of anti-STAT3 bacterial VHH13 (SEQ ID NO:3) sdAb in the BT-474 xenograft model, dosed at 1 mg/kg/three times daily;

FIG. 12 illustrates the cytotoxicity of TNF-alpha in U937 cells;

FIG. 13 illustrates the cytotoxicity of Staurosporine in U937 cells; and

Figure 14:
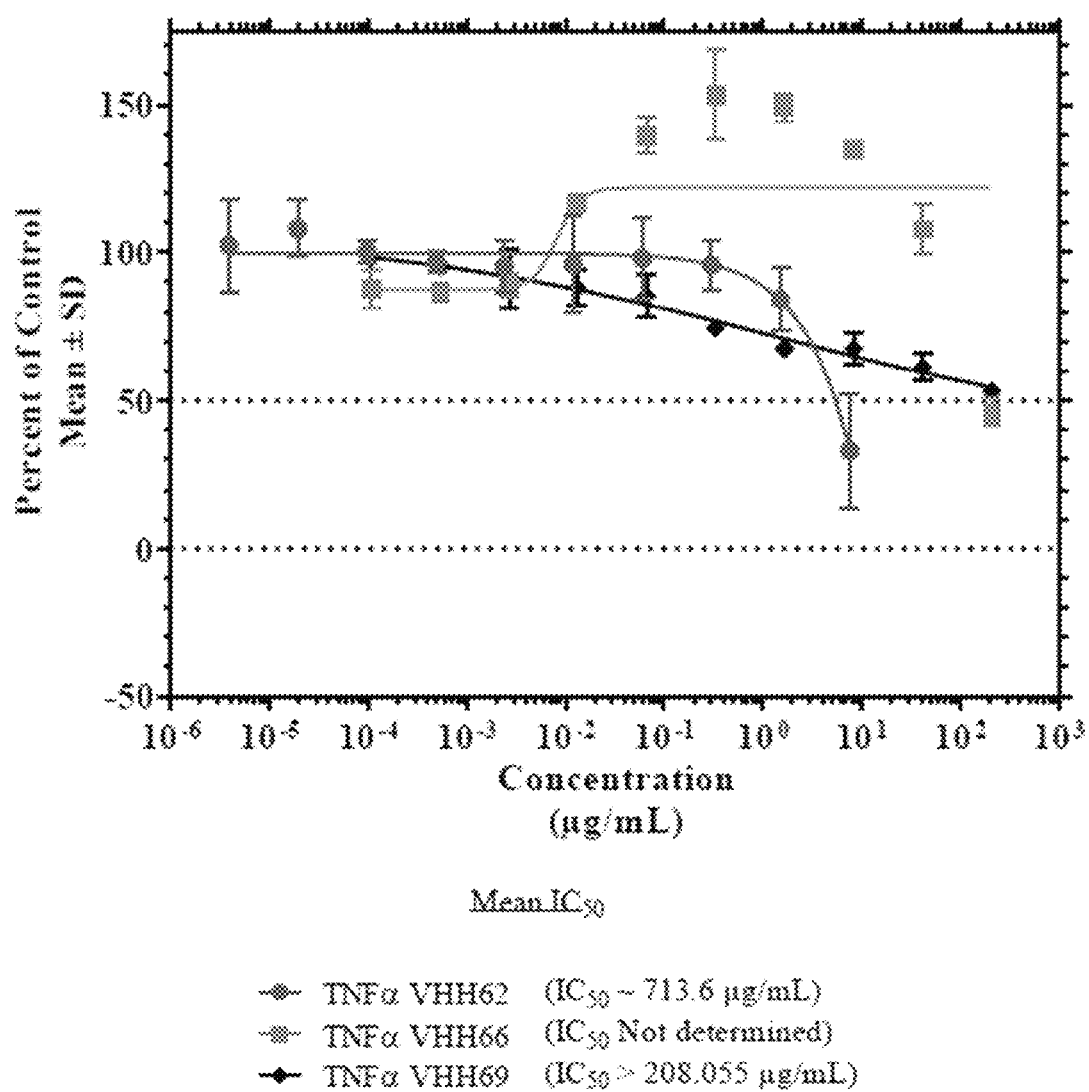

FIG. 14 illustrates inhibition of TNF-alpha cytotoxicity by anti-TNF-alpha sdAbs.

DESCRIPTION

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

The term "antigenic determinant" refers to the epitope on the antigen recognized by the antigen-binding molecule (such as an sdAb or polypeptide of the invention) and more in particular by the antigen-binding site of the antigen-binding molecule. The terms "antigenic determinant" and "epitope" may also be used interchangeably. An amino acid sequence that can bind to, that has affinity for and/or that has specificity for a specific antigenic determinant, epitope, antigen or protein is said to be "against" or "directed against" the antigenic determinant, epitope, antigen or protein.

As used herein, the term "comprise" and variations of the term, such as "comprising" and "comprises," are not intended to exclude other additives, components, integers or steps.

It is contemplated that the sdAbs, polypeptides and proteins described herein can contain so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Conservative amino acid substitutions are well known in the art. Conservative substitutions are substitutions in which one amino acid within the following groups (a)-(e) is substituted by another amino acid within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Other conservative substitutions include: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A "domain" as used herein generally refers to a globular region of an antibody chain, and in particular to a globular region of a heavy chain antibody, or to a polypeptide that essentially consists of such a globular region.

The amino acid sequence and structure of an sdAb is typically made up of four framework regions or "FRs," which are referred to as "Framework region 1" or "FR1"; as "Framework region 2" or"FR2"; as "Framework region 3" or "FR3"; and as "Framework region 4" or "FR4," respectively. The framework regions are interrupted by three complementarity determining regions or "CDRs," which are referred as "Complementarity Determining Region 1" or "CDR1"; as "Complementarity Determining Region 2" or "CDR2"; and as "Complementarity Determining Region 3" or "CDR3," respectively.

As used herein, the term "humanized sdAb" means an sdAb that has had one or more amino acid residues in the amino acid sequence of the naturally occurring VHH sequence replaced by one or more of the amino acid residues that occur at the corresponding position in a VH domain from a conventional 4-chain antibody from a human. This can be performed by methods that are well known in the art. For example, the FRs of the sdAbs can be replaced by human variable FRs.

As used herein, an "isolated" nucleic acid or amino acid has been separated from at least one other component with which it is usually associated, such as its source or medium, another nucleic acid, another protein/polypeptide, another biological component or macromolecule or contaminant, impurity or minor component.

The term "mammal" is defined as an individual belonging to the class Mammalia and includes, without limitation, humans, domestic and farm animals, and zoo, sports, and pet animals, such as cows, horses, sheep, dogs and cats.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, PBS (phosphate-buffered saline), and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined above, use thereof in the composition of the present invention is contemplated.

A "quantitative immunoassay" refers to any means of measuring an amount of antigen present in a sample by using an antibody. Methods for performing quantitative immunoassays include, but are not limited to, enzyme-linked immunosorbent assay (ELISA), specific analyte labeling and recapture assay (SALRA), liquid chromatography, mass spectrometry, fluorescence-activated cell sorting, and the like.

The term "solution" refers to a composition comprising a solvent and a solute, and includes true solutions and suspensions. Examples of solutions include a solid, liquid or gas dissolved in a liquid and particulates or micelles suspended in a liquid.

The term "specificity" refers to the number of different types of antigens or antigenic determinants to which a particular antigen-binding molecule or antigen-binding protein molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to one of skill in the art, affinity can be determined depending on the specific antigen of interest. Avidity is the measure of the strength of binding between an antigen-binding molecule and the antigen. Avidity is related to both the affinity between an antigenic determinant and its antigen binding site on the antigen-binding molecule and the number of pertinent binding sites present on the antigen-binding molecule. Specific binding of an antigen-binding protein to an antigen or antigenic determinant can be determined by any known manner, such as, for example, Scatchard analysis and/or competitive binding assays, such as radioimmunoassays (RIA), enzyme immunoassays (EIA) and sandwich competition assays.

As used herein, the term "recombinant" refers to the use of genetic engineering methods (for example, cloning, and amplification) used to produce the sdAbs of the invention.

A "single domain antibody," "sdAb" or "VHH" can be generally defined as a polypeptide or protein comprising an amino acid sequence that is comprised of four framework regions interrupted by three complementarity determining regions. This is represented as FR1-CDR1-FR2-CDR2-FR3-CDR3-FR4. An sdAb of the invention also includes a polypeptide or protein that comprises the sdAb amino acid sequence. Typically, sdAbs are produced in camelids such as llamas, but can also be synthetically generated using techniques that are well known in the art. As used herein, the variable domains present in naturally occurring heavy chain antibodies will also be referred to as "VHH domains," in order to distinguish them from the heavy chain variable domains that are present in conventional 4-chain antibodies, referred to as "VH domains," and from the light chain variable domains that are present in conventional 4-chain antibodies, referred to as "VL domains." "VHH" and "sdAb" are used interchangeably herein. The numbering of the amino acid residues of a sdAb or polypeptide is according to the general numbering for VH domains given by Kabat et al. ("Sequence of proteins of immunological interest," US Public Health Services, NIH Bethesda, Md., Publication No. 91). According to this numbering, FR1 of a sdAb comprises the amino acid residues at positions 1-30, CDR1 of a sdAb comprises the amino acid residues at positions 31-36, FR2 of a sdAb comprises the amino acids at positions 36-49, CDR2 of a sdAb comprises the amino acid residues at positions 50-65, FR3 of a sdAb comprises the amino acid residues at positions 66-94, CDR3 of a sdAb comprises the amino acid residues at positions 95-102, and FR4 of a sdAb comprises the amino acid residues at positions 103-113.

The term "synthetic" refers to production by in vitro chemical or enzymatic synthesis.

The term "target" as used herein refers to any component, antigen, or moiety that is recognized by the sdAb. The term "intracellular target" refers to any component, antigen, or moiety present inside a cell. A "transmembrane target" is a component, antigen, or moiety that is located within the cell membrane. An "extracellular target" refers to a component, antigen, or moiety that is located outside of the cell.

A "therapeutic composition" as used herein means a substance that is intended to have a therapeutic effect such as pharmaceutical compositions, genetic materials, biologics, and other substances. Genetic materials include substances intended to have a direct or indirect genetic therapeutic effect such as genetic vectors, genetic regulator elements, genetic structural elements, DNA, RNA and the like. Biologics include substances that are living matter or derived from living matter intended to have a therapeutic effect.

As used herein, the phrases "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by an ordinary medical practitioner, and may vary depending on factors known in the art, such as, e.g., the type of disease, the patient's history and age, the stage of disease, and the administration of other therapeutic agents.

The present invention relates to single-domain antibodies (sdAbs) that are directed against intracellular components, as well as to proteins and polypeptides comprising the sdAbs and nucleotides encoding the proteins and polypeptides. The invention can also relate to sdAbs that are directed against intercellular, transcellular and extracellular targets or antigens. The invention also includes nucleic acids encoding the sdAbs, proteins and polypeptides, and compositions comprising the sdAbs. The invention includes the use of the compositions, sdAbs, proteins or polypeptides for prophylactic, therapeutic or diagnostic purposes.

SdAbs have a number of unique structural characteristics and functional properties which make sdAbs highly advantageous for use as functional antigen-binding domains or proteins. SdAbs functionally bind to an antigen in the absence of a light chain variable domain, and can function as a single, relatively small, functional antigen-binding structural unit, domain or protein. This distinguishes sdAbs from the domains of conventional antibodies, which by themselves do not function as an antigen-binding protein or domain, but need to be combined with conventional antibody fragments such as Fab fragments or ScFv's fragment in order to bind an antigen.

SdAbs can be obtained using methods that are well known in the art. For example, one method for obtaining sdAbs includes (a) immunizing a Camelid with one or more antigens, (b) isolating peripheral lymphocytes from the immunized Camelid, obtaining the total RNA and synthesizing the corresponding cDNAs, (c) constructing a library of cDNA fragments encoding VHH domains, (d) transcribing the VHH domain-encoding cDNAs obtained in step (c) to mRNA using PCR, converting the mRNA to ribosome display format, and selecting the VHH domain by ribosome display, and (e) expressing the VHH domain in a suitable vector and, optionally purifying the expressed VHH domain.

Another method of obtaining the sdAbs of the invention is by preparing a nucleic acid encoding an sdAb using techniques for nucleic acid synthesis, followed by expression of the nucleic acid in vivo or in vitro. Additionally, the sdAb, polypeptides and proteins of the invention can be prepared using synthetic or semi-synthetic techniques for preparing proteins, polypeptides or other amino acid sequences.

The sdAbs of the invention will generally bind to all naturally occurring or synthetic analogs, variants, mutants, alleles, parts and fragments of the target, or at least to those analogs, variants, mutants, alleles, parts and fragments of the target that contain one or more antigenic determinants or epitopes that are essentially the same as the antigenic determinant or epitope to which the sdAbs of the invention bind in the wild-type target. The sdAbs of the invention may bind to such analogs, variants, mutants, alleles, parts and fragments with an affinity and/or specificity that is the same as, or that is higher than or lower than the affinity and specificity with which the sdAbs of the invention bind to the wild-type target. It is also contemplated within the scope of the invention that the sdAbs of the invention bind to some analogs, variants, mutants, alleles, parts and fragments of the target but not to others. In addition, the sdAb of the invention may be humanized, and may be monovalent or multivalent, and/or multispecific. Additionally, the sdAbs of the invention can bind to the phosphorylated form of the target protein as well as the unphosphorylated form of the target protein. sdAbs can be linked to other molecules such as albumin or other macromolecules.

In addition, it is within the scope of the invention that the sdAbs are multivalent, that is, the sdAb can have two or more proteins or polypeptides which are directed against two or more different epitopes of the target. In such a multivalent sdAb, the protein or polypeptide may be directed, for example, against the same epitopes, substantially equivalent epitopes, or different epitopes. The different epitopes may be located on the same target, or it could be on two or more different targets.

It is also contemplated that the sequence of one or more sdAbs of the invention may be connected or joined with one or more linker sequences. The linker can be, for example, a protein sequence containing a combination of serines, glycines and alanines.

It is also within the scope of the invention to use parts, fragments, analogs, mutants, variants, alleles and/or derivatives of the sdAbs of the invention, as long as these are suitable for the described uses.

Since the sdAbs of the invention are mainly intended for therapeutic and/or diagnostic use, they are directed against mammalian, preferably human, targets. However, it is possible that the sdAbs described herein are cross-reactive with targets from other species, for example with targets from one or more other species of primates or other animals (for example, mouse, rat, rabbit, pig or dog), and in particular in animal models for diseases and disorders associated with the disease associated with the targets.

In another aspect, the invention relates to a nucleic acid that encodes an sdAb of the invention. Such a nucleic acid may be, for example, in the form of a genetic construct.

In another aspect, the invention relates to host or host cell that expresses or is capable of expressing an sdAb of the invention, and/or that contains a nucleic acid encoding a sdAb of the invention. Sequences of the sdAbs can be used to insert into the genome of any organism to create a genetically modified organism (GMO). Examples include, but are not limited to, plants, bacteria, viruses, and animals.

The invention further relates to methods for preparing or generating the sdAbs, nucleic acids encoding the sdAbs, host cells expressing or capable of expressing such sdAbs, products and compositions containing the sdAbs of the invention.

The invention further relates to applications and uses of the sdAb, the nucleic acids encoding the sdAbs, host cells, products and compositions described herein. Such a product or composition may, for example, be a pharmaceutical composition for treatment or prevention of a disease, or a product or composition for diagnostic use. sdAbs can be used in a variety of assays, for example ELISA assays and mass spectrometry assays to measure the serum and tissue levels of the sdAbs.

In another aspect, a nucleic acid encoding one or more sdAb of the invention can be inserted into the genome of an organism to treat or prevent diseases.

The present invention generally relates to sdAbs, as well as to proteins or polypeptides comprising or essentially consisting of one or more of such sdAbs, that can be used for prophylactic, therapeutic and/or diagnostic purposes.

The methods and compositions detailed in the present invention can be used to treat disease described herein, and can be used with any dosage and/or formulation described herein or otherwise known, as well as with any route of administration described herein or otherwise known to one of skill in the art.

The sdAbs of the invention, in particular the anti-STAT3 VHH, the anti-KRAS VHH, and the anti-TNF-alpha VHH of the present invention, can be used for treatment and prevention of malignant diseases including, but not limited to: multiple myeloma, leukemias (HTLV-1 dependent, erythroleukemia, acute myelogenous leukemia (AML), chronic myelogenous leukemia (CML), and large granular lymphocyte leukemia (LGL), lymphomas (EBV-related/Burkitt's, mycosis fungoides, cutaneous T-cell lymphoma, non-Hodgkins lymphoma (NHL), anaplastic large-cell lymphoma (ALCL), breast cancers, triple-negative breast cancers, head and neck cancers, melanoma, ovarian cancers, lung cancers, pancreatic cancers, prostate cancers, sarcomas, osteosarcoma, Kaposi's sarcoma, Ewing's sarcoma, hepatocellular cancers, glioma, neuroblastoma, astrocytoma, colorectal cancers, Wilm's tumors, renal cancers, bladder cancers, endometrial cancers, cervical cancers, esophageal cancers, cutaneous squamous cell cancers, basal cell cancers, and any metastatic cancers. The sdAbs can be used in cancer patients to help prevent or reduce weight loss or cachexia due to cancer.

The sdAb, in particular the anti-STAT3 and the anti-TNF-alpha sdAbs of the present invention, can also be used for treatment and prevention of diseases such as, but not limited to: autoimmune diseases (e.g., rheumatoid arthritis, ulcerative colitis, Crohn's disease, bacterial induced colitis, asthma, scleroderma, lupus, encephalomyelitis, arteritis, vasculitis, glomerulonephritis, uveitis, uveoretinitis, multiple sclerosis), polycystic kidney disease, dermatologic diseases (e.g., psoriasis, alopecia areata, atopic dermatitis, keloids/hypertrophic scars, lipoma, Padget's disease, and actinic keratosis), Hidradenitis suppurativa, transplantation (e.g., solid organ, bone marrow, hand, face, limbs, any body part), muscular dystrophy and muscle wasting associated with cancers and aging, endometriosis, macular degeneration, retinal degeneration, stroke, epilepsy, traumatic brain and spinal cord injuries, hypertension, cardiac hypertrophy, Alzheimer's disease, pulmonary artery hypertension, type 2 diabetes mellitus, and ankylosing spondylitis. Additionally sdAbs can target orphan diseases. Examples of these rare orphan diseases include, but are not limited to, triple negative breast cancers, pancreatic cancers, AML (acute myeloid leukemia), head and neck cancers, multiple myeloma, and chemo-resistant cancers.

Viral infections can be treated by targeting intracellular viral proteins in infected cells. Viral proteins, such as HIV reverse transcriptase, can block viral life-cycle. The sdAb of the invention can also target intracellular viral proteins such as Ebola VP24 and thus block Ebola's ability to shut down the host's anti-viral immune response. The sdAbs of the invention can be used to target diseases when there is an overexpression of an intracellular molecule. Huntington's disease can be treated with sdAbs.

The sdAbs of the invention can be used with one or more compounds. For example, the sdAb of the invention can be used with JAK/STAT inhibitors such as, for example, Curcumin, Resveratrol, Cucurbitacin A, B, E, I, Q, Flavopiridol, Deoxytetrangomycin, Cyclopentenone derivatives, N-Acyl-homoserine Lactone, Indirubin derivatives, Meisoindigo, Tyrphostins, Platinum-containing compounds (e.g., IS3-295), Peptidomimetics, antisense oligonucleotides, S3I-201, phosphotyrosin tripeptide derivatives, HIV protease inhibitors (e.g., nelfinavir, indinavir, saquinavir, & ritornavir), JSI-124, XpYL, Ac-pYLPQTV-NH2, ISS 610, CJ-1383, pyrimethamine, Metformin, Atiprimod, S3I-M2001, STX-0119; N-[2-(1,3,4-oxadiazolyl)]-4 quinolinecarboxamide derivative, S3I-1757, LYS; 5,8-dioxo-6(pyridin-3-ylamino)-5,8,-dihydro-naphthalene-1-sulfonamide, withacinstin, Stattic, STA-21, LLL-3, LLL12, XZH-5, SF-1066, SF-1087, 17o, Cryptotanshinone, FLL32, FLL62, C188-9, BP-1108 and BP-1075, Galiellalactone, JQ1, 5, 15 DPP, WP1066, Niclosamide, SD1008, Nifuroxazide, Cryptotanshinone, BBI quinone, and Ruxolitnib Phosphate. The one or more compounds can increase the therapeutic response and augment the effectiveness of the sdAb of the invention. In addition, the effectiveness of the sdAb can be increased by combining it with peptides, peptidomimetics, and other drugs, such as, for example, but not limited to, cimetidine, atorvastatin, celecoxib, metformin, and cimetidine. In addition, anti-STAT3 sdAbs can convert radioresistant cancers to radiosensitive cancers with respect to radiation therapy.

It is also contemplated that one or more sdAbs of the invention can be combined, or the sdAbs of the invention can be combined with other sdAbs.

It is contemplated that certain sdAbs of the invention can cross the cell membrane and enter the cell without the aid of additional targeting protein sequences on the sdAb, and without the aid of exogenous compounds that direct the sdAb to bind to the cell surface receptors and cross the cell membrane.

After crossing the cell membrane, these sdAbs can target transmembrane or intracellular molecules or antigens. These intracellular or transmembrane targets can be, for example, proteins, carbohydrates, lipids, nucleic acids, mutated proteins, viral proteins, and prions. The sdAb targets may function as enzymes, structural proteins of the cell, intracellular portions of cell membrane molecules, molecules within the membranes of organelles, any type of RNA molecule, any regions of DNA or chromosome, methylated or unmethylated nucleic acids, partially assembled molecules within the synthesis mechanism of the cell, second messenger molecules, and molecules within cell signaling mechanisms. Targets may include all molecules in the cytoplasm, nucleus, organelles, and cell membrane. Molecules destined for secretion or placement in the cell membrane can be targeted within the cytoplasm before leaving the cell.

The sdAb targets can be in humans, animals, plants, fungi, parasites, protists, bacteria, viruses, prions, prokaryotic cells, and eukaryotic cells. Some examples of inter- and intracellular signaling molecules and protein groups that can be targeted by the sdAbs of the invention are: oncogene products, hormones, cytokines, growth factors, neurotransmitters, kinases (including tyrosine kinase, serine kinase, and threonine kinase), phosphatases, ubiquitin, cyclic nucleotides, cyclases (adenylyl and guanylyl), G proteins, phosphodiesterases, GTPase superfamily, immunoglobulins (antibodies, Fab fragments, binders, sdAbs), immunoglobulin superfamily, inositol phosphate lipids, steroid receptors, calmodulin, CD group (e.g., CD4, CD8, CD28, etc.), transcription factors, TGF-beta, TNF-alpha and beta, TNF ligand superfamily, notch receptor signaling molecules, hedgehog receptor signaling molecules, Wnt receptor signaling molecules, toll-like receptor signaling molecules, caspases, actin, myosin, myostatin, 12-lipoxygenase, 15-lipoxygenase, lipoxygenase superfamily, reverse transcriptase, viruses and their proteins, amyloid proteins, collagen, G protein coupled receptors, mutated normal proteins, prions, Ras, Raf, Myc, Src, BCR/ABL, MEK, Erk, Mos, Tp12, MLK3, TAK, DLK, MKK, p38, MAPK, MEKK, ASK, SAPK, JNK, BMK, MAP, JAK, PI3K, cyclooxygenase, STAT1, STAT2, STAT3, STAT4, STAT5a, STAT5b, STAT6, Myc, p53, BRAF, NRAS, KRAS, HRAS and chemokines.

KRAS is a Kirsten ras oncogene homolog from the mammalian ras gene family. KRAS encodes a protein that is a member of the small GTPase superfamily. The protein is implicated in various malignancies, including lung adenocarcinoma, mucinous adenoma, ductal carcinoma of the pancreas, and colorectal carcinoma. Under normal conditions, Ras family members influence cell growth and differentiation events in a subcellular membrane compartmentalization-based signaling system. However, oncogenic Ras can deregulate processes that control both cell proliferation and apoptosis.

Anti-KRAS sdAbs were developed to target wild-type and mutated KRAS (G12D) in order to disrupt its role in malignant cells such as, for example, cells involved in colorectal cancer, pancreatic cancer, biliary tract cancer, lung cancer, leukemias, and other metastatic malignancies. Without being bound by a particular mechanism, it is thought that the anti-KRAS sdAb binds KRAS and blocks the downstream signaling of KRAS in malignant cells. Additionally, the anti-KRAS sdAb may successfully treat malignancies that are resistant to anti-EGFR biologics (e.g., cetuximab and panitumumab).

Using methods that are well-known in the art, recombinant human mutant KRAS (G12D) protein was used to generate sdAbs that are directed against or can bind to an epitope of KRAS or mutant KRAS (G12D), or other KRAS mutants. Additionally, sdAbs can be generated to other KRAS mutants. To generate the anti-KRAS sdAbs, recombinant full-length human KRAS (Gene ID: 3845) was expressed in *Escherichia coli*.

Several sdAbs were obtained and screened. The DNA sequence of one anti-KRAS (G12D) sdAb, named KRAS_13 (SEQ ID NO:1), is shown below:

```
5'Gaggtgcagctggtggagtctgggggaggctcggtgcagactggaggg tctctgagactctcctgtgcagtttctggaaatatcggcagcagctactg catgggctggttccgccaggctccagggaagaagcgcgaggcggtcgcac gtattgtacgtgatggtgccactggctacgcagactacgtgaagggccga ttcaccatctcccgagacagcgccaagaacactctgtatctgcaaatgaa caggctgatacctgaggacactgccatctactactgtgcggcagacctgc ccccaggttgtttgactcaggcgatttggaattttggttatcggggccag ggaaccctggtcaccgtctcctca-3'
```

The amino acid sequence of the anti-KRAS (G12D) sdAb (SEQ ID NO. 2), KRAS_13, is shown below, with the CDRs underlined:

```
EVQLVESGGGSVQTGGSLRLSCAVSGNIGSSYCMGWFRQAPGKKREAVAR

IVRDGATGYADYVKGRFTISRDSAKNTLYLQMNRLIPEDTAIYYCAADLP

PGCLTQAIWNFGYRGQGTLVTVSS
```

Additionally, the present invention comprises one or more mouse monoclonal antibodies which are directed against one or more domains of the anti-KRAS sdAb of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA or mass spectrometry assay in order to measure the amount of anti-KRAS sdAb present in a patient's serum. The cytotoxicity of KRAS (G12D) sdAbs on PANC-1 human pancreatic cancer cells was tested, as described below.

STAT3 is a member of the signal transducers and activators of transcription (STAT) family of proteins that carry both signal transduction and activation of transcription functions. STAT3 is widely expressed and becomes activated through phosphorylation on tyrosine and/or serine as a DNA binding protein in response to a various cytokines and growth factors such as EGF, IL-6, PDGF, IL-2 and G-CSF. The STAT3 phosphoprotein forms homodimers and heterodimers with other members of the STAT family and translocates to the nucleus in order to modulate the transcription of various genes, and as a result plays a key role in many cellular processes such as cell growth, apoptosis, angiogenesis, immune evasion, and survival.

An anti-STAT3 sdAb can be given to patients and other organisms to treat diseases caused by phosphorylated and non-phosphorylated STAT3, as well as to prevent the development of disease or recurrence of disease. For example, patients who have undergone organ transplant and bone marrow transplant are at higher risk for cutaneous SCCA and BCCA due to the immunosuppressive medications they take. Administration of an anti-STAT3 sdAb can reduce or eliminate this risk. Patients treated for a malignancy who are at risk for recurrence will benefit from treatment with the anti-STAT3 sdAb. Based on family medical history and HLA-type, some individuals will be at increased risk for some types of autoimmune diseases and may benefit from treatment with sdAbs to reduce risk of developing that autoimmune disease. Breast cancer risk can be reduced with administration of anti-STAT3 medication such as GLG-302, as demonstrated in a recent NCI study.

In addition to inhibiting STAT3, the anti-STAT3 sdAb can also inhibit STAT1, STAT2, STAT4, STAT5a, STAT5b, and STAT6 due to the high degree of homology between these molecules.

Figure 1:
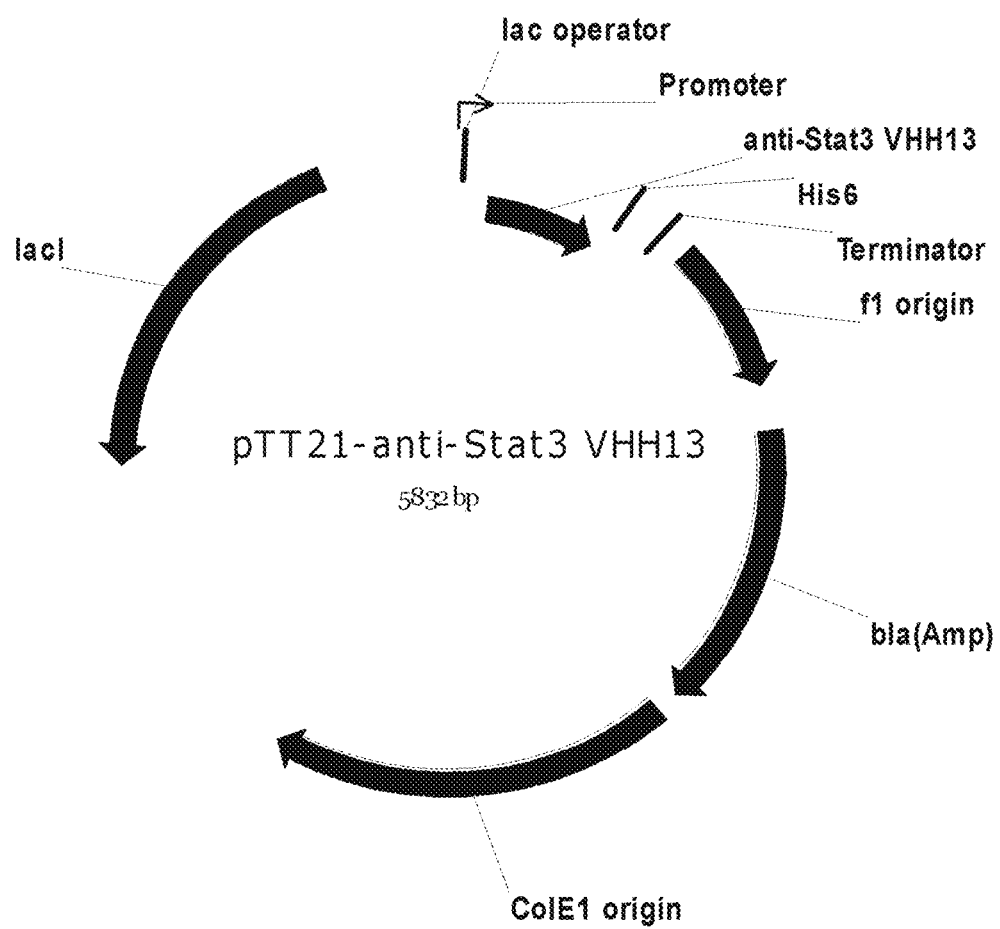
FIG. 1 is a schematic map of VHH13 anti-STAT3 sdAb expression vector pTT21-stt VHH13.
Figure 2:
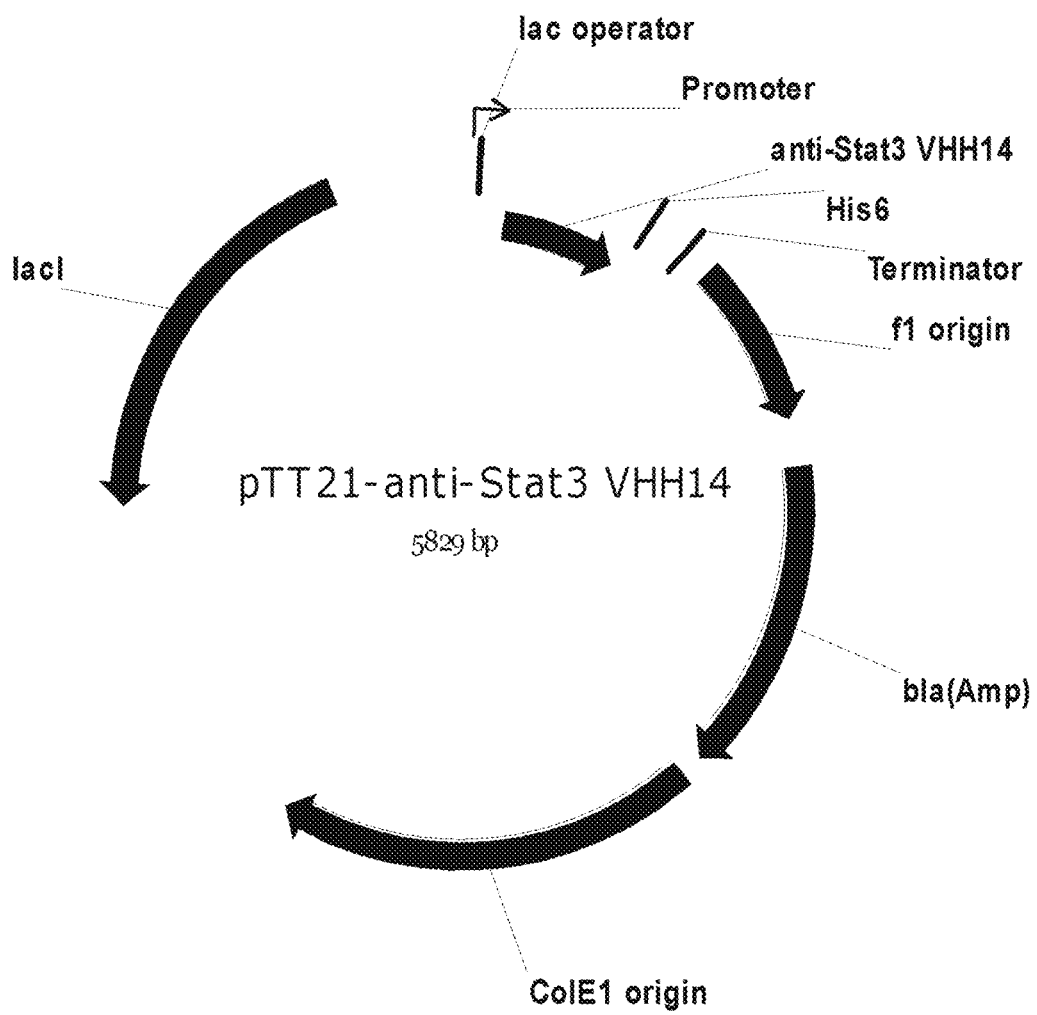
FIG. 2 is a schematic map of VHH14 anti-STAT3 sdAb expression vector pTT21-stt VHH14.

Recombinant human STAT3 protein was used to produce anti-STAT sdAbs that were directed against or can bind to an epitope of STAT3. To generate the anti-STAT3 sdAbs, recombinant full-length human STAT3 (Gene ID: 6774) was expressed by baculovirus in Sf9 insect cells. The anti-STAT sdAbs were cloned into vectors that can be expressed in both bacterial and mammalian cells, as shown in FIGS. 1 and 2.

The anti-STAT3 sdAb of the invention can be used to target STAT3 and all other STAT molecules inside the cell in order to inhibit cell growth, such as, for example, suppression of cancer cell growth. In addition, the anti-STAT3 sdAb can inhibit cell growth in other proliferative diseases such as psoriasis and macular degeneration via VEGF.

Without being limited to a particular mechanism of action, it is thought that anti-STAT3 sdAb can eliminate cancer induced immune suppression by decreasing STAT3 levels in antigen presenting cells such as, for example, host dendritic cells. STAT3 inhibition promotes anti-cancer response by patient's innate and adaptive immune systems (i.e., dendritic cells, macrophages, neutrophils, T cells, NK cells, and B cells).

Using methods that are well known in the art, several anti-STAT sdAbs were obtained and screened for the ability to suppress cancer cell growth and induce apoptosis in cancer cell lines, as described below. The cytotoxicity and anti-proliferative activities of the anti-STAT3 sdAbs was tested. In addition, the tolerance of anti-STAT3 sdAbs was tested in vitro and in vivo. The production of mouse monoclononal antibody directed against one or more domains of the anti-STAT sdAbs is described below.

The amino acid sequence of one anti-STAT3 sdAb, named VHH13 (SEQ ID NO. 3), is shown below:

HVQLVESGGGSVQAGGSLRLSCAASGANGG<u>RSCMG</u>WFRQVPGKEREGVS<u>G

ISTGGLITYYADSVKGRFT</u>ISQDNTKNTLYLQMNSLKPEDTAMYYCAT<u>SR

FDCYRGSWFNRYMYNSW</u>GQGTQVTVSS

The three CDRs are underlined.

The amino acid sequence of a second anti-STAT3 sdAb, named VHH14 (SEQ ID NO. 4), is shown below:

QVQLVESGGGSVQAGGSLRLSCVASTY<u>TGCMG</u>WFRQAPGKEREGVA<u>A

LSSRGFAGHYTDSVKGRFS</u>ISRDYVKNAVYLQMNTVKPEDAAMYYCAA<u>RE

GWECGETWLDRTAGGHTYW</u>GQGTLVTVSS

Again, the three CDRs are underlined. The protein sequences of other anti-STAT3 sdAbs that were obtained are as follows:

```
STAT3_10 (SEQ ID NO. 5):
(1) DVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
     CAARE

(98) GWECGETWLDRTAGGHTYWGQGTQVTVSS

STAT3_34 (SEQ ID NO. 6):
(1) DVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
     CAARE

(98) GWECGETWLDRTAGGHTYWGQGTQVTVSS

STAT3_19 (SEQ ID NO. 7):
(1) HVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
     CAARE

(98) GWECGETWLDRTAGGHTYWGQGTQVTVSS

STAT3_14 (SEQ ID NO. 8):
(1) QVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
     CAARE

(98) GWECGETWLDRTAGGHTYWGQGTLVTVSS

STAT3_35 (SEQ ID NO. 9):
(1) QVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
     CAARE

(98) GWECGETWLDRTAGGHTYWGQGTLVTVSS

STAT3_9 (SEQ ID NO. 10):
(1) QVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
     CAARE

(98) GWECGETWLDRTAGGHTYWGQGTLVTVSS

STAT3_30 (SEQ ID NO. 11):
(1) QVQLVESGGGSVQAGGSLRLSCVASTYTGCMGWFRQAPGKEREGVA
    A
```

(48) LSSRGFAGHYTDSVKGRFSISRDYVKNAVYLQMNTVKPEDAAMYY
    CAARE

(98) GWECGETWLDRTAGGHTYWGQGTLVTVSS

STAT3_23 (SEQ ID NO. 12):
(1) QVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
    CAARE

(98) GWECGETWLDRTAGSHTYWGQGTLVTVSS

STAT3_24 (SEQ ID NO. 13):
(1) EVQLVESGGGSVQAGGSLRLSCVASTYTGCMGWFRQAPGKEREGVA
    A

(48) LSSRGFAGHYTDSVKGRFSISRDYVKNAVYLQMNTVKPEDAAMYY
    CAARE

(98) GWECGETWLDRTAGGHTYWGQGTLVTVSS

STAT3_36 (SEQ ID NO. 14):
(1) DVQLVESGGGSVQAGDSLRLSCVASTYTGCMGWFRQAPGKEREGVA
    A

(48) LSSRGFAGHYTDSVKGRFSISRDYVKNAVYLQMNTVKPEDAAMYY
    CAARE

(98) GWECGETWLDRTAGGHTYWGQGTLVTVSS

STAT3_12 (SEQ ID NO. 15):
(1) QVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTLVTVSS

STAT3_16 (SEQ ID NO. 16):
(1) QVQLVESGGGSVQAGGSLRLSCAASGANGGRSCMGWFRQVPGKERE
    GVSG

(51) ISTGGLITYYADSVKGRFTISQDNTNNTLYLQMNSLKPEDTAMYY
    CATSR (101) FDCYRGSWFNRYMYNSWGQGTLVTVSS

STAT3_11 (SEQ ID NO. 17):
(1) EVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTLVTVSS

STAT3_20 (SEQ ID NO. 18):
(1) DVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTLVTVSS

STAT3_2 (SEQ ID NO. 19):
(1) DVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTLVTVSS

STAT3_15 (SEQ ID NO. 20):
(1) DVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTLVTVSS

STAT3_6 (SEQ ID NO. 21):
(1) HVQLVESEGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTLVTVSS

STAT3_33 (SEQ ID NO. 22):
(1) QVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTQVTVSS

STAT3_17 (SEQ ID NO. 23):
(1) QVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTQVTVSS

STAT3_25 (SEQ ID NO. 24):
(1) EVQLVESGGGSVQAGGSLRLSCAASGANGGRSCMGWFRQVPGKERE
    GVSG

(51) ISTGGLITYYADSVKGRFTISQDNTKNTLYLQMSSLKPEDTAMYY
    CATSR (101) FDCYRGSWFNRYMYNSWGQGTQVTVSS

STAT3_32 (SEQ ID NO. 25):
(1) DVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTQVTVSS

STAT3_13 (SEQ ID NO. 26):
(1) HVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTQVTVSS

STAT3_39 (SEQ ID NO. 27):
(1) HVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTQVTVSS

STAT3_4 (SEQ ID NO. 28):
(1) HVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
    CATSR (101) FDCYRGSWFNRYMYNSWGQGTQVTVSS

STAT3_29 (SEQ ID NO. 29):
(1) HVQLVESGGGSVQAGGSLRLSCAASGANGGRSCMGWFRQVPGKERE
    GVSG

(51) ISTGGLITYYADSVKGRFTISQDNTKNTLYLQMNSLKPEDTAMYY
CATSR (101) FDCYRGSWFNRYMYNSWGQGTQVTVSS

The corresponding anti-STAT3 DNA sequences are as follows:

Stat3_VHH-10 (SEQ ID NO. 30):
5'-gatgtgcagctggtggagtctgggggaggctcggtgcaggctggagg
ctctctgagactctcctgtgtagcctctacatacaccggctgcatgggct
ggttccgccaggctcctggaaaggagcgcgagggagtcgcagctcttagt
agccgtggttttgccgggcactataccgactccgtgaagggccgattctc
catctcccgagactacgtcaagaatgcggtgtatctgcaaatgaacactg
tgaaacctgaggacgctgccatgtactactgtgcagcacgggagggatgg
gagtgcggtgagacctggttggaccggaccgccggggccatacctactg
gggccaggggaccctggtcaccgtctcctca-3'

Stat3_VHH-14 (SEQ ID NO. 31):
5'-caggtgcagctggtggagtctgggggaggctcggtgcaggctggagg
ctctctgagactctcctgtgtagcctctacatacaccggctgcatgggct
ggttccgccaggctcctggaaaggagcgcgagggagtcgcagctcttagt
agccgtggttttgccgggcactataccgactccgtgaagggccgattctc
catctcccgagactacgtcaagaatgcggtgtatctgcaaatgaacactg
tgaaacctgaggacgctgccatgtactactgtgcagcacgggagggatgg
gagtgcggtgagacctggttggaccggaccgccggggccatacctactg
gggccaggggaccctggtcaccgtctcctca-3'

Stat3_VHH-12 (SEQ ID NO. 32):
5'-caggtgcagctggtggagtctgggggaggctcggtgcaggctggagg
gtctctgagactctcctgtgcagcctctggagccaatggtggtcggagct
gcatgggctggttccgccaggttccagggaaggagcgcgagggggtttct
ggtatttcaaccggtggtcttattacatactatgccgactccgtgaaggg
ccgattcaccatctcccaagacaacaccaagaacacgctgtatctgcaaa
tgaacagcctgaaacctgaggacactgccatgtactactgtgcgacgagt
cggtttgactgctatagaggctcttggttcaaccgatatatgtataacag
ttggggccaggggaccctggtcaccgtctcctca-3'

Stat3_VHH-13 (SEQ ID NO. 33):
5'-catgtgcagctggtggagtctgggggaggctcggtgcaggctggagg
gtctctgagactctcctgtgcagcctctggagccaacggtggtcggagct
gcatgggctggttccgccaggttccagggaaggagcgcgagggggtttct
ggtatttcaaccggtggtcttattacatactatgccgactccgtgaaggg
ccgattcaccatctcccaagacaacaccaagaacacgctgtatctgcaaa
tgaacagcctgaaacctgaggacactgccatgtactactgtgcgacgagt
cggtttgactgctatagaggctcttggttcaaccgatatatgtataacag
ttggggccaggggaccctggtcactgtctcctca-3'

Stat3_VHH-20 (SEQ ID NO. 34):
5'-gatgtgcagctggtggagtctgggggaggctcggtgcaggctggagg
gtctctgagactctcctgtgcagcctctggagccaatggtggtcggagct
gcatgggctggttccgccaggttccagggaaggagcgcgagggggtttct
ggtatttcaaccggtggtcttattacatactatgccgactccgtgaaggg
ccgattcaccatctcccaagacaacaccaagaacacgctgtatctgcaaa
tgaacagcctgaaacctgaggacactgccatgtactactgtgcgacgagt
cggtttgactgctatagaggctcttggttcaaccgatatatgtataacag
ttggggccaggggaccctggtcaccgtctcctca-3'

Stat3_VHH-23 (SEQ ID NO. 35):
5'-caggtgcagctggtggagtctgggggaggctcggtgcaggctggagg
ctctctgagactctcctgtgtagcctctacatacaccggctgcatgggct
ggttccgccaggctcctggaaaggagcgcgagggagtcgcagctcttagc
agccgtggttttgccgggcactataccgactccgtgaagggccgattctc
catctcccgagactacgtcaagaatgcggtgtatctgcaaatgaacactg
tgaaacctgaggacgctgccatgtactactgtgcagcacgggagggatgg
gagtgcggtgagacctggttggaccggaccgccgggagccatacctactg
gggccaggggaccctggtcaccgtctcctca-3'

Stat3_VHH-24 (SEQ ID NO. 36):
5'-gaggtgcagctggtggagtctgggggaggctcggtgcaggctggagg
ctctctgagactctcctgtgtagcctctacatacaccggctgcatgggct
ggttccgccaggctcctggaaaggagcgcgagggagtcgcagctcttagt
agccgtggttttgccgggcactataccgactccgtgaagggccgattctc
catctcccgagactacgtcaagaatgcggtgtatctgcaaatgaacactg
tgaaacctgaggacgctgccatgtactactgtgcagcacgggagggatgg
gagtgcggtgagacctggttggaccgaaccgccggggccatacctactg
gggccaggggaccctggtcaccgtctcctca-3'

Stat3_VHH-25 (SEQ ID NO. 37):
5'-gaggtgcagctggtggagtctgggggaggctcggtgcaggctggagg
gtctctgagactctcctgtgcagcctctggagccaatggtggtcggagct
gcatgggctggttccgccaggttccagggaaggagcgcgagggggtttct
ggtatttcaaccggtggtcttattacatactatgccgactccgtgaaggg
tcgattcaccatctcccaagacaacaccaagaacacgctgtatctgcaaa
tgagcagcctgaaacctgaggacactgccatgtactactgtgcgacgagt
cggtttgactgctatagaggctcttggttcaaccgatatatgtataacag
ttggggccaggggaccctggtcaccgtctcctca-3'

Stat3_VHH-19 (SEQ ID NO. 38):
5'-catgtgcagctggtggagtctggggggggctcggtgcaggctggagg
ctctctgagactctcctgtgtagcctctacatacaccggctgcatgggct
ggttccgccaggctcctggaaaggagcgcgagggagtcgcagctcttagt
agccgtggttttgccgggcactataccgactccgtgaagggccgattctc
catctcccgagactacgtcaagaatgcggtgtatctgcaaatgaacactg
tgaaacctgaggacgctgccatgtactactgtgcagcacgggagggatgg -continued Stat3_VHH-32 (SEQ ID NO. 39):
5'-gatgtgcagctggtggagtctgggggaggctcggtgcaggctggagg gtctctgagactctcctgtgcagcctctggagccaatggtggtcggagct gcatgggctggttccgccaggttccagggaaggagcgcgaggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggacccaggtcaccgtctcctca-3'

Stat3_VHH-33 (SEQ ID NO. 40):
5'-caggtgcagctggtggagtctgggggaggctcggtgcaggctggagg gtctctgagactctcctgtgcagcctctggagccaatggtggtcggagct gcatgggctggttccgccaggttccagggaaggagcgcgaggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggacccaggtcaccgtctcctca-3'

Stat3_VHH-36 (SEQ ID NO. 41):
5'-gatgtgcagctggtggagtctgggggaggctcggtgcaggctggaga ctctctgagactctcctgtgtagcctctacatacaccggctgcatgggct ggttccgccaggctcctggaaaggagcgcgagggagtcgcagctcttagt agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg gagtgcggtgagacctggttggaccggaccgccgggggccatacctactg gggccaggggaccctggtcactgtctcctca-3'

Stat3_VHH-11 (SEQ ID NO. 42):
5'-gtgcagctggtggagtctgggggaggctcggtgcaggctggagggtc tctgagactctcctgtgcagcctctggagccaatggtggtcggagctgca tgggctggttccgccaggttccagggaaggagcgtgaggggtttctggt atttcaaccggtggtcttattacatactatgccgactccgtgaagggccg attcaccatctcccaagacaacaccaagaacacgctgtatctgcaaatga acagcctgaaacctgaggacactgccatgtactactgtgcgacgagtcgg tttgactgctatagaggctcttggttcaaccgatatatgtataacagttg gggccaggggaccctggtcactgtctcctca-3'

Stat3_VHH-6 (SEQ ID NO. 43):
5'-gtgcagctggtggagtctgagggaggctcggtgcaggctggagggtc tctgagactctcctgtgcagcctctggagccaatggtggtcggagctgca tgggctggttccgccaggttccagggaaggagcgcgagggggtttctggt atttcaaccggtggtcttattacatactatgccgactccgtgaagggccg attcaccatctcccaagacaacaccaagaacacgctgtatctgcaaatga acagcctgaaacctgaggacactgccatgtactactgtgcgacgagtcgg tttgactgctatagaggctcttggttcaaccgatatatgtataacagttg gggccaggggaccctggtcaccgtctcctca-3'

Stat3_VHH-1 (SEQ ID NO. 44):
5'-gtgcagctggtggagtctgggggaggctcggtgcaggctggagggtc tctgagactctcctgtgcagcctctggagccaatggtggtcggagctgca tgggctggttccgccaggttccagggaaggagcgcgagggggtttctggt atttcaaccggtggtcttattacatactatgccgactccgtgaagggccg attcaccatctcccaagacaacaccaataacacgctgtatctgcaaatga acagcctgaaacctgaggacactgccatgtactactgtgcgacgagtcgg tttgactgctatagaggctcttggttcaaccgatatatgtataacagttg gggccaggggaccctggtcactgtctcctca-3'

Additionally, the present invention comprises one or more mouse monoclonal antibodies which are directed against one or more domains of the anti-STAT3 sdAb of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA in order to measure the amount of anti-STAT3 sdAb present in a patient's serum. It should be appreciated that the method is not limited to anti-STAT3 sdAbs, and could be used to produce a mouse antibody directed towards any of the sdAbs of the present invention.

The TNF-alpha gene encodes a multifunctional proinflammatory cytokine that belongs to the tumor necrosis factor (TNF) superfamily. This cytokine is mainly secreted by macrophages. The cytokine is involved in the regulation of a wide spectrum of biological processes including growth regulation, differentiation, inflammation, viral replication, tumorigenesis, and autoimmune diseases; and in viral, bacterial, fungal, and parasitic infections. Besides inducing hemorrhagic necrosis of tumors, TNF was found to be involved in tumorigenesis, tumor metastasis, viral replication, septic shock, fever, inflammation, cachexia, and autoimmune diseases including Crohn's disease, and rheumatoid arthritis as well as graft-versus-host disease.

The present invention provides sdAbs, proteins, and polypeptides that are directed against TNF-alpha, in particular against human TNF-alpha inside the cell or cell membrane, so as to prevent the secretion of TNF-alpha by cells.

It is contemplated that the anti-TNF-alpha sdAbs and polypeptides of the invention can be used for the prevention and/or treatment of diseases and disorders associated with and/or mediated by TNF-alpha, such as inflammation, rheumatoid arthritis, Crohn's disease, ulcerative colitis, inflammatory bowel syndrome, multiple sclerosis, Addison's disease, autoimmune hepatitis, autoimmune parotitis, diabetes type 1, epididymitis, glomerulonephritis, Graves' disease, Guillain-Barre syndrome, Hashimoto's disease, hemolytic anemia, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, vasculitis, and weight loss due to cancer and cachexia.

TNF-alpha exists in different forms; there are monomeric and multimeric forms, including a trimeric form. It is within the scope of the invention that the sdAbs, proteins and polypeptides of the invention bind to TNF-alpha in its different form, i.e., monomeric form or multimeric forms. Thus, when sdAbs, proteins and polypeptides of the invention are directed to TNF-alpha, it should be understood that this also comprises sdAbs, proteins and polypeptides directed against TNF-alpha in its trimeric form.

It is known that signal transduction by TNF involves crosslinking by TNF receptors by a trimer of TNF molecules, which contains three receptor binding sites (see, for example, Peppel et al., J. Exp. Med., 174 (1991), 1483-1489).

Recombinant human TNF-alpha protein was used to generate sdAbs that are directed against or can bind to an epitope of TNF-alpha. To generate the anti-TNF-alpha sdAbs, recombinant full-length human TNF-alpha (Gene ID: 7124) was expressed in *Escherichia coli* and used as the target antigen.

Thirty-five sdAbs against the TNF-alpha protein were obtained. These anti-TNF-alpha antibodies were divided into three groups based on sequence homology.

The amino acid sequence of the first anti-TNF-alpha sdAb, named TNF-alpha VHH66 (SEQ ID NO. 45) sdAb, is shown below:

HVQLVESGGGSVEAGGSLRLSCAASGFRYA<u>AYCMG</u>WFRQADGKERE

GVA<u>TIDIDGLTTHAD</u>SVKGRF<u>TI</u>SRDNAKNTLSLQMNDLKPEDTA

MYYCAA<u>DRDRCGSIWTYAYKYRG</u>-QGTLVTVSS

The three CDRs are underlined.

In The amino acid sequence of the second anti-TNF-alpha sdAb, named TNF-alpha VHH69 (SEQ ID NO. 46) sdAb, is shown below:

EVQLVESGGGSVLAGGSLRLSCVASGFTSR<u>YNYMA</u>WFRQAPGKERE

GVA<u>TIGTASGSADYYGSVKDRFTI</u>SQDNAKNTVYLQMNSLKPEDTA

MYYCAA<u>RTYGTISLTPSDYRY</u>WGQGTLVTVSS

The three CDRs are underlined.

The amino acid sequence of the third anti-TNF-alpha sdAb, named TNF-aphha VHH62 (SEQ ID NO. 47) sdAb, is shown below:

QVQLVESGGGPVQAGETLRLSCTASGFTFA<u>EADMG</u>WYRQAPGHECE

LVS<u>TITTEGITSEASSYYADSVRGRFTI</u>SRDNAKNMVYLQMNSLKPEDTA

VYYCAP<u>DPYAYSTYSDYCS</u>WAQGTQGTLVTVSS

The three CDRs are underlined. Other anti-TNF-alpha sdAbs that were found include the sequences below, again with the CDRs underlined:

TNF_2 (SEQ ID NO. 48):
QVQLVESGGGSVEAGRSLRLSCAASGFRYA<u>AYCMG</u>WFRQADGKERE

GVA<u>TIDIDGQTTHAD</u>SVKGRF<u>TI</u>SRDNAKNTLSLQMNDLKPEDTA

MYYCAADRDRCGSIWTYAYKYRGQGTQVTVSS

TNF_46 (SEQ ID NO. 49):
QVQLVESGGGSVEAGGSLRLSCAASGFRYA<u>AYCMG</u>WFRQADGKERE

GVA<u>TIDIDGQTTHAD</u>SVKGRF<u>TI</u>SRDNVKNTLSLQMNDLKPEDTA

MYYCAADRDRCGSIWTYAYKYRGQGTQVTVSS

TNF_71 (SEQ ID NO. 50):
QVQLVESGGGSVEAGGSLRLSCAASGFRYA<u>AYCMG</u>WFRQADGKERE

GVA<u>TIDIDGLTTHAD</u>SVKGRF<u>TI</u>SRDNAKNTLSLQMNDLKPEDTA

MYYCAA<u>DRDRCGSIWTYAYKY</u>RGQGTQVTVSS

TNF_21 (SEQ ID NO. 51):
QVQLVESGGGSVEAGGSLRLSCAASGFRYA<u>AYCMG</u>WFRQADGKERE

GVA<u>TIDIDGQTTHAD</u>SVKGRF<u>TI</u>SRDNAKNTLSLQMNDLKPEDTA

MYYCAA<u>DRDRCGSIWTYAYKY</u>RGQGTQVTVSS

TNF_38 (SEQ ID NO. 52):
EVQLVESGGGSVEAGGSLRLSCAASGFRYA<u>AYCMG</u>WFRQADGKERE

GVA<u>TIDIDGQTTHAD</u>SVKGRF<u>TI</u>SRDNAKNTLSLQMNDLKPEDTA

MYYCAA<u>DRDRCGSIWTYAYKY</u>RGQGTQVTVSS

TNF_18 (SEQ ID NO. 53):
EVQLVESGGGSVEAGGSLRLSCAASGFRYA<u>AYCMG</u>WFRQADGKERE

GVA<u>TIDIDGLTTHAD</u>SVKGRF<u>TI</u>SRDNAKNTLSLQMNDLKPEDTA

MYYCAA<u>DRDRCGSIWTYAYKY</u>RGQGTLVTVSS

TNF_37 (SEQ ID NO. 54):
DVQLVESGGGSVEAGGSLRLSCAASGFRYA<u>AYCMG</u>WFRQADGKERE

GVA<u>TIDIDGQTTHAD</u>SVKGRF<u>TI</u>SRDNAKNTLSLQMNDLKPEDTA

MYYCAA<u>DRDRCGSIWTYAYKY</u>RGQGTLVTVSS

TNF_66 (SEQ ID NO. 55):
HVQLVESGGGSVEAGGSLRLSCAASGFRYA<u>AYCMG</u>WFRQADGKERE

GVA<u>TIDIDGLTTHAD</u>SVKGRF<u>TI</u>SRDNAKNTLSLQMNDLKPEDTA

MYYCAA<u>DRDRCGSIWTYAYKY</u>RGQGTLVTVSS

TNF_68 (SEQ ID NO. 56):
HVQLVESGGGSVEAGGSLRLSCAASGFRYA<u>AYCMG</u>WFRQADGKERE

GVA<u>TIDIDGLATHAD</u>SVKGRF<u>TI</u>SRDNAKNTLSLQMNDLKPEDTA

MYYCAA<u>DRDRCGSIWTYAYKY</u>RGQGTLVTVSS

TNF_78 (SEQ ID NO. 57):
HVQLVESGGGSVEAGGSLRLSCAASGFRYA<u>AYCMG</u>WFRQADRKERE

GVA<u>TIDIDGQTTHAD</u>SVKGRF<u>TI</u>SRDNAKNTLSLQMNDLKPEDTA

MYYCAA<u>DRDRCGSIWTYAYKY</u>RGQGTQVTVSS

TNF_67 (SEQ ID NO. 58):
HVQLVESGGGSVQAGGSLRLSCAASGFRYA<u>AYCMG</u>WFRQADGKVRE

GVA<u>TIDIDGQTTHAD</u>SVKGRF<u>TI</u>SRDNAKNTLSLQMNDLKPEDTA

MYYCAA<u>DRDRCGSIWTYAYKY</u>RGQGTLVTVSS

TNF_6 (SEQ ID NO. 59):
QVQLVESGGGSVQAGGSLRLSCAASGFIDS<u>FGVMA</u>WFRQAPGKERE

GVA<u>AVYRRAGDTYYADSVKGRFTI</u>SRDNAKNTVYLQMNSLKPEDSA

MYYCAA<u>RTYGSVSSWTGYKY</u>WGQGTQVTVSS

TNF_7 (SEQ ID NO. 60):
DVQLVESGGGSVQAGGSLRLSCAASGFIDSFGVMAWFRQTPGKERE

GVAAVYRRAGDTYYADSVKGRFTISRDNAKNTVYLQMNSLKPEDSA

MYYCAARTYGSVSSWTGYKYWGQGTQVTVSS

TNF_13 (SEQ ID NO. 61):
DVQLVESGGGSVQVGGSLTLSCAVSGYTDSYGVMAWFRQAPGKERE

GVASIYRNSGITYYPDSVKGRFTISRDNAKNTVLLQMNSLKPEDSA

TYYCAVRSFGSVSTWAGYVYWGQGTQVTVSS

TNF_60 (SEQ ID NO. 62):
DVQLVESGGGSVQAGGSLRLSCAASGFIDSFGVMAWFRQAPGKERE

GVAAVYRRAGDTYYADSVKGRFTISRDNAKNTVYLQMNSLKPEDSA

MYYCAARTYGSVSSWTGYKYWGRGTQVTVSS

TNF_73 (SEQ ID NO. 63):
DVQLVESGGGSVRAGGSLRLSCTASGDTSKSDCMAWFRQAPGKERE

RVGAIYTRNGYTHYADSVNGRFTISQDNAKNALYLQMSGLKPEDTA

MYYCAARFRIYGQCVEDDDIDYWGQGTLVTVSS

TNF_69 (SEQ ID NO. 64):
EVQLVESGGGSVLAGGSLRLSCVASGFTSRYNYMAWFRQAPGKERE

GVATIGTASGSADYYGSVKDRFTISQDNAKNTVYLQMNSLKPEDTA

MYYCAARTYGTISLTPSDYRYWGQGTLVTVSS

TNF_76 (SEQ ID NO. 65):
QVQVVEYGGGSVQAGETVRLSCTASGFTFAEADMGWYRQAPGHEWE

LVSNITTEGITSEASSYADSVRGRFTIFDNAKNMVYLQMNSLKHEDTA

VYYCAPDPYAYSTYREYCTWAQGTQGTLVTVSS

TNF_62 (SEQ ID NO. 66):
QVQLVESGGGPVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCSWAQGTQGTLVTVSS

TNF_43 (SEQ ID NO. 67):
QVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTLVTVSS

TNF_15 (SEQ ID NO. 68):
QVQPVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGAQGTLVTVSS

TNF_11 (SEQ ID NO. 69):
QVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCSWAQGTQGTLVTVSS

TNF_17 (SEQ ID NO. 70):
QVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTLVTVSS

TNF_63 (SEQ ID NO. 71):
QVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTLVTVSS

TNF_20 (SEQ ID NO. 72):
HVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTQVTVSS

TNF_58 (SEQ ID NO. 73):
EVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGALVTVSS

TNF_27 (SEQ ID NO. 74):
EVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTLVTVSS

TNF_28 (SEQ ID NO. 75):
EVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCSWAQGTQGTQVTVSS

TNF_4 (SEQ ID NO. 76):
EVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTQVTVSS

TNF_14 (SEQ ID NO. 77):
DVQLVESRGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTLVTVSS

TNF_3 (SEQ ID NO. 78):
DVQLVESGGGSVQAGETLRLSCTASGFTFAEADMGWYRQAPGHVCE

LVSTITTEGITSEASSYYADSVRGRFTISRDNAKNMVYLQMNSLKPEDTA

VYYCAPDPYAYSTYSDYCSWAQGTQGTQVTVSS

TNF_1 (SEQ ID NO. 79):
DVQLVESGGGSVQAGETLRLSCTASGFTFAEADMGWYRQAPGLECE

LVSTITTEGITSEASSYADSVRGRFTISRDNAKNMVYLQMNSLKPEDTA

VYYCAPDPYAYSTYSEYCTWAQGTQGTLVTVSS

TNF_45 (SEQ ID NO. 80):
DVQLVESGGGSVQAGETLRLSCTASGFTFAEADMGWYRQAPGHECE

LVSTITTEGITSEASSYYADSVRGRFTISRDNAKNMVYLQMNSLKPEDTA

VYYCAPDPYAYSTYSDYCTWAQGTQGTLVTVSS

TNF_22 (SEQ ID NO. 81):
DVQLVESGGGSVQAGETLRLSCTASGFTFAEADMGWYRQAPGHECE

LVSTITTEGITSVASSYYADSVRGRFTISRDNAKNMVYLQMNSLKPEDTA

VYYCAPDPYAYSTYSDYCTWAQGTQGTQVTVSS

The in vitro growth inhibition of several TNF-alpha sdAbs was tested, as described below. Additionally, the present invention comprises one or more mouse monoclonal antibodies which are directed against one or more domains of the anti-TNF-alpha sdAb of the invention. The mouse monoclonal antibody can be generated by methods that are known by one of skill in the art, as described above. The mouse monoclonal antibody can be used in diagnostic assays, such as, for example, an immunoassay such as an ELISA in order to measure the amount of anti-TNF-alpha sdAb present in a patient's serum.

The RAF proteins are a family of serine/threonine-specific kinases that serve as a central intermediate in transmitting extracellular signals to the mitogen-activated protein kinase cascade, which controls cell growth, differentiation and survival. BRAF is a member of the RAF family that is activated by members of the Ras family upon growth factor-induced stimulation. Active Ras can induce heterodimerization of cRaf and BRAF and this may explain the observed cooperativity of cRaf and BRaf in cells responding to growth factor signals. Activating mutations in the BRAF gene are present in a large percentage of human malignant melanomas and in a proportion of colon cancers. The vast majority of these mutations result in a valine to glutamic acid change at residue 599 within the activation segment of BRAF.

Anti-BRAF sdAbs were developed to target wild-type and mutated BRAF in order to disrupt its role in malignant cells such as, for example, cells involved in colon cancer and other malignancies.

Using methods that are well-known in the art, recombinant human BRAF protein was used to generate sdAbs that are directed against or can bind to an epitope of BRAF.

Additionally, the present invention comprises one or more mouse monoclonal antibodies which are directed against one or more domains of the anti-BRAF sdAb of the invention. The mouse monoclonal antibody can be generated by methods that are known by one of skill in the art. The mouse monoclonal antibody can be used in diagnostic assays, for example, the antibody can be used in an immunoassay such as an ELISA in order to measure the amount of anti-BRAF sdAb present in a patient's serum.

KRAS (negative control) and GST-STAT3 (16 kDa monovalent antigen, Creative BioMart #STAT3-1476H) were used as antigen probes in this assay. The GST-STAT3 protein was captured at 20 µg/ml in PBS using aminopropylsilane (APS) dip and read biosensors, specifically meant for hydrophobic protein. The probes were then dipped into wells with the GST-STAT3 protein, anti-STAT3 VHH13 (SEQ ID NO:3) sdAb or anti-KRAS at a concentration as indicated. The association rate (on rate) of the antigen was measured. The sensors were quenched with 1% BSA in water. The probes were dipped into assay buffer (PBS) and the dissociation rate (off rate) was measured.

The affinity, represented by the equilibrium constant for the dissociation of an antigen with an antigen-binding protein (KD) was determined from the obtained affinity constant (KA), and KD using 1:1 global fit analysis Fortebio software as shown below in Table 1. Affinity was determined by averaging KD values for curves with R2 values >0.95. The 250 nM anti-STAT3 VHH13 data point was omitted as it is an outlier. It was determined that the anti-STAT3 VHH13 (SEQ ID NO. 3) sdAb affinity was $1.16 \times 10^{-7}$. The affinity of anti-KRAS VHH was not determined.

TABLE 1

Local fit analysis, highlighted values used to determine the affinity to be $1.16 \times 10^{-7}$

| Sensor Type | Sample ID | Loading Sample ID | VHH Conc. (nM) | KD (M) | kon(1/Ms) | koff(1/s) | Full R^2 |
| --- | --- | --- | --- | --- | --- | --- | --- |
| APS (Aminopropylsilane) | ANTI-STAT3 VHH13 | STAT3 20 µg/ml | 1000 | 1.168E−07 | 3.16E+05 | 3.69E−02 | 0.985 |
| APS (Aminopropylsilane) | ANTI-STAT3 VHH13 | STAT3 20 µg/ml | 500 | 1.012E−07 | 4.04E+05 | 4.09E−02 | 0.974 |
| APS (Aminopropylsilane) | ANTI-STAT3 VHH13 | STAT3 20 µg/ml | 250 | <1.0E−12 | 4.69E+91 | 5.11E−02 | 0.980 |
| APS (Aminopropylsilane) | ANTI-STAT3 VHH13 | STAT3 20 µg/ml | 125 | 1.474E−07 | 3.09E+05 | 4.55E−02 | 0.991 |
| APS (Aminopropylsilane) | ANTI-STAT3 VHH13 | STAT3 20 µg/ml | 62.5 | 9.921E−08 | 2.71E+05 | 2.69E−02 | 0.975 |
| APS (Aminopropylsilane) | ANTI-STAT3 VHH13 | STAT3 20 µg/ml | 31.3 | 1.53E−06 | 6.75E+04 | 1.03E−01 | 0.656 |
| APS (Aminopropylsilane) | ANTI-kras | STAT3 20 µg/ml | 1000 | 6.75E−08 | 1.19E+04 | 8.01E−04 | 0.917 |
| APS (Aminopropylsilane) | ANTI-kras | STAT3 20 µg/ml | 500 | 2.916E−08 | 1.65E+04 | 4.80E−04 | 0.890 |
| APS (Aminopropylsilane) | ANTI-kras | STAT3 20 µg/ml | 250 | 4.324E−09 | 8.93E+04 | 3.86E−04 | 0.276 |
| APS (Aminopropylsilane) | ANTI-kras | STAT3 20 µg/ml | 125 | NA | NA | NA | NA |
| APS (Aminopropylsilane) | ANTI-kras | STAT3 20 µg/ml | 62.5 | NA | NA | NA | NA |
| APS (Aminopropylsilane) | ANTI-kras | STAT3 20 µg/ml | 31.3 | NA | NA | NA | NA |

EXAMPLES

Example 1: ANTI-STAT3 VHH13 (SEQ ID NO. 3) SDAB BINDS STAT3

In this example, the affinity of two VHH targets against STAT3 was measured using Octet based label-free binding assay. Anti-STAT3 VHH13 (SEQ ID NO:3) sdAb, anti- Example 2: Immunoprecipitation Studies The specificity of STAT3 sdAbs was assayed in human breast cancer cells. In this example, MDA-MB-231 human breast cancer cells were grown to 50% to 70% confluence. The cells were then disrupted in freshly prepared ice-cold lysis buffer (20 mM HEPES, pH 7.9, 400 mM NaCl, 0.1% NP-40, 10% glycerol, 1 mM sodium vanadate, 1 mM sodium fluoride, 1 mM dithiothreitol, 1 mM phenylmethylsulfonyl fluoride, 10 µg/mL aprotinin, 10 µg/mL leupeptin) for 45 minutes on ice. Lysates were then centrifuged, the supernatant collected, and protein concentration was determined using a modified Lowry method (Bio Rad, Hercules, Calif.). Total protein (1 mg) was incubated with 1.5 mg of Dynabeads (Invitrogen) with sdAbs against STAT3, a positive control (STAT3, cat#SC-482, Santa Cruz Biotechnology, Dallas, Tex.), or negative control (STAT-1, cat#9172, Cell Signaling, Danvers, Mass.) for 1 hr at 4° C. Beads were then washed. Following the final wash, 60 µl of lysis buffer was added, and the resulting supernatant was subject to Western blot analysis. Briefly, samples were separated on 10% polyacrylamide gels and transferred to a nitrocellulose membrane. The membranes were blocked, then incubated with appropriate primary and secondary antibodies. Anti-STAT3 antibody, used as a positive control, was from Cell Signaling (Cat#4904, Danvers, Mass.). The chemiluminescence reaction was performed using the ECL system from Santa Cruz Biotechnology (Dallas, Tex.).

Figure 3:
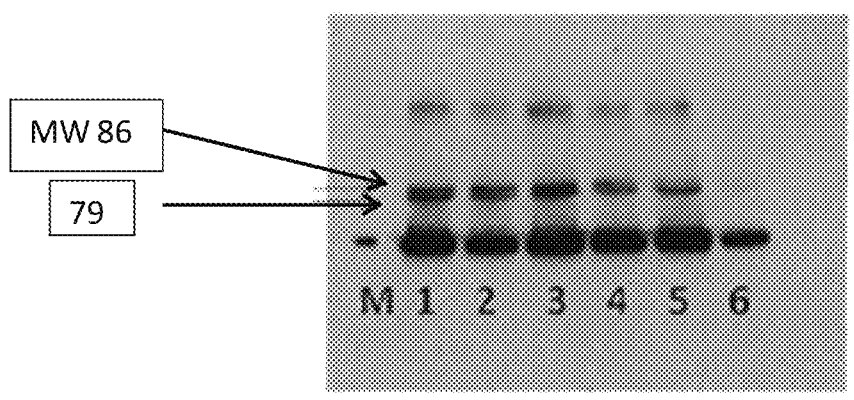
FIG. 3 depicts the results of an immunoprecipitation assay using anti-STAT3 bacterial VHH13 STAT3 (SEQ ID NO:3) and anti-STAT3 bacterial VHH14 STAT3 (SEQ ID NO:4)

As illustrated in FIG. 3, endogenous STAT3 immunoprecipitated with all sdAbs tested at varying amounts. M is the Marker lane containing the marker, lane 1 contained STAT3 VHH13 (SEQ ID NO:3) produced and isolated from mammalian cells, lane 2 contained STAT3 VHH14 (SEQ ID NO:4) produced and isolated from mammalian cells, lane 3 contained STAT3 VHH13 (SEQ ID NO:3) produced and isolated from bacterial cells, lane 4 contained STAT3 VHH14 (SEQ ID NO:4) produced and isolated from mammalian cells, lane 5 was the positive STAT3 antibody, lane 6, used STAT-1 as a negative control, showed no band.

Example 3: Anti-STAT3 Bacterial VHH13 Binds with High Affinity to Cell Lines Containing Constitutively Activated STAT3

The specificity of bacterial anti-STAT3 VHH13 (SEQ ID NO:3) using constitutively activated STAT3 in human (PANC-1 and DU145) and murine (4T1) cell lines was assayed. Commercial HeLa cells were also treated with interferon gamma (INFΓ) in order to induce phosphorylated STAT3. The PC-3 STAT3 null cell line was used as a negative control.

The cells were grown to 50% to 70% confluence, then disrupted in freshly prepared ice-cold lysis buffer as described above for 45 minutes on ice. Lysates were then centrifuged, the supernatant collected, and protein concentration was determined as described above. Total protein (1 mg) was incubated with 1.5 mg of Dynabeads (Invitrogen) containing the bacterial anti-STAT3 VHH13 (SEQ ID NO:3) or negative control (KRAS, Creative Biolabs, Shirley, N.Y.) for 1 hour at 4° C. Beads were then washed. Following the final wash, 60 μl of lysis buffer was added, and the resulting supernatant was subject to Western Blot analysis as described in Example 2.

Figure 4:
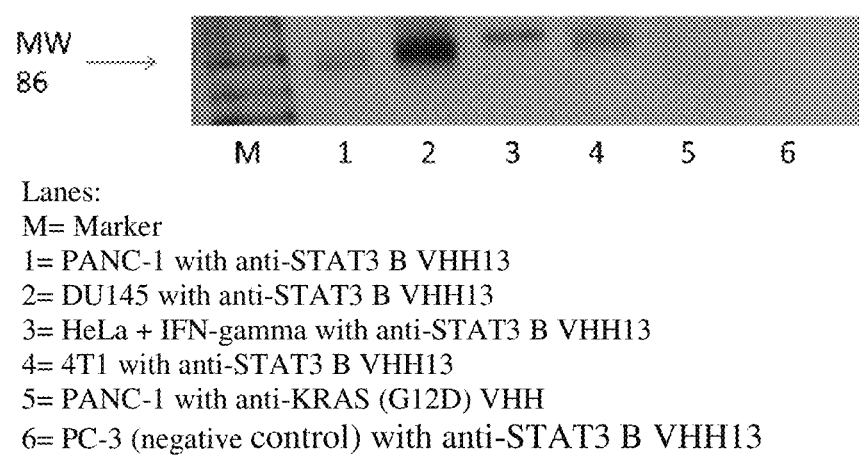
FIG. 4 depicts the results of an immunoprecipitation assay using anti-STAT3 bacterial VHH13 STAT3 (SEQ ID NO:3)

As illustrated in FIG. 4, endogenous STAT3 was immunoprecipitated by bacterial VHH13 STAT3 (SEQ ID NO:3) in the constitutively activated STAT3 cell lines: PANC-1 (lane 1), DU145 (lane 2), and 4T1 (lane 4). Furthermore, bacterial VHH13 STAT3 (SEQ ID NO:3) bound to the Phospho-STAT3 in HeLa lysate (lane 3). No bands were noted for either PANC-1 KRAS, lane 3, and PC-3 (negative control), lane 6.

Example 4: Cytotoxicity Studies of Anti-STAT3 SDABS in MDA-MB-231 Cancer Cell Lines In this example, the anti-proliferative effects of anti-STAT3 sdAbs were assayed using the human breast cancer cell line MDA-MB-231. For the experiments, MDA-MB-231 cells were grown until they reached a confluency of 90%. At that time, cells were washed, trypsinized and counted using a Coulter Counter (Beckman, Brea, Calif.). The proliferation studies were carried out using the 3-[4,5-dimethylthiaolyl]-2,5-diphenyltetrazolium bromide (MTT) assay. For this, cells were seeded in a 96-well plate at a density of $5 \times 10^3$ per well as indicated by the manufacturer (Roche Diagnostics Corporation, Indianapolis, Ind.). Cells were allowed to adhere for 24 hours and then the sdAbs were added at the appropriate concentrations (i.e., 0, 0.5, 1.0, 10.0, or 100 μg/ml). Cells were counted on day 3. For the 5-day treated cells, fresh media containing the sdAbs was refreshed on day 3. At the time of termination, 10 μl of MTT reagent (0.5 mg/mL) was added to each well as indicated by the manufacturer. After a 4 hour incubation period, 100 μl of solubilization solution was added and the plate was placed in the incubator overnight. All the plates were read at 570 nm wavelength using the Biotek plate reader (Winooski, Vt.).

All data were analyzed using GraphPad InStat 3 (GraphPad Software, Inc., La Jolla, Calif.). Treatments groups were compared with vehicle control group using one-way ANOVA. If a significant difference ($p<0.05$) was observed, the Tukey-Kramer multiple comparison test was conducted.

Based on the MIT experiment, the bacterial VHH13 anti-STAT3 (SEQ ID NO. 3) sdAb was found to be effective in inhibiting cell growth at days 3 and 5 post-treatment, as shown in Tables 2-5 below.

TABLE 2

Mean Absorbance (570 nM) ± S.E. Day 3 Post Treatment with Anti-STAT3 sdAbs in MDA-MB-231 Cells

| Treatment | Control | 0.5 μg/ml | 1.0 μg/ml | 10.0 μg/ml | 100 μg/ml | p-value* |
|---|---|---|---|---|---|---|
| H.VHH13 | 0.444 ± 0.030 | 0.504 ± 0.043 | 0.545 ± 0.060 | 0.603 ± 0.025 | 0.272 ± 0.011 | 0.001 |
| H.VHH14 | 0.404 ± 0.011 | 0.485 ± 0.040 | 0.402 ± 0.017 | 0.588 ± 0.020 | 0.416 ± 0.030 | 0.002 |
| B.VHH13 | 0.550 ± 0.036 | 0.685 ± 0.018 | 0.716 ± 0.023 | 0.355 ± 0.033 | 0.059 ± 0.001 | <0.0001 |
| B.VHH14 | 0.593 ± 0.014 | 0.666 ± 0.022 | 0.644 ± 0.045 | 0.456 ± 0.048 | 0.255 ± 0.005 | <0.0001 |

*One Way Analysis of Variance (ANOVA); Tukey-Kramer Multiple Comparison Test

TABLE 3

Effects of Anti-STAT3 sdAb Treatment on MDA-MB-231 Cell Proliferation after 3 Days of Treatment

| Treatment | μg/ml | % Inhibition | p-value* |
|---|---|---|---|
| H.VHH13 | 0.5 |  | NS |
|  | 1.0 |  | NS |
|  | 10.0 |  | NS |
|  | 100.0 | 38.7 | P < 0.05 |
| H.VHH14 | 0.5 |  | NS |
|  | 1.0 | 0.5 | NS |
|  | 10.0 |  | NS |
|  | 100.0 |  | NS |
| B.VHH13 | 0.5 |  | NS |
|  | 1.0 |  | NS |
|  | 10.0 | 35.5 | P < 0.001 |
|  | 100.0 | 89.3 | P < 0.001 |
| B.VHH14 | 0.5 |  | NS |
|  | 1.0 |  | NS |
|  | 10.0 | 23.1 | P < 0.05 |
|  | 100.0 | 57.0 | P < 0.001 |

*One Way Analysis of Variance (ANOVA); Tukey-Kramer Multiple Comparison Test

TABLE 4

Mean Absorbance (570 nM) ± S.E. Day 5 Post Treatment with Anti-STAT3 sdAb in MDA-MB-231 Cells

| Treatment | Control | 0.5 µg/ml | 1.0 µg/ml | 10.0 µg/ml | 100 µg/ml | p-value* |
|---|---|---|---|---|---|---|
| H.VHH13 | 1.100 ± 0.088 | 0.955 ± 0.013 | 0.963 ± 0.018 | 0.832 ± 0.028 | 0.721 ± 0.025 | 0.0012 |
| H.VHH14 | 0.983 ± 0.023 | 0.890 ± 0.021 | 0.935 ± 0.037 | 0.804 ± 0.015 | 0.797 ± 0.010 | 0.0007 |
| B.VHH13 | 0.804 ± 0.046 | 0.761 ± 0.055 | 0.653 ± 0.024 | 0.506 ± 0.030 | 0.083 ± 0.005 | <0.0001 |
| B.VHH14 | 0.677 ± 0.015 | 0.733 ± 0.038 | 0.794 ± 0.023 | 0.640 ± 0.011 | 0.549 ± 0.023 | <0.0001 |

*One Way Analysis of Variance (ANOVA); Tukey-Kramer Multiple Comparison Test

TABLE 5

Effects of Anti-STAT3 sdAb Treatment on MDA-MB-231 Cell Proliferation After 5 Days of Treatment

| Treatment | µg/ml | % Inhibition | p-value* |
|---|---|---|---|
| H.VHH13 | 0.5 | 13.2 | NS |
|  | 1.0 | 12.5 | NS |
|  | 10.0 | 24.4 | P < 0.01 |
|  | 100.0 | 34.5 | P < 0.001 |
| H.VHH14 | 0.5 | 9.5 | NS |
|  | 1.0 | 4.9 | NS |
|  | 10.0 | 18.2 | P < 0.001 |
|  | 100.0 | 18.9 | P < 0.001 |
| B.VHH13 | 0.5 | 5.4 | NS |
|  | 1.0 | 18.8 | NS |
|  | 10.0 | 37.1 | P < 0.001 |
|  | 100.0 | 89.7 | P < 0.001 |
| B.VHH14 | 0.5 | 0 | NS |
|  | 1.0 | 0 | NS |
|  | 10.0 | 5.5 | NS |
|  | 100.0 | 18.9 | P < 0.05 |

*One Way Analysis of Variance (ANOVA); Tukey-Kramer Multiple Comparison Test

Example 5: Cytotoxicity Studies of Anti-STAT3 SDABS in Human Breast (MDA-MB-231) and Pancreatic (PANC-1) Cancer Cell Lines In this Example, the anti-proliferative effects of anti-STAT3 VHH13 (SEQ ID NO. 3) and the VHH14 (SEQ ID NO. 4) sdAbs were assayed using the human breast cancer cell line MDA-MB-231 and the human pancreatic cancer cell line PANC-1. For the experiments, MDA-MB-231 and PANC-1 cells were grown until they were 90% confluent. At that time, cells were washed, trypsinized and counted using a Coulter Counter (Beckman, Brea, Calif.). The proliferation studies were carried out using the MTT assay described above. For the 5-day treated cells, fresh media containing the anti-STAT3 sdAbs was refreshed on day 3.

All data were analyzed using GraphPad InStat 3. Treatments groups were compared with vehicle control group using one-way ANOVA. If a significant difference (p<0.05) was observed, the Tukey-Kramer multiple comparison test was conducted.

Based on the MTT experiment, both the VHH13 (SEQ ID NO. 3) and the VHH14 (SEQ ID NO. 4) were found to inhibit cell growth in both the MDA-MB-231 and PANC-1 cancer cells, as shown in Tables 6-13 below.

TABLE 6

Mean Absorbance (570 nM) ± S.E. Day 3 Post Treatment With sdAbs in the MDA-MB-231 Cells

| Treatment | Experiment | Control | 10.0 µg/ml | 100 µg/ml | p-value* |
|---|---|---|---|---|---|
| B.VHH13 | 1 | 0.550 ± 0.036 | 0.355 ± 0.033 | 0.059 ± 0.001 | <0.0001 |
|  | 2 | 0.735 ± 0.092 | 0.489 ± 0.019 | 0.449 ± 0.054 | 0.0355 |
|  | 3 | 0.627 ± 0.033 | 0.432 ± 0.060 | 0.078 ± 0.001 | 0.0002 |
|  | 4 | 0.648 ± 0.090 | 0.576 ± 0.061 | 0.063 ± 0.002 | 0.0011 |
|  | Overall Mean | 0.640 ± 0.038 | 0.463 ± 0.047 | 0.163 ± 0.10 | 0.0019 |
| B.VHH14 | 1 | 0.593 ± 0.014 | 0.456 ± 0.048 | 0.255 ± 0.005 | 0.0005 |
|  | 2 | 0.624 ± 0.046 | 0.499 ± 0.018 | 0.357 ± 0.019 | 0.0025 |
|  | 3 | 0.816 ± 0.088 | 0.502 ± 0.048 | 0.308 ± 0.021 | 0.0026 |
|  | 4 | 0.729 ± 0.051 | 0.559 ± 0.041 | 0.287 ± 0.021 | 0.0007 |
|  | Overall Mean | 0.691 ± 0.051 | 0.504 ± 0.021 | 0.302 ± 0.043 | <0.0001 |

*One Way Analysis of Variance (ANOVA); Tukey-Kramer Multiple Comparison Test

TABLE 7

Mean Absorbance (570 nM) ± S.E. Day 5 Post Treatment with Anti-STAT3 sdAbs in MDA-MB-231 Cells

| Treatment | Experiment | Control | 10.0 µg/ml | 100 µg/ml | p-value* |
|---|---|---|---|---|---|
| B.VHH13 | 1 | 0.804 ± 0.046 | 0.506 ± 0.030 | 0.083 ± 0.005 | <0.0001 |
|  | 2 | 0.561 ± 0.024 | 0.417 ± 0.011 | 0.266 ± 0.015 | <0.0001 |

TABLE 7-continued

Mean Absorbance (570 nM) ± S.E. Day 5 Post
Treatment with Anti-STAT3 sdAbs in MDA-MB-231 Cells

| Treatment | Experiment | Control | 10.0 µg/ml | 100 µg/ml | p-value* |
|---|---|---|---|---|---|
| | 3 | 0.970 ± 0.048 | 0.814 ± 0.052 | 0.105 ± 0.005 | <0.0001 |
| | 4 | 0.757 ± 0.118 | 0.665 ± 0.036 | 0.087 ± 0.004 | 0.011 |
| Overall Mean | | 0.773 ± 0.084 | 0.601 ± 0.088 | 0.135 ± 0.044 | 0.0005 |
| B.VHH14 | 1 | 0.677 ± 0.015 | 0.640 ± 0.011 | 0.549 ± 0.023 | 0.0047 |
| | 2 | 0.456 ± 0.037 | 0.338 ± 0.023 | 0.274 ± 0.032 | 0.0166 |
| | 3 | 0.983 ± 0.019 | 0.930 ± 0.044 | 0.578 ± 0.039 | 0.0004 |
| | 4 | 1.092 ± 0.053 | 0.842 ± 0.052 | 0.499 ± 0.036 | 0.0004 |
| Overall Mean | | 0.802 ± 0.145 | 0.688 ± 0.131 | 0.475 ± 0.0690 | 0.2022 |

*One Way Analysis of Variance (ANOVA); Tukey-Kramer Multiple Comparison Test

TABLE 8

Mean Absorbance (570 nM) ± S.E. Day 3 Post
Treatment with Anti-STAT3 sdAbs in the PANC-1 Cells

| Treatment | Experiment | Control | 10.0 µg/ml | 100 µg/ml | p-value* |
|---|---|---|---|---|---|
| B.VHH13 | 1 | 0.756 ± 0.045 | 0.432 ± 0.015 | 0.307 ± 0.012 | <0.0001 |
| | 2 | 1.347 ± 0.189 | 0.491 ± 0.087 | 0.169 ± 0.094 | 0.0019 |
| | 3 | 1.025 ± 0.056 | 0.493 ± 0.029 | 0.166 ± 0.028 | <0.0001 |
| Overall Mean | | 1.043 ± 0.171 | 0.472 ± 0.020 | 0.214 ± 0.047 | 0.0034 |
| H.VHH13 | 1 | 1.541 ± 0.097 | 1.066 ± 0.153 | 0.732 ± 0.015 | 0.0046 |
| | 2 | 1.611 ± 0.119 | 1.353 ± 0.119 | 0.762 ± 0.654 | 0.3527 |
| | 3 | 1.074 ± 0.040 | 0.897 ± 0.154 | 0.700 ± 0.082 | 0.1092 |
| Overall Mean | | 1.409 ± 0.169 | 1.105 ± 0.133 | 0.731 ± 0.181 | 0.0238 |
| H.VHH14 | 1 | 1.195 ± 0.205 | 0.920 ± 0.133 | 0.808 ± 0.239 | 0.4161 |
| | 2 | 1.423 ± 0.038 | 1.183 ± 0.114 | 0.993 ± 0.088 | 0.0338 |
| | 3 | 1.293 ± 0.169 | 1.163 ± 0.044 | 0.916 ± 0.088 | 0.1330 |
| Overall Mean | | 1.304 ± 0.066 | 1.089 ± 0.085 | 0.906 ± 0.054 | 0.0188 |

*One Way Analysis of Variance (ANOVA); Tukey-Kramer Multiple Comparison Test

TABLE 9

Mean Absorbance (570 nM) ± S.E. Day 5 Post
Treatment with Anti-STAT3 sdAbs in PANC-1 Cells

| Treatment | Experiment | Control | 10.0 µg/ml | 100 µg/ml | p-value* |
|---|---|---|---|---|---|
| B.VHH13 | 1 | 0.687 ± 0.047 | 0.433 ± 0.036 | 0.243 ± 0.024 | 0.0004 |
| | 2 | 1.670 ± 0.196 | 0.869 ± 0.053 | 0.211 ± 0.006 | 0.0004 |
| | 3 | 1.389 ± 0.044 | 0.627 ± 0.073 | 0.203 ± 0.013 | <0.0001 |
| Overall Mean | | 1.249 ± 0.292 | 0.643 ± 0.126 | 0.219 ± 0.012 | 0.0208 |
| H.VHH13 | 1 | 1.462 ± 0.150 | 1.128 ± 0.105 | 0.839 ± 0.117 | 0.0349 |
| | 2 | 1.792 ± 0.202 | 1.341 ± 0.095 | 0.911 ± 0.079 | 0.0113 |
| | 3 | 1.605 ± 0.289 | 1.161 ± 0.140 | 0.820 ± 0.005 | 0.0638 |
| Overall Mean | | 1.620 ± 0.096 | 1.210 ± 0.066 | 0.857 ± 0.028 | 0.0007 |
| H.VHH14 | 1 | 1.992 ± 0.105 | 1.859 ± 0.033 | 0.095 ± 0.003 | <0.0001 |
| | 2 | 1.517 ± 0.050 | 1.165 ± 0.015 | 1.169 ± 0.050 | 0.0015 |
| | 3 | 1.579 ± 0.134 | 1.081 ± 0.103 | 0.998 ± 0.049 | 0.0136 |
| Overall Mean | | 1.696 ± 0.149 | 1.368 ± 0.247 | 0.754 ± 0.333 | 0.0967 |

*One Way Analysis of Variance (ANOVA); Tukey-Kramer Multiple Comparison Test

TABLE 10

Mean Growth Inhibition Post 3 Days of Anti-STAT3
sdAbs Treatment on MDA-MB-231 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P < 0.0001 | 35.5 | P < 0.001 | 89.3 | P < 0.001 |
| | 2 | P = 0.03 | 33.5 | ns | 38.9 | P < 0.05 |

TABLE 10-continued

Mean Growth Inhibition Post 3 Days of Anti-STAT3 sdAbs Treatment on MDA-MB-231 Cell Proliferation

| Treatment | Experiment | P-value[a] | 10.0 µg/ml | P-value[b] | 100 µg/ml | P-value[b] |
|---|---|---|---|---|---|---|
| | 3 | P = 0.0001 | 31.1 | P < 0.05 | 87.6 | P < 0.001 |
| | 4 | P = 0.0001 | 11.1 | ns | 90.3 | P < 0.01 |
| Overall Average % Inhibition | | | 27.8 | | 76.5 | |
| B.VHH14 | 1 | P < 0.001 | 23.1 | P < 0.05 | 57.0 | P < 0.001 |
| | 2 | P = 0.03 | 20.0 | ns | 42.8 | P < 0.01 |
| | 3 | P = 0.03 | 38.5 | P < 0.05 | 62.3 | P < 0.01 |
| | 4 | P = 0.006 | 23.3 | ns | 60.6 | P < 0.001 |
| Overall Average % Inhibition | | | 26.2 | | 55.7 | |

[a]One-way Analysis of Variance (ANOVA);
[b]Post test = Tukey-Kramer Multiple Comparisons Test

TABLE 11

Mean Growth Inhibition Post 5 days of Anti-STAT3 sdAbs Treatment on MDA-MB-231 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P < 0.0001 | 37.1 | P < 0.001 | 89.7 | P < 0.001 |
| | 2 | P < 0.0001 | 25.7 | P < 0.001 | 52.6 | P < 0.001 |
| | 3 | P < 0.0001 | 16.1 | ns | 89.2 | P < 0.001 |
| | 4 | P = 0.001 | 12.2 | ns | 88.5 | P < 0.01 |
| Overall Average % Inhibition | | | 22.8 | | 80.0 | |
| B.VHH14 | 1 | P < 0.0001 | 5.5 | ns | 18.9 | P < 0.05 |
| | 2 | P = 0.02 | 25.9 | ns | 39.9 | P < 0.05 |
| | 3 | P = 0.0004 | 5.4 | ns | 41.2 | P < 0.001 |
| | 4 | P = 0.0004 | 22.9 | P < 0.05 | 54.3 | P < 0.001 |
| Overall Average % Inhibition | | | 14.9 | | 38.6 | |

[a]One-way Analysis of Variance (ANOVA);
[b]Post test = Tukey-Kramer Multiple Comparisons Test

TABLE 12

Mean Growth Inhibition Post 3 Days of Anti-STAT3 sdAbs Treatment on PANC-1 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P < 0.0001 | 42.9 | P < 0.001 | 59.4 | P < 0.001 |
| | 2 | P = 0.03 | 63.5 | P < 0.05 | 87.5 | P < 0.01 |
| | 3 | P < 0.0001 | 51.9 | P < 0.001 | 83.8 | P < 0.001 |
| Overall Average % Inhibition | | | 52.8 | | 76.9 | |
| H.VHH13 | 1 | P = 0.005 | 30.8 | P < 0.05 | 52.5 | P < 0.01 |
| | 2 | P = 0.002 | 16.0 | ns | 52.7 | P < 0.01 |
| | 3 | P = 0.11 | 16.5 | ns | 34.8 | ns |
| Overall Average % Inhibition | | | 21.1 | | 46.7 | |
| H.VHH14 | 1 | P = 0.42 | 23.0 | ns | 32.4 | ns |
| | 2 | P = 0.03 | 16.9 | ns | 30.2 | P < 0.05 |
| | 3 | P = 0.13 | 10.1 | ns | 29.2 | ns |
| Overall Average % Inhibition | | | 16.7 | | 30.6 | |

[a]One-way Analysis of Variance (ANOVA);
[b]Post test = Tukey-Kramer Multiple Comparisons Test

TABLE 13

Mean Growth Inhibition Post 5 Days of Anti-STAT3 sdAbs Treatment on PANC-1 Cell Proliferation

| Treatment | Experiment | P-value[a] | 10.0 μg/ml | P-value[b] | 100 μg/ml | P-value[b] |
|---|---|---|---|---|---|---|
| B.VHH13 | 1 | P = 0.0004 | 37.0 | P < 0.01 | 64.6 | P < 0.001 |
|  | 2 | P = 0.0004 | 48.0 | P < 0.01 | 87.4 | P < 0.001 |
|  | 3 | P < 0.0001 | 54.9 | P < 0.001 | 85.4 | P < 0.001 |
| Overall Average % Inhibition |  |  | 46.6 |  | 79.1 |  |
| H.VHH13 | 1 | P = 0.03 | 22.8 | ns | 42.6 | P < 0.05 |
|  | 2 | P = 0.01 | 25.2 | ns | 49.2 | P < 0.01 |
|  | 3 | P = 0.06 | 27.7 | ns | 48.9 | ns |
| Overall Average % Inhibition |  |  | 25.2 |  | 46.9 |  |
| H.VHH14 | 1 | P = 0.08 | 26.8 | ns | 14.8 | ns |
|  | 2 | P = 0.002 | 23.2 | P < 0.01 | 22.9 | P < 0.01 |
|  | 3 | P = 0.02 | 31.5 | P < 0.05 | 36.8 | P < 0.05 |
| Overall Average % Inhibition |  |  | 27.2 |  | 24.8 |  |

[a]One-way Analysis of Variance (ANOVA);
[b]Post test = Tukey-Kramer Multiple Comparisons Test

Example 6: Anti-Proliferative Actions of STAT3 SDABS in the Human Breast Cancer and Human Prostate Cancer Cell Lines The anti-proliferative effects of the STAT3 VHH13 (SEQ ID NO. 3) sdAb were assayed in the human breast cancer cell line MDA-MB-231 and the human prostate cancer cell lines DU145. For the experiments, cancer cells were grown until they reached 90% confluence. At that time, cells were washed, trypsinized, and counted using a Coulter Counter (Beckman, Brea, Calif.). The proliferation studies done using the MTT assay as described above.

The anti-proliferative properties of anti-STAT3 bacterial VHH13 (SEQ ID NO. 3) sdAb on MDA-MB-231 cells were compared to its actions on DU145 cells. As shown in Table 14, MDA-MB-231 cells treated with the anti-STAT3 (SEQ ID NO:3) sdAbs showed an average growth inhibition of 29.6 and 91.2 at 50.0 and 100 μg/ml, respectively. In the DU145 cells, a similar growth inhibition (31.2 and 92.1% for 50.0 and 100 μg/ml, respectively) was seen as set forth in Table 15.

TABLE 14

Anti-proliferative Actions of Anti-STAT3 Bacterial VHH13 sdAbs on MDA-MB-231 Breast Cancer Cells

| | Experiment 1 Absorbance (% Inhibition) | Experiment 2 Absorbance (% Inhibition) | Experiment 3 Absorbance (% Inhibition) | Average Absorbance (% Inhibition) | p-value* |
|---|---|---|---|---|---|
| control | 0.93 | 1.25 | 1.46 | 1.21 | |
| 50 μg | 0.82 (12.0) | 0.99 (20.5) | 0.64 (56.2) | 0.82 (32.6) | NS |
| 100 μg | 0.07 (93.1) | 0.12 (90.1) | 0.14 (90.5) | 0.11 (91.0) | <0.001 |

*One Way Analysis of Variance (ANOVA); Tukey-Kramer Multiple Comparison Test

TABLE 15

Anti-proliferative Actions of Anti-STAT3 Bacterial VHH13 sdAbs on DU145 Prostate Cancer Cells

| | Experiment 1 Absorbance (% Inhibition) | Experiment 2 Absorbance (% Inhibition) | Experiment 3 Absorbance (% Inhibition) | Average Absorbance (% Inhibition) | p-value* |
|---|---|---|---|---|---|
| control | 1.05 | 1.58 | 1.61 | 1.41 | |
| 50 μg | 0.68 (35.7) | 1.2 (55.5) | 1.03 (35.8) | 0.98 (30.5) | NS |
| 100 μg | 0.13 (87.4) | 0.12 (95.7) | 0.06 (96.1) | 0.10 (92.7) | <0.001 |

*One Way Analysis of Variance (ANOVA); Tukey-Kramer Multiple Comparison Test

Example 7: Anti-Proliferative Effects of STAT3 VHH13 (SEQ ID NO. 3) SDABS on Human Cancer Cell Lines To test the anti-proliferative effects of the STAT3 VHH13 (SEQ ID NO. 3) sdAbs using the human cancer cell lines: MDA-MB-231, MDA-MB-468, MCF-7, BT474, and DU145 as shown in Table 16.

All human cancer cell lines were obtained from American Type Culture Collection (Manassas, Va.). Cell lines were maintained and cultured in RPMI 1640 media (MDA-MB-231, MDA-MB-468, MCF-7, BT474) or MEM-E (DU145) containing 10% fetal bovine serum, 2 mM L-glutamine and 1% antibiotic-antimycotic solution (10 units/mL penicillin, 10 µg/mL streptomycin and 25 µg/mL amphotericin B). Cells were kept at 37° C. in a humidified atmosphere of 5% $CO_2$. Cell culture supplies were obtained from Life Technologies, Inc., (Grand Island, N.Y.). The MTT reagent was purchased from Sigma Aldrich (St. Louis, Mo.).

For the experiments, cancer cells were grown until they reached 90% confluency. At that time, cells were washed, trypsinized and counted using a Coulter Counter (Beckman, Brea, Calif.). The proliferation studies were carried out using the MTT assay as described above.

The anti-proliferative properties of Anti-STAT3 Bacterial VHH13 (SEQ ID NO:3) sdAbs were evaluated on five breast cancer cells of representing various classifications (Table 34). As shown in Table 17, all cell lines at 72 hours post treatment showed significant growth inhibition. The greatest growth inhibition was noted at 100 and 200 µg/ml dose for all cell lines. The half maximal inhibitory concentration ($IC_{50}$) for growth in the cell lines tested were: 10.1±2.4, 12.36±1.5, 14.8±1.6, and 25.2±14.7 for the MDA-MB-231, MDA-MB-468, MCF-7, and BT474 cell lines, respectively. These data suggest that the triple negative breast cancer cell lines require the lowest concentration of VHH13 (SEQ ID NO:3) sdAbs to achieve the $IC_{50}$ as compared to estrogen/progesterone positive cell lines (i.e., MCF-7) or HER2 amplified cell lines (i.e., BT474).

TABLE 16

Breast Cancer Cell Line Characteristics

| Cell line | Disease | Immunoprofile | Classification |
|---|---|---|---|
| MDA-MB-231 | adenocarcinoma | ER-, PR-, HER2- | Basal; Claudin-low |
| MDA-MB-468 | adenocarcinoma | ER-, PR-, Her2- | Basal |
| MDA-MB-453 | metastatic carcinoma | ER, PR, HER2- | Unclassified |
| BT474 | ductal carcinoma | Her2 amplified | Luminal B |
| MCF-7 | adenocarcinoma | ER+, PR+, HER2+ | Luminal A |

TABLE 17

Inhibition of Breast Cancer Cell Lines by Anti-STAT3 VHH13 (SEQ ID NO. 3) sdAbs

| Cell Line | Treatment (µg/ml) | Mean Abs | % Inhibition | p-value |
|---|---|---|---|---|
| BT474 | 0 | 0.634 | | |
| | 0.39 | 0.322 | 49.3 | P < 0.001 |
| | 0.78 | 0.462 | 27.2 | P < 0.001 |
| | 1.56 | 0.502 | 20.8 | P < 0.01 |
| | 3.13 | 0.446 | 29.7 | P < 0.001 |
| | 6.25 | 0.469 | 26.1 | P < 0.001 |
| | 12.5 | 0.363 | 42.7 | P < 0.001 |
| | 25 | 0.256 | 59.6 | P < 0.001 |
| | 50 | 0.145 | 77.2 | P < 0.001 |
| | 100 | 0.046 | 92.8 | P < 0.001 |
| | 200 | 0.040 | 93.8 | P < 0.001 |
| MCF-7 | 0 | 0.590 | | |
| | 0.39 | 0.818 | 0 | |
| | 0.78 | 0.785 | 0 | |
| | 1.56 | 0.823 | 0 | |
| | 3.13 | 0.689 | 0 | |
| | 6.25 | 0.435 | 22.1 | NS |
| | 12.5 | 0.327 | 41.6 | P < 0.01 |
| | 25 | 0.212 | 62.1 | P < 0.001 |
| | 50 | 0.057 | 89.9 | P < 0.001 |
| | 100 | 0.038 | 93.2 | P < 0.001 |
| | 200 | 0.040 | 92.9 | P < 0.001 |
| MDA-MB-468 | 0 | 0.253 | | |
| | 0.39 | 0.311 | 0 | |
| | 0.78 | 0.289 | 0 | |
| | 1.56 | 0.201 | 20.6 | |
| | 3.13 | 0.223 | 11.9 | |
| | 6.25 | 0.230 | 9.1 | |
| | 12.5 | 0.130 | 48.6 | P < 0.001 |
| | 25 | 0.067 | 73.5 | P < 0.001 |
| | 50 | 0.042 | 83.4 | P < 0.001 |
| | 100 | 0.038 | 85.0 | P < 0.001 |
| | 200 | 0.040 | 84.4 | P < 0.001 |
| MDA-MB-231 | 0 | 0.502 | | |
| | 0.39 | 0.603 | 0 | |
| | 0.78 | 0.576 | 0 | |
| | 1.56 | 0.570 | 0 | |
| | 3.13 | 0.445 | 11.4 | P < 0.001 |
| | 6.25 | 0.312 | 37.8 | P < 0.001 |
| | 12.5 | 0.224 | 55.4 | P < 0.001 |
| | 25 | 0.196 | 60.9 | P < 0.001 |
| | 50 | 0.130 | 74.2 | P < 0.001 |
| | 100 | 0.041 | 91.8 | P < 0.001 |
| | 200 | 0.042 | 91.7 | P < 0.001 |

The actions of anti-STAT3 bacterial VHH13 (SEQ ID NO:3) sdAb was also evaluated in the human prostate cancer cell line DU145, as shown in Table 18. The anti-STAT3 bacterial VHH13 (SEQ ID NO:3) sdAb showed dose-dependent growth inhibition in all cancer cells tested.

TABLE 18

Effect of Anti-STAT3 VHH13 sdAbs on Prostate Cancer Cell Lines

| | Treatment (mg/ml) | Mean Abs | % Inhibition | p-value |
|---|---|---|---|---|
| DU145 | 0 | 0.771 | | |
| DU145 | 0.39 | 0.906 | 0 | |
| DU145 | 0.78 | 1.023 | 0 | |
| DU145 | 1.56 | 0.967 | 0 | |
| DU145 | 3.13 | 0.783 | 0 | |
| DU145 | 6.25 | 0.770 | 0 | |
| DU145 | 12.5 | 0.560 | 27.4 | P < 0.05 |
| DU145 | 25 | 0.359 | 53.5 | P < 0.001 |
| DU145 | 50 | 0.161 | 79.1 | P < 0.001 |
| DU145 | 100 | 0.039 | 95.0 | P < 0.001 |
| DU145 | 200 | 0.039 | 95.0 | P < 0.001 |

Example 8: Maximum Tolerated Dose of Anti-STAT3 Bacterial VHH13 (SEQ ID NO:3) in BALB/C Mice In this Example, the tolerance of anti-STAT3 bacterial VHH13 (SEQ ID NO:3) sdAb was assayed in test animals using the human breast cancer cell line MDA-MB-231. For the experiment, a total of 9 BALB/C nude female mice (6 to 7 weeks old) were divided into three groups according to body weights. (Table 19) Mice (n=3) received either vehicle (PBS) or anti-STAT3 bacterial VHH13 (SEQ ID NO:3) sdAb at 250 or 500 mg/kg body weight/day for five days. During the study, mortality/morbidity was performed twice daily. Body weights were recorded on days 1, 4, and 6 of the study as well as on the day of study termination (Day 13). Toxicity was assessed by body weight measurements and mouse behavior compared to vehicle control mice. Upon completion of treatment phase, animals were followed for an additional week to note any abnormalities in body weights and/or general health post treatment.

TABLE 19

Experimental Design of Maximum Tolerated Dose Study

| Group | # Mice | Treatment | Dose | Route | Frequency |
|---|---|---|---|---|---|
| 1 | 3 | PBS Vehicle | — | IP | 5 days |
| 2 | 3 | Bacterial VHH13 | 250 µg/kg b.w. | IP | 5 days |
| 3 | 3 | Bacterial VHH13 | 500 µg/kg b.w. | IP | 5 days |

As illustrated in Table 20, there was no significant difference in body weights among the groups, and anti-STAT3 bacterial VHH13 (SEQ ID NO:3) sdAb was not associated with any drug-related deaths at either dosing level. Additionally, no behavior changes were observed in the animals treated with anti-STAT3 bacterial VHH13 (SEQ ID NO:3) sdAb as compared to the control mice.

TABLE 20

| Group | Mean body weights ± S.E | | | | |
|---|---|---|---|---|---|
| | Randomization | Day 1 | Day 4 | Day 6 | Day 13 |
| Vehicle | 17.1 ± 0.06 | 17.1 ± 0.07 | 17.8 ± 0.12 | 18.1 ± 0.09 | 18.8 ± 0.20 |
| 250 µg/kg | 17.1 ± 0.06 | 17.2 ± 0.03 | 17.2 ± 0.15 | 17.5 ± 0.15 | 18.1 ± 0.21 |
| 500 µg/kg | 17.1 ± 0.17 | 17.1 ± 0.09 | 17.8 ± 0.18 | 18.0 ± 0.20 | 18.5 ± 0.18 |
| p-value* | >0.9999 | 0.52 | 0.05 | 0.07 | 0.11 |

*One Way Analysis of Variance (ANOVA); Tukey-Kramer Multiple Comparison Test

Example 9: Activity of Bacterial Anti-STAT3 VHH13 (SEQ ID NO:3) in Nude BALB/C Mice Xenograft and Human Breast Cancer and Human Pancreatic Cancer Cells In this example, the activity of anti-STAT3 bacterial VHH13 (SEQ ID NO:3) sdAb was evaluated in mice using the human breast cancer cell line MDA-MB-231. Briefly, the activity of anti-STAT3 bacterial VHH13 (SEQ ID NO:3) sdAb was evaluated using: the MDA-MB-231 human breast cancer xenograft model and the PANC-1 human pancreatic cancer xenograft model. Dosing schedules were as follows: Group 1 (n=6; PBS; IP) daily for 14 days [QDx14]; and Group 2 (n-12; 500 µg/kg bw; IP), every day for 14 days [QDx14]. An observation period of 5 days followed the drug administration.

The human breast cancer cell lines (MDA-MB-231 and PANC-1) were obtained from American Type Culture Collection (ATCC) (Manassas, Va.). The MDA-MB-231 cells were growth in MEM (Life Technologies, Grand Island, N.Y.) supplemented with 10% FBS (Atlanta Biologicals, Flowery Branch, Ga.) and Penicillin-Streptomycin-Glutamine (Life Technologies, Grand Island, N.Y.). The PANC-1 cells were grown in RPMI 1640 media (Life Technologies, Grand Island, N.Y.) supplemented with 10% FBS and Penicillin-Streptomycin-Glutamine. All cells were grown in the presence of 5% $CO_2$ at 37° C. in an incubator.

Athymic nude-Foxnl$^{nu}$ male mice aged 4 to 5 weeks were purchased from Harlan Laboratories (Indianapolis, Ind.). Animals were quarantined for one week and housed five mice per cage, with a 12-hr light-dark cycle, and a relative humidity of 50%. Drinking water and diet were supplied to the animals ad libitum. All animals were housed under pathogen-free conditions and experiments were performed in accordance with the IIT Research Institute Animal Use and Care Committee. For the MDA-MB-231 xenograft study, cells ($4\times10^6$) in a 100-µL final volume of MEM media were injected subcutaneously into right flanks of mice. For the PANC-1 xenograft study, cells ($5\times10^6$) in a 100-µL final volume of RPMI media were injected subcutaneously into right flanks of mice. Tumor measurements for both models were initiated as soon as the tumors were palpable. Thereafter, tumors were measured twice weekly. Animals were randomized when tumors reach a range size of 75 to 175 $mm^3$, control (n=6) and a treatment (n=12) groups were randomized using the stratified random sampling algorithm. Treatment (anti-STAT3 bacterial VHH13 (SEQ ID NO:3) sdAb) or Vehicle (PBS) was initiated the day following randomization. The treatment was well tolerated and associated with no drug-related deaths. No significant body weight loss was noted.

For the MDA-MB-231 xenograft study, the randomization Mean (±SE) tumor size was: 103.01±11.89 and 102.61±9.60 for control and treatment groups respectively. Mean body weights (±SE) at randomization were: 32.08±0.76 and 30.27+0.75 for Group 1 and Group 2, respectively. Table 21 shows the mean body weights (±SE) for the entire study.

TABLE 21

Mean body weights ± S.E.

| Treatment | Day 1 | Day 6 | Day 9 | Day 12 | Day 16 | Day 20 |
|---|---|---|---|---|---|---|
| Vehicle | 31.0 ± 0.83 | 32.1 ± 0.76 | 31.9 ± 0.66 | 32.1 ± 0.68 | 32.0 ± 0.71 | 32.5 ± 0.88 |
| Anti-STAT3 VHH13 | 29.2 ± 0.71 | 30.3 ± 0.75 | 30.4 ± 0.79 | 29.9 ± 0.72 | 30.6 ± 0.74 | 30.6 ± 0.77 |
| p-value* | 0.16 | 0.18 | 0.27 | .09 | 0.28 | 0.17 |

*Two-tail T-Test

Figure 5:
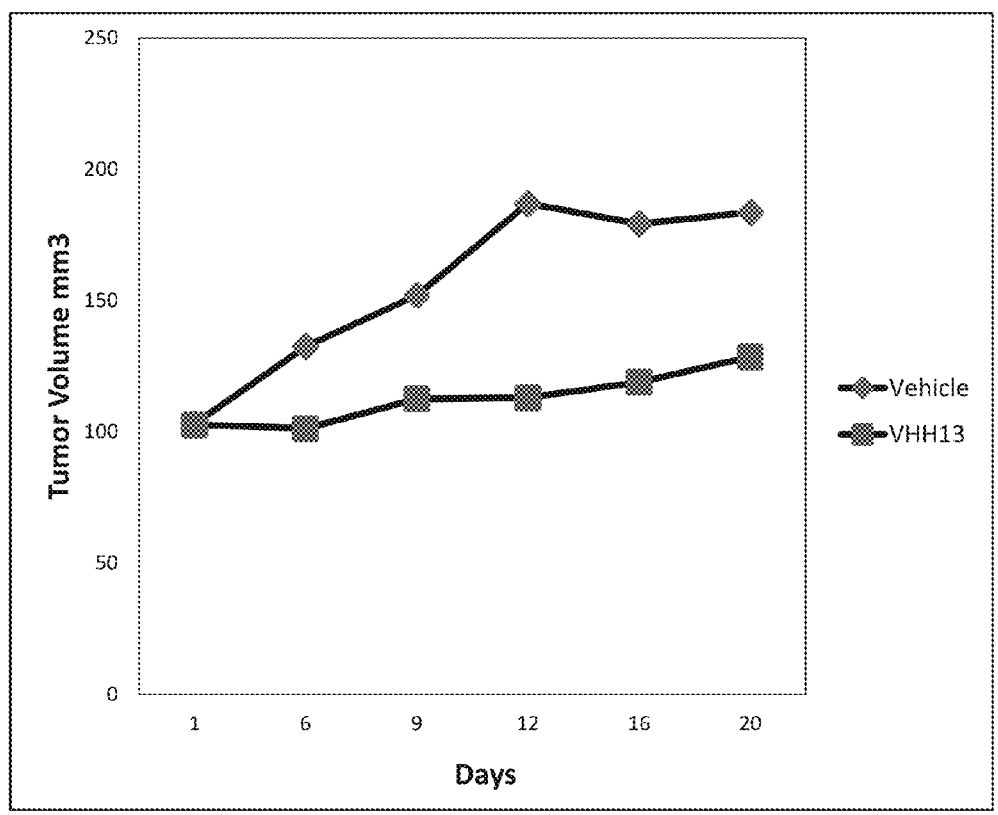
FIG. 5 illustrates the growth inhibition of anti-STAT3 bacterial VHH13 (SEQ ID NO:3) sdAb in the MDA-MB-231 xenograft model, dosed at 0.5 mg/kg/day.

On day 14 of dosing, the mean tumor size (±SE) for the control was 179.11±19.39 versus 118.86±15.94 for treatment group. Mean body weights (±SE) at termination were: 31.98±0.71 and 30.55±0.74 for Group 1 and Group 2, respectively. Table 22 summarizes the tumor volumes (±SE) for entire study. The % mean tumor growth inhibition in the treatment group was 33.64%. The tumor doubling times were as follows: Group 1: 44.27 days; and Group 2: 61.06 days. FIG. 5 illustrates the growth inhibition of anti-STAT3 bacterial VHH13 (SEQ ID NO:3) sdAb in the MDA-MB-231 xenograft model. Anti-STAT3 bacterial VHH13 (SEQ ID NO:3) sdAb showed significant growth inhibition (p=0.047). Thus, anti-STAT3 bacterial VHH13 (SEQ ID NO:3) sdAb has chemotherapeutic activity in the MDA-MB-231 human breast cancer model system.

TABLE 22

Individual Tumor Measurements (mm³) for the MDA-MB-231 Xenograft Model

| Group | Animal # | Day 1 | Day 6 | Day 9 | Day 12 | Day 16 | Day 20 |
|---|---|---|---|---|---|---|---|
| 1 | 1 | 117.43 | 141.72 | 135.00 | 139.31 | 127.93 | 133.19 |
|  | 2 | 130.30 | 142.83 | 206.15 | 256.99 | 244.06 | 243.00 |
|  | 3 | 78.00 | 105.97 | 114.04 | 144.06 | 154.50 | 158.94 |
|  | 4 | 118.24 | 162.41 | 171.39 | 225.59 | 181.32 | 217.97 |
|  | 5 | 71.10 | 109.03 | 133.13 | 168.80 | 187.73 | 164.45 |
| Mean |  | 103.01 | 132.39 | 151.94 | 186.95 | 179.11 | 183.51 |
| S.E. |  | 11.89 | 10.82 | 16.42 | 23.28 | 19.39 | 20.28 |
| 2 | 6 | 123.94 | 114.91 | 129.22 | 176.04 | 170.09 | 162.98 |
|  | 7 | 85.93 | 101.06 | 112.60 | 112.24 | 139.56 | 96.43 |
|  | 8 | 147.34 | 148.72 | 169.69 | 185.08 | 170.07 | 256.71 |
|  | 9 | 115.91 | 103.64 | 108.37 | 141.21 | 144.51 | 119.42 |
|  | 10 | 73.23 | 82.59 | 110.13 | 91.22 | 166.77 | 285.88 |
|  | 11 | 163.73 | 178.23 | 183.79 | 165.52 | 214.28 | 129.51 |
|  | 12 | 75.54 | 83.94 | 103.68 | 119.88 | 104.26 | 99.48 |
|  | 13 | 70.04 | 89.24 | 102.60 | 75.25 | 57.65 | 95.23 |
|  | 14 | 101.62 | 65.09 | 82.02 | 68.01 | 61.41 | 61.83 |
|  | 15 | 67.83 | 62.21 | 59.00 | 77.04 | 65.49 | 82.73 |
|  | 16 | 131.93 | 75.28 | 76.21 | 53.55 | 73.66 | 51.61 |
|  | 17 | 74.28 | 109.06 | 111.92 | 89.94 | 58.56 | 100.07 |
| Mean |  | 102.61 | 101.16 | 112.44 | 112.92 | 118.86 | 128.49 |
| S.E. |  | 9.6 | 9.8 | 10.3 | 12.9 | 15.9 | 21.1 |
| P-value |  | 0.98 | 0.08 | 0.06 | 0.01 | 0.05 | 0.14 |

For the PANC-1 xenograft study, the randomization Mean (+SE) tumor sizes were 107.01±4.54 in the control and 110.58±6.18 in the treatment groups. Mean body weights (±SE) at randomization were: 29.0±0.81 and 28.5±0.70 for Group 1 and Group 2, respectively. Mean body weights (±SE) at termination were: 31.2±0.99 and 30.1±0.75 for Group 1 and Group 2, respectively. Table 23 summarizes the mean body weights (±SE) for entire study. On day 14 of dosing, the mean tumor size (±SE) for control was 287.30±33.94 versus 318.74+29.76 for treatment group. Table 24 summarizes the tumor volumes (±SE) for entire study.

TABLE 23

Mean body weights ± S.E.

| Treatment | 2/19 | 2/24 | 2/27 | 3/2 | 3/6 | 3/10 |
|---|---|---|---|---|---|---|
| Vehicle Control | 31.0 ± 0.83 | 32.1 ± 0.76 | 31.9 ± 0.66 | 32.1 ± 0.68 | 32.0 ± 0.71 | 32.5 ± 0.88 |
| Anti-STAT3 | 29.2 ± 0.71 | 30.3 ± 0.75 | 30.4 ± 0.79 | 29.9 ± 0.72 | 30.6 ± 0.74 | 30.6 ± 0.77 |

The tumor doubling times were as follows: Group 1: 22.44 days; and Group 23.02 days. Anti-STAT3 bacterial VHH13 (SEQ ID NO:3) sdAb showed no significant growth inhibition in the PANC-1 human pancreatic cancer model system.

TABLE 24

Individual Tumor Measurements (mm³) for the PANC-1 xenograft Model

| Group | Animal # | 2/19 | 2/24 | 2/27 | 3/2 | 3/6 | 3/10 |
|---|---|---|---|---|---|---|---|
| 1 | 1 | 99.77 | 117.96 | 134.67 | 161.27 | 160.79 | 195.58 |
|  | 2 | 117.54 | 137.14 | 221.14 | 241.27 | 303.70 | 321.45 |
|  | 3 | 120.30 | 210.99 | 276.05 | 322.17 | 394.96 | 732.07 |
|  | 4 | 111.65 | 135.91 | 215.87 | 340.97 | 334.08 | 382.06 |
|  | 5 | 90.88 | 96.35 | 165.26 | 156.28 | 223.17 | 314.97 |
|  | 6 | 107.05 | 156.56 | 192.98 | 324.34 | 307.13 | 573.99 |
| Mean |  | 107.87 | 142.49 | 201.00 | 257.72 | 287.30 | 420.02 |
| S.E. |  | 11.11 | 16.01 | 20.00 | 34.35 | 33.94 | 80.34 |
| 2 | 7 | 96.31 | 193.71 | 275.06 | 317.53 | 395.37 | 540.66 |
|  | 8 | 89.24 | 90.03 | 112.43 | 125.51 | 189.63 | 235.08 |
|  | 9 | 80.62 | 148.97 | 196.38 | 187.24 | 299.84 | 530.46 |
|  | 10 | 108.03 | 144.14 | 234.46 | 240.39 | 288.75 | 421.61 |
|  | 11 | 77.66 | 116.21 | 313.19 | 290.38 | 411.66 | 197.67 |
|  | 12 | 129.68 | 143.20 | 290.67 | 224.92 | 261.44 | 343.04 |
|  | 13 | 108.99 | 182.30 | 239.00 | 254.64 | 342.19 | 464.00 |
|  | 14 | 123.27 | 171.03 | 223.34 | 226.88 | 248.69 | 324.30 |
|  | 15 | 144.53 | 136.03 | 198.47 | 226.04 | 247.97 | 273.58 |
|  | 16 | 120.96 | 136.48 | 226.43 | 338.06 | 564.71 | 883.81 |
|  | 17 | 112.69 | 144.76 | 167.12 | 225.70 | 223.06 | 326.19 |
|  | 18 | 134.95 | 189.64 | 193.14 | 248.01 | 351.63 | 364.44 |
| Mean |  | 110.58 | 149.71 | 222.47 | 242.11 | 318.74 | 408.74 |
| S.E. |  | 6.18 | 8.79 | 15.90 | 16.30 | 29.76 | 53.25 |
| P-value |  | 0.78 | 0.67 | 0.43 | 0.64 | 0.53 | 0.91 |

Example 10: MDA-MB-231 Xenograft Study

In this Example, the efficacy of anti-STAT3 bacterial VHH13 (SEQ ID NO:3) sdAb in the MDA-MB-231 human breast xenograft model was further evaluated. The dosing schedules were as follows: Group 1 (n=4; PBS; IP) twice a day for 14 days [BID×14]; Group 2 (n=4; 1 mg/kg bw; IP), twice a day for 14 days [BID×14]; Group 3 (n=4; 2 mg/kg bw; IP) twice a day for 14 days [BID×14]; and Group 4 (n=4; 2 mg/kg bw; IP) once a day for 14 days [QD×14]. An observation period of 7 days followed administration.

The human breast cancer cell lines MDA-MB-231 and athymic nude-Foxnl$^{nu}$ female mice were described above.

MDA-MB-231 cells at a density of 5×10$^6$ were injected subcutaneously into the right flank of the mice at a final volume of 100-μL in MEM media. Tumor measurements were initiated as soon as the tumors were palpable. Thereafter, tumors were measured twice weekly. Animals are randomized when tumors reach a range size of 55 to 150 mm$^3$ using the stratified random sampling algorithm. Treatment (anti-STAT3 bacterial VHH13 (SEQ ID NO:3) sdAb) or Vehicle (PBS) was initiated the day following randomization.

The randomization Mean (±SE) tumor size was: 92.08±13.24, 82.38±5.17, 77.47±7.17, and 104.71±14.64 for Groups 1, 2, 3, and 4 respectively. As shown in Table 25, mean body weights (±SE) at randomization were: 23.65±0.72, 23.45±0.66, 23.10±0.20, and 22.45±1.25 for Groups 1, 2, 3, and 4, respectively.

As shown in Table 26, at day 14 of dosing, the mean tumor size (±SE) for control group was 221.51±57.32 versus 67.12±10.66, 58.27±22.54, and 131.44±22.86, for treatment group 2, 3, and 4, respectively. At the time of termination (day 42) mean tumor size (±S.E.) was: 255.42±65.46, 55.98±6.94, 41.15±13.21, and 145.51±52.32, for groups 1, 2, 3, and 4, respectively. Mean body weights (±SE) at termination were: 24.80±0.49, 23.25±1.20, 24.00±0.32, and 23.2±1.46 for Groups 1, 2, 3, and 4, respectively. The max mean % net weight loss (day) was: 0.7 (36), 1.5 (23), 1.8 (36), and 2.2 (29) for Groups 1, 2, 3, and 4, respectively.

Also as shown in Table 26, the mean growth inhibition in the treatment groups was 78.3, 75.2, and 55.9, for Groups 2, 3, and 4, respectively. The tumor doubling times were: Group 1: 20.56 days; Group 2: 34.54 days; Group 3: 30.07 days; and Group 4: 27.17 days. There was a growth delay of 13.99, 9.52, and 6.61 days for Groups 2, 3 and 4, respectively. The % treatment/control values for treatment groups were: Group 2: −33.75 (tumor stasis); Group 3: −54.4 (tumor regression); and Group 4: 10.28 (tumor inhibition). FIG. 6 illustrates the growth inhibition of anti-STAT3 bacterial VHH13 (SEQ ID NO:3) sdAb in the MDA-MB-231 xenograft model.

Administration of anti-STAT3 bacterial VHH13 (SEQ ID NO:3) sdAb was associated with a significant growth inhibition in Group 2 (p=0.02) [1 mg/kg; BID×14] and Group 3 (p=0.02) [2 mg/kg; BID×14]. Furthermore, three out of four tumors showed significant regression. Based on these data, it is concluded that anti-STAT3 bacterial VHH13 (SEQ ID NO:3) sdAb has chemotherapeutic activity in the MDA-MB-231 human breast cancer model system.

TABLE 25

Mean Body Weights ± S.E.

| | | Dosing | | | | | Recovery | |
|---|---|---|---|---|---|---|---|---|
| | | 6/23 | 6/26 | 6/29 | 7/2 | 7/6 | 7/9 | 7/15 |
| Group | Schedule | 20 | 23 | 26 | 29 | 33 | 36 | 42 |
| 1 | PBS; BID × 14 | 23.65 ± 0.72 | 23.85 ± 0.60 | 24.18 ± 0.67 | 24.05 ± 0.63 | 24.30 ± 0.67 | 24.13 ± 0.72 | 24.80 ± 0.49 |
| 2 | 1 mg/kg; BID × 14 | 23.45 ± 0.66 | 23.10 ± 0.68 | 23.13 ± 0.74 | 23.13 ± 0.95 | 23.08 ± 1.01 | 23.13 ± 1.09 | 23.25 ± 1.20 |
| 3 | 2 mg/kg; BID × 14 | 23.10 ± 0.20 | 23.10 ± 0.14 | 23.20 ± 0.07 | 23.85 ± 0.39 | 23.80 ± 0.24 | 23.38 ± 0.23 | 24.00 ± 0.32 |
| 4 | 2 mg/kg; QD × 14 | 22.45 ± 1.25 | 22.35 ± 1.32 | 22.58 ± 1.46 | 22.08 ± 1.44 | 22.73 ± 1.47 | 22.55 ± 1.46 | 23.20 ± 1.38 |

TABLE 26

Individual Tumor Measurements (mm$^3$) for the MDA-MB-231 Xenograft Model

| | Animal # | Jun. 23, 2015 (20) | Jun. 26, 2015 (23) | Jun. 29, 2015 (26) | Jul. 2, 2015 (29) | Jul. 6, 2015 (33) | Jul. 9, 2015 (36) | Jul. 15, 2015 (42) |
|---|---|---|---|---|---|---|---|---|
| Group 1 | 001 | 93.38 | 119.07 | 159.80 | 197.91 | 210.95 | 243.31 | 265.61 |
| | 002 | 116.07 | 241.31 | 313.16 | 339.13 | 362.30 | 390.48 | 426.32 |
| | 003 | 55.67 | 83.45 | 98.22 | 135.50 | 198.19 | 204.96 | 218.29 |
| | 004 | 104.82 | 112.09 | 118.44 | 111.07 | 114.61 | 115.31 | 111.45 |
| Mean Absolute | | 92.49 | 138.98 | 172.41 | 195.90 | 221.51 | 238.51 | 255.42 |
| Mean Relative | | 100.00% | 150.27% | 186.41% | 211.82% | 239.51% | 257.89% | 276.17% |
| S.E. Mean | | 13.12 | 34.97 | 48.64 | 51.12 | 51.56 | 57.32 | 65.46 |
| % Inhibition Mean | | | | | | | | |
| Median Absolute | | 99.10 | 115.58 | 139.12 | 166.71 | 204.57 | 224.13 | 241.95 |
| Median Relative | | 100.00% | 116.62% | 140.38% | 168.22% | 206.42% | 226.16% | 244.14% |
| S.E. Median | | 13.66 | 37.49 | 52.30 | 53.83 | 52.48 | 57.91 | 65.92 |
| % Inhibition Median | | | | | | | | |
| Group 2 | 005 | 73.15 | 54.54 | 59.17 | 57.21 | 56.20 | 37.13 | 39.17 |
| | 006 | 80.11 | 76.56 | 80.34 | 88.75 | 99.09 | 87.42 | 72.18 |
| | 007 | 97.22 | 79.99 | 78.44 | 59.90 | 55.90 | 53.66 | 60.35 |
| | 008 | 81.21 | 53.58 | 54.34 | 67.43 | 57.30 | 29.02 | 52.23 |

TABLE 26-continued

Individual Tumor Measurements (mm³) for the MDA-MB-231 Xenograft Model

| | Animal # | Jun. 23, 2015 (20) | Jun. 26, 2015 (23) | Jun. 29, 2015 (26) | Jul. 2, 2015 (29) | Jul. 6, 2015 (33) | Jul. 9, 2015 (36) | Jul. 15, 2015 (42) |
|---|---|---|---|---|---|---|---|---|
| Mean Absolute | | 82.92 | 66.17 | 68.07 | 68.32 | 67.12 | 51.81 | 55.98 |
| Mean Relative | | 100.00% | 79.79% | 82.09% | 82.39% | 80.95% | 62.48% | 67.51% |
| S.E. Mean | | 5.09 | 7.03 | 6.62 | 7.14 | 10.66 | 12.93 | 6.94 |
| % Inhibition Mean | | 10.34% | 52.39% | 60.52% | 65.12% | 69.70% | 78.28% | 78.08% |
| Median Absolute | | 80.66 | 65.55 | 68.80 | 63.66 | 56.75 | 45.40 | 56.29 |
| Median Relative | | 100.00% | 81.27% | 85.30% | 78.93% | 70.36% | 56.28% | 69.79% |
| S.E. Median | | 5.25 | 7.04 | 6.63 | 7.63 | 12.23 | 13.45 | 6.94 |
| % Inhibition Median | | 18.61% | 43.28% | 50.54% | 61.81% | 72.26% | 79.75% | 76.74% |
| Group 3 | 009 | 56.41 | 43.61 | 33.13 | 31.76 | 34.11 | 50.33 | 18.94 |
| | 010 | 84.06 | 85.18 | 61.75 | 80.69 | 110.72 | 89.11 | 73.89 |
| | 011 | 82.87 | 54.78 | 34.92 | 54.38 | 78.47 | 78.68 | 51.30 |
| | 012 | 86.73 | 44.01 | 23.09 | 16.99 | 9.78 | 18.71 | 20.48 |
| Mean Absolute | | 77.52 | 56.89 | 38.22 | 45.95 | 58.27 | 59.21 | 41.15 |
| Mean Relative | | 100.00% | 73.39% | 49.31% | 59.28% | 75.17% | 76.38% | 53.09% |
| S.E. Mean | | 7.08 | 9.78 | 8.26 | 13.90 | 22.54 | 15.79 | 13.21 |
| % Inhibition Mean | | 16.19% | 59.06% | 77.83% | 76.54% | 73.69% | 75.18% | 83.89% |
| Median Absolute | | 83.46 | 49.39 | 34.02 | 43.07 | 56.29 | 64.51 | 35.89 |
| Median Relative | | 100.00% | 59.18% | 40.76% | 51.60% | 67.44% | 77.29% | 43.00% |
| S.E. Median | | 7.87 | 10.69 | 8.61 | 14.00 | 22.56 | 16.08 | 13.56 |
| % Inhibition Median | | 15.78% | 57.27% | 75.54% | 74.17% | 72.49% | 71.22% | 85.17% |
| Group 4 | 013 | 88.56 | 108.35 | 105.80 | 102.94 | 183.39 | 159.78 | 291.06 |
| | 014 | 78.73 | 51.51 | 54.20 | 70.39 | 84.29 | 55.83 | 42.03 |
| | 015 | 113.20 | 85.29 | 69.30 | 103.16 | 103.20 | 87.15 | 130.64 |
| | 016 | 141.91 | 130.82 | 87.49 | 145.68 | 154.89 | 117.63 | 118.31 |
| Mean Absolute | | 105.60 | 93.99 | 79.20 | 105.54 | 131.44 | 105.10 | 145.51 |
| Mean Relative | | 100.00% | 89.01% | 75.00% | 99.94% | 124.47% | 99.52% | 137.79% |
| S.E. Mean | | 14.11 | 16.94 | 11.18 | 15.44 | 22.86 | 22.17 | 52.32 |
| % Inhibition Mean | | −14.18% | 32.37% | 54.06% | 46.13% | 40.66% | 55.94% | 43.03% |
| Median Absolute | | 100.88 | 96.82 | 78.40 | 103.05 | 129.05 | 102.39 | 124.47 |
| Median Relative | | 100.00% | 95.98% | 77.71% | 102.15% | 127.92% | 101.49% | 123.38% |
| S.E. Median | | 14.37 | 17.02 | 11.19 | 15.50 | 22.90 | 22.22 | 53.72 |
| % Inhibition Median | | −1.80% | 16.23% | 43.65% | 38.19% | 36.92% | 54.32% | 48.55% |

Example 11: Efficacy of Anti-STAT3 Bacterial VHH13 (SEQ ID NO:3) SDAB on Three Human Cancer Xenograft Models In this Example, the efficacy of anti-STAT3 bacterial VHH13 (SEQ ID NO:3) sdAb was evaluated in the MDA-MB-231 Human Breast, PANC-1 Pancreatic, and DU145 Prostate cancer xenograft models.

Athymic Nude-Foxnl$^{nu}$ mice, MDA-MB-231 breast cancer cells, PANC-1 pancreatic cancer and the DU145 prostate cancer cell lines were described above. The body weight of the mice ranged from 17 to 19 g (34 females) and 21 to 23 g (16 males) on Day 1 of the study.

Cells in early passages (4 to 10) were used for implantation into the mice and were harvested during log phase growth. MDA-MB-231 (5×10⁶), DU145 (5×10⁶), and PANC-1 (1.5×10⁶) were injected subcutaneously into the right flank of the mice at a final volume of 100-µL of media. Tumor measurements were initiated as soon as the tumors were palpable. Thereafter, tumors were measured twice weekly.

Animals were randomized using the stratified random sampling algorithm when tumors reach a range size of: 74-120 mm³ (MDA-MB-231), 89-146 mm³ (DU145), or 60-160 mm³ (PANC-1). Treatment (containing anti-STAT3 bacterial VHH13 (SEQ ID NO:3) sdAb and referred to herein as SBT-100) or Vehicle (PBS) was initiated the day following randomization, referred to as day 1.

Anti-STAT3 bacterial VHH13 (SEQ ID NO:3) sdAb was supplied as a pre-formulated solution at a concentration of 0.651 mg/ml and was stored at −20° C. until ready to use. The stock solution was diluted in sterile PBS pH 7.6 to provide a 5 mg/kg in a dosing volume of 10 mL/kg. The working solution was prepared every 7 days, aliquoted onto seven vials and stored at 4° C. On each day of treatment, only the needed vial was brought to room temperature. All leftover sdAb material was retained at 4° C. as need for the next dose. At day 8, any remaining sdAb material was discarded and a fresh batch prepared.

Two groups (control and SBT-100) of mice per tumor model were dosed according to the protocol shown in Table 27. Dosing schedules were as follows: Group 1 (n=4; PBS) twice a day for 14 days [BID×14]; Group 2 (n=4; SBT-100, 5 mg/kg bw), twice a day for 14 days [BID×14]. Both the vehicle (PBS pH 7.6) and SBT100 were administered intraperitoneally (i.p.) twice a day, six hours apart for fourteen days. Dosing was conducted according to individual animal weights. A recovery period of 7 days followed administration.

TABLE 27

Experimental Design of Xenograft Study

| Model | # of cells inoculated/mouse | Group | # Mice | Agent | Dose (mg/Kg) | Route | Schedule |
|---|---|---|---|---|---|---|---|
| MDA-MB-231 | $5 \times 10^8$ | 1 | 4 | Control (PBS) | 0 | IP | BID × 14 |
|  |  | 2 | 4 | SBT-100 | 5 | IP | BID × 14 |
| PANC-1 | $1.5 \times 10^8$ | 1 | 4 | Control (PBS) | 0 | IP | BID × 14 |
|  |  | 2 | 4 | SBT-100 | 5 | IP | BID × 14 |
| DU145 | $5 \times 10^8$ | 1 | 4 | Control (PBS) | 0 | IP | BID × 14 |
|  |  | 2 | 4 | SBT-100 | 5 | IP | BID × 14 |

Study Log Study Director Animal Study Management Software (San Francisco, Calif.) was used to randomize animals, collect data (e.g., dosing, body weights, tumors measurements, clinical observations), and conduct data analyses.

In the MDA-MB-231 tumor xenograft model, animals were randomized on day 23 post-inoculation with a mean (±SE) tumor size of: 77.98±21.58 and 84.71±5.56 for Groups 1 and 2, respectively. Mean body weights (±SE) at randomization were: 20.04±0.62 and 23.7±1.84 for Groups 1 and 2, respectively. Table 28 summarizes the mean body weights (±SE) for entire study. At last day of dosing (Day 14), the mean tumor size (±SE) for control group was 168.28±51.57 versus 83.81±22.65 for SBT-100 treated mice. Table 29 summarizes the tumor volumes (±SE) for entire study. At the time of termination (day 28) mean tumor size (±S.E.) was: 270.49±112.35 and 91.72±33.17, for Groups 1 and 2, respectively. Mean body weights (±SE) at termination were: 25.36±1.07 and 24.25±1.68 for Groups 1 and 2, respectively. At the end of the study, the mean tumor growth inhibition in the SBT-100 treated group was 85.8% (p=0.006). FIG. 7 illustrates the mean tumor volume. The tumor doubling times were 25.78 days versus 111.6 days for Group 1 and Group 2, respectively. The % treatment/control for Group 2 was 13.35 (tumor inhibition).

TABLE 28

Mean Body Weights for Mice in MDA-MB-231

| Group | Animal ID | Phase Dosing 8/28 | 9/1 | 9/4 | 9/8 | 9/11 | Recovery 9/15 | 9/18 |
|---|---|---|---|---|---|---|---|---|
| Control | 001 | 23.40 | 24.80 | 24.60 | 25.00 | 24.70 | 23.30 | 25.10 |
| Control | 002 | 22.40 | 22.50 | 22.60 | 22.70 | 22.80 | 20.60 | 23.10 |
| Control | 003 | 23.70 | 24.80 | 25.20 | 24.80 | 24.30 | 23.30 | 25.20 |
| Control | 004 | 23.70 | 24.70 | 25.10 | 25.30 | 24.90 | 22.90 | 25.40 |
| Mean |  | 23.30 | 24.20 | 24.38 | 24.45 | 24.18 | 22.53 | 24.70 |
| Median |  | 23.55 | 24.75 | 24.85 | 24.90 | 24.50 | 23.10 | 25.15 |
| SD |  | 0.62 | 1.13 | 1.21 | 1.18 | 0.95 | 1.30 | 1.07 |
| % Change |  | 0.00 | 3.82 | 4.56 | 4.89 | 3.73 | −3.38 | 5.97 |
| SBT-100 | 005 | 21.70 | 21.70 | 21.70 | 22.40 | 22.60 | 21.40 | 22.20 |
| SBT-100 | 006 | 25.00 | 24.30 | 24.30 | 24.70 | 25.30 | 24.40 | 25.00 |
| SBT-100 | 007 | 22.60 | 23.00 | 23.10 | 23.10 | 23.80 | 22.80 | 23.70 |
| SBT-100 | 008 | 26.50 | 25.30 | 25.50 | 26.10 | 25.80 | 25.60 | 26.10 |
| Mean |  | 23.7 | 23.575 | 23.65 | 24.075 | 24.375 | 23.55 | 24.25 |
| Median |  | 23.8 | 23.65 | 23.7 | 23.9 | 24.55 | 23.6 | 24.35 |
| SD |  | 1.84 | 1.56 | 1.63 | 1.66 | 1.46 | 1.84 | 1.68 |
| % Change |  | 0.00 | −0.45 | −0.15 | 1.65 | 2.96 | −0.63 | 2.38 |

TABLE 29

Tumor Volumes for MDA-MB-231

| Group | Animal ID | Pre-Dosing 8/21 | 8/24 | 8/27 | Dosing 8/28 | 9/1 | 9/4 | 9/8 | 9/11 | Recovery 9/15 | 9/18 |
|---|---|---|---|---|---|---|---|---|---|---|---|
| Control | 001 | 51.00 | 55.80 | 80.94 | 76.35 | 83.66 | 94.11 | 110.78 | 129.99 | 162.81 | 184.15 |
| Control | 002 | 75.19 | 77.22 | 121.13 | 120.73 | 145.12 | 179.21 | 203.16 | 234.05 | 308.70 | 428.44 |
| Control | 003 | 57.04 | 57.81 | 75.32 | 81.06 | 93.25 | 114.27 | 181.87 | 242.88 | 295.93 | 408.67 |
| Control | 004 | 42.92 | 51.67 | 106.54 | 92.23 | 116.96 | 142.60 | 191.58 | 213.48 | 296.91 | 303.19 |
| Mean |  | 56.54 | 60.63 | 95.98 | 92.59 | 109.75 | 132.55 | 171.84 | 205.10 | 263.59 | 331.11 |
| Median |  | 54.02 | 56.80 | 93.74 | 86.64 | 105.10 | 128.44 | 186.72 | 223.76 | 291.42 | 355.93 |
| SD |  | 13.71 | 11.36 | 21.58 | 19.91 | 27.42 | 36.92 | 41.83 | 51.57 | 67.78 | 112.35 |
| SBT-100 | 005 | 72.25 | 64.45 | 80.02 | 74.07 | 56.81 | 49.44 | 68.70 | 73.04 | 93.32 | 116.07 |
| SBT-100 | 006 | 61.60 | 63.06 | 80.67 | 79.60 | 71.92 | 67.08 | 87.64 | 115.80 | 116.97 | 120.44 |
| SBT-100 | 007 | 37.41 | 35.15 | 91.93 | 91.85 | 50.02 | 50.32 | 46.10 | 63.85 | 66.57 | 80.57 |

TABLE 29-continued

Tumor Volumes for MDA-MB-231

| Group | Animal ID | Pre-Dosing | | | Dosing | | | | | Recovery | |
|---|---|---|---|---|---|---|---|---|---|---|---|
| | | 8/21 | 8/24 | 8/27 | 8/28 | 9/1 | 9/4 | 9/8 | 9/11 | 9/15 | 9/18 |
| SBT-100 | 008 | 43.80 | 56.96 | 86.22 | 79.94 | 69.23 | 60.19 | 54.10 | 82.57 | 79.47 | 49.78 |
| Mean | | 53.74 | 54.91 | 84.71 | 81.37 | 59.49 | 56.76 | 64.11 | 83.81 | 89.08 | 91.72 |
| Median | | 52.65 | 60.02 | 83.45 | 79.77 | 58.02 | 55.25 | 61.40 | 77.81 | 86.40 | 98.32 |
| SD | | 18.00 | 13.57 | 6.56 | 7.49 | 9.16 | 0.43 | 18.21 | 22.65 | 21.56 | 33.17 |
| % T/C | | 0.0 | 32.3 | 84.0 | 81.6 | 13.6 | 5.9 | 9.2 | 20.7 | 17.6 | 13.4 |
| p-value | | | 0.800 | 0.542 | 0.351 | 0.332 | 0.013 | 0.007 | 0.003 | 0.005 | 0.003 | 0.006 |

In the DU145 tumor xenograft model, animals were randomized on day 17 post-inoculation with a mean (±SE) tumor size of: 111.87±20.53 and 111.23±25.16 for Groups 1 and 2, respectively. Mean body weights (±SE) at randomization were: 29.10±1.94 and 30.68±1.56 for Groups 1 and 2, respectively. Table 30 summarizes the mean body weights (±SE) for entire study. At last day of dosing (Day 14), the mean tumor size (±SE) for control group was 621.81±276.25 versus 364.14±51.64 for SBT-100 treated mice. Table 31 summarizes the tumor volumes (±SE) for entire study. At the time of termination (day 28) mean tumor size (±S.E.) was: 819.42±351.88 and 601.83±131.51, for Groups 1 and 2, respectively. Mean body weights (±SE) at termination were: 29.20±2.33 and 29.60±1.04 for Groups 1 and 2, respectively. At the end of the study, the mean tumor growth inhibition in the SBT-100 treated group was 26.6% (p=0.29). FIG. 8 illustrates the mean tumor volume. The tumor doubling times were 14.57 days versus 18.19 days for Group 1 and Group 2, respectively. The % treatment/control for Group 2 was 74.8.

TABLE 30

Mean Body Weights for Mice in DU145

| Group | Animal ID | Dosing | | | | | Recovery | |
|---|---|---|---|---|---|---|---|---|
| | | 9/4 | 9/8 | 9/11 | 9/15 | 9/18 | 9/22 | 9/25 |
| Control | 001 | 29.60 | 28.10 | 29.30 | 28.40 | 28.30 | 29.00 | 29.90 |
| Control | 002 | 29.70 | 30.10 | 31.20 | 30.10 | 30.40 | 29.90 | 30.00 |

TABLE 30-continued

Mean Body Weights for Mice in DU145

| Group | Animal ID | Dosing | | | | | Recovery | |
|---|---|---|---|---|---|---|---|---|
| | | 9/4 | 9/8 | 9/11 | 9/15 | 9/18 | 9/22 | 9/25 |
| Control | 003 | 30.80 | 30.10 | 31.00 | 31.70 | 31.20 | 31.10 | 31.10 |
| Control | 004 | 26.30 | 25.70 | 26.60 | 25.20 | 26.10 | 26.20 | 25.80 |
| Mean | | 29.10 | 29.50 | 29.53 | 28.85 | 29.00 | 29.05 | 29.20 |
| Median | | 29.65 | 29.10 | 30.15 | 29.25 | 29.35 | 29.45 | 29.95 |
| SD | | 1.94 | 2.09 | 2.13 | 2.78 | 2.29 | 2.09 | 2.33 |
| % Change | | 0.00 | -2.07 | 1.46 | -0.99 | -0.37 | -0.19 | 0.27 |
| SBT-100 | 005 | 30.90 | 30.20 | 27.90 | 29.80 | 29.90 | 30.50 | 30.10 |
| SBT-100 | 006 | 28.40 | 26.20 | 27.30 | 26.90 | 27.50 | 29.10 | 28.50 |
| SBT-100 | 007 | 31.70 | 31.20 | 31.50 | 30.40 | 30.70 | 31.20 | 30.80 |
| SBT-100 | 008 | 31.70 | 29.70 | 30.20 | 28.20 | 28.10 | 28.80 | 29.00 |
| Mean | | 30.68 | 29.33 | 29.23 | 28.83 | 29.05 | 29.90 | 29.60 |
| Median | | 31.30 | 29.95 | 29.05 | 29.00 | 29.00 | 29.80 | 29.55 |
| SD | | 1.56 | 2.17 | 1.97 | 1.58 | 1.50 | 1.14 | 1.04 |
| % Change | | 0.00 | -4.47 | -4.74 | -6.00 | -5.23 | -2.39 | -3.40 |

TABLE 31

Tumor Volumes for DU145

| Group | Animal ID | Pre-Dosing | | | | Dosing | | | | | Recovery | |
|---|---|---|---|---|---|---|---|---|---|---|---|---|
| | | 8/24 | 8/27 | 8/31 | 9/3 | 9/4 | 9/8 | 9/11 | 9/15 | 9/18 | 9/22 | 9/25 |
| Control | 001 | 38.18 | 41.27 | 38.41 | 82.60 | 83.22 | 121.16 | 203.79 | 310.41 | 409.15 | 430.31 | 450.69 |
| Control | 002 | 45.05 | 35.99 | 64.98 | 96.50 | 103.83 | 135.42 | 225.62 | 327.76 | 478.14 | 534.48 | 599.97 |
| Control | 003 | 49.65 | 22.37 | 88.76 | 127.98 | 141.49 | 213.24 | 334.15 | 930.74 | 1,023.13 | 1,084.00 | 1,188.93 |
| Control | 004 | 17.06 | 36.44 | 86.73 | 131.20 | 138.33 | 227.23 | 289.78 | 338.79 | 576.83 | 926.90 | 1,027.90 |
| Mean | | 38.98 | 34.02 | 64.47 | 111.87 | 119.22 | 174.26 | 275.84 | 476.93 | 621.81 | 743.95 | 819.42 |
| Median | | 42.11 | 36.22 | 65.36 | 111.74 | 121.98 | 174.33 | 257.70 | 333.27 | 527.49 | 730.59 | 813.93 |
| SD | | 13.67 | 8.12 | 20.58 | 20.53 | 24.32 | 53.70 | 80.91 | 302.77 | 276.25 | 311.67 | 351.98 |
| SBT-100 | 005 | 33.80 | 23.32 | 35.67 | 86.02 | 89.21 | 151.52 | 145.67 | 386.92 | 325.88 | 474.31 | 496.83 |
| SBT-100 | 006 | 59.44 | 41.00 | 64.21 | 98.56 | 121.39 | 148.44 | 208.10 | 357.62 | 391.02 | 518.25 | 588.67 |
| SBT-100 | 007 | 42.20 | 35.11 | 77.90 | 144.66 | 145.78 | 115.05 | 106.70 | 248.12 | 316.24 | 454.78 | 528.83 |
| SBT-100 | 008 | 63.37 | 50.18 | 71.23 | 116.28 | 118.70 | 134.16 | 147.52 | 320.22 | 423.45 | 604.72 | 793.96 |
| Mean | | 51.23 | 37.40 | 59.75 | 111.23 | 118.77 | 137.39 | 151.50 | 328.22 | 364.14 | 513.01 | 601.83 |
| Median | | 50.87 | 38.06 | 82.72 | 107.42 | 120.05 | 141.30 | 146.80 | 338.92 | 368.43 | 496.20 | 558.76 |

TABLE 31-continued

Tumor Volumes for DU145

| | | Pre-Dosing | | | | Dosing | | | | Recovery | |
|---|---|---|---|---|---|---|---|---|---|---|---|
| Group | Animal ID | 8/24 | 8/27 | 8/31 | 9/3 | 9/4 | 9/8 | 9/11 | 9/15 | 9/18 | 9/22 | 9/25 |
| SD | | 15.13 | 11.25 | 18.90 | 25.18 | 23.17 | 16.78 | 40.98 | 59.97 | 51.64 | 66.65 | 131.51 |
| % T/C | | | 0.0 | −26.8 | 29.1 | 78.8 | 81.7 | 65.4 | 42.1 | 70.6 | 56.9 | 69.9 | 74.8 |
| p-value | | | 0.226 | 0.643 | 0.747 | 0.970 | 0.990 | 0.238 | 0.034 | 0.372 | 0.115 | 0.197 | 0.291 |

In the PANC-1 tumor xenograft model, animals were randomized on day 22 post-inoculation with a mean (±SE) tumor size of: 78.74±40.21 and 93.84±36.31 for Groups 1 and 2, respectively. Mean body weights (±SE) at randomization were: 22.50±1.47 and 24.23±1.63 for Groups 1 and 2, respectively. Table 32 summarizes the mean body weights (±SE) for entire study. At last day of dosing (Day 14), the mean tumor size (±SE) for control group was 204.95±178.90 versus 159.03±28.01 for SBT-100 treated mice. Table 33 summarizes the tumor volumes (±SE) for entire study. At the time of termination (day 28) mean tumor size (±S.E.) was: 284.77±288.88 and 203.02±30.34, for groups 1 and 2, respectively. Mean body weights (±SE) at termination were: 27.38±1.07 and 26.23±1.19 for Groups 1 and 2, respectively. At the end of the study, the mean tumor growth inhibition in the SBT-100 treated group was 41.78% (p=0.35). FIG. 9 illustrates the mean tumor volume. The tumor doubling times were 18.51 days versus 35.70 days for Group 1 and Group 2, respectively. The % treatment/control for Group 2 was 52.79.

TABLE 32

Mean Body Weights for Mice in PANC-1

| | | Dosing | | | | | Recovery | |
|---|---|---|---|---|---|---|---|---|
| Group | Animal ID | 9/9 | 9/11 | 9/15 | 9/18 | 9/22 | 9/25 | 9/29 |
| Control | 001 | 26.50 | 26.60 | 25.60 | 27.10 | 25.70 | 26.10 | 27.20 |
| Control | 002 | 24.30 | 24.60 | 23.90 | 25.10 | 24.40 | 25.00 | 25.60 |

TABLE 32-continued

Mean Body Weights for Mice in PANC-1

| | | Dosing | | | | | Recovery | |
|---|---|---|---|---|---|---|---|---|
| Group | Animal ID | 9/9 | 9/11 | 9/15 | 9/18 | 9/22 | 9/25 | 9/29 |
| Control | 003 | 27.60 | 26.50 | 26.30 | 26.20 | 26.10 | 27.60 | 28.20 |
| Control | 004 | 25.10 | 25.30 | 24.20 | 25.10 | 24.70 | 25.90 | 26.90 |
| Mean | | 22.50 | 22.80 | 23.04 | 24.30 | 24.58 | 25.90 | 27.38 |
| Median | | 25.60 | 25.90 | 25.00 | 25.65 | 25.20 | 26.00 | 27.05 |
| SD | | 1.47 | 0.97 | 1.18 | 0.97 | 0.81 | 1.03 | 1.07 |
| % Change | | 0.00 | −0.39 | −3.15 | 0.12 | −2.41 | 1.05 | 4.33 |
| SBT-100 | 005 | 22.60 | 22.80 | 21.40 | 22.60 | 22.60 | 22.90 | 24.60 |
| SBT-100 | 006 | 26.00 | 25.10 | 24.90 | 25.70 | 25.10 | 25.40 | 27.10 |
| SBT-100 | 007 | 23.10 | 22.30 | 22.40 | 22.70 | 23.10 | 23.50 | 25.70 |
| SBT-100 | 008 | 26.20 | 26.00 | 25.20 | 25.40 | 26.20 | 25.40 | 27.30 |
| Mean | | 24.23 | 23.80 | 23.48 | 24.08 | 24.25 | 24.30 | 26.23 |
| Median | | 24.15 | 23.90 | 23.65 | 24.05 | 24.10 | 24.45 | 26.40 |
| SD | | 1.63 | 1.46 | 1.87 | 1.71 | 1.69 | 1.29 | 1.19 |
| % Change | | 0.00 | −1.71 | −3.14 | −0.63 | 0.13 | 0.39 | 8.39 |

TABLE 33

Tumor Volumes for PANC-1

| | | Pre-Dosing | | | Dosing | | | | | Recovery | |
|---|---|---|---|---|---|---|---|---|---|---|---|
| Group | Animal ID | 8/31 | 9/3 | 9/8 | 9/9 | 9/11 | 9/15 | 9/18 | 9/22 | 9/25 | 9/29 |
| Control | 001 | 54.91 | 56.79 | 94.23 | 94.37 | 94.69 | 123.90 | 136.77 | 206.74 | 220.31 | 223.91 |
| Control | 002 | 46.38 | 75.43 | 81.99 | 81.62 | 88.44 | 130.01 | 161.06 | 140.52 | 146.62 | 202.22 |
| Control | 003 | 0.00 | 27.50 | 57.30 | 59.60 | 99.77 | 107.00 | 142.23 | 140.55 | 168.68 | 187.27 |
| Control | 004 | 0.00 | 0.00 | 152.17 | 159.98 | 227.02 | 380.54 | 502.66 | 514.93 | 574.44 | 781.45 |
| Mean | | 20.26 | 32.54 | 78.74 | 80.91 | 104.18 | 151.29 | 189.83 | 204.95 | 226.81 | 284.77 |
| Median | | 23.19 | 42.15 | 88.11 | 87.99 | 97.23 | 126.95 | 146.64 | 173.65 | 194.50 | 213.06 |
| SD | | 29.45 | 33.13 | 40.21 | 43.18 | 66.52 | 130.48 | 179.63 | 178.90 | 200.56 | 288.88 |
| SBT-100 | 005 | 39.60 | 64.75 | 76.44 | 78.07 | 57.54 | 93.17 | 112.98 | 140.09 | 173.92 | 245.84 |
| SBT-100 | 006 | 40.31 | 37.27 | 68.57 | 73.13 | 76.46 | 113.30 | 130.49 | 192.56 | 205.65 | 189.42 |
| SBT-100 | 007 | 85.71 | 91.27 | 147.61 | 149.02 | 123.96 | 116.01 | 157.50 | 171.29 | 176.68 | 200.97 |
| SBT-100 | 008 | 48.72 | 65.19 | 82.73 | 83.18 | 86.90 | 102.48 | 106.65 | 132.19 | 136.93 | 175.84 |
| Mean | | 53.58 | 62.12 | 83.84 | 95.85 | 86.21 | 106.24 | 126.65 | 158.03 | 173.28 | 203.02 |
| Median | | 44.51 | 59.97 | 79.59 | 80.62 | 81.68 | 107.89 | 121.73 | 155.69 | 174.80 | 195.19 |
| SD | | 21.82 | 22.62 | 36.31 | 35.69 | 27.94 | 10.49 | 23.06 | 28.01 | 28.10 | 30.34 |
| % T/C | | 0.0 | 0.0 | 42.6 | 44.2 | 27.4 | 34.4 | 38.0 | 49.7 | 51.0 | 52.6 |
| p-value | | 0.174 | 0.310 | 0.927 | 0.917 | 0.296 | 0.272 | 0.286 | 0.350 | 0.343 | 0.355 |

Example 12: Efficacy of Anti-STAT3 Bacterial VHH13 (SEQ ID NO:3) SDAB in the ER+/PR+(MCF-7) Human Breast Tumor Xenograft Model This Example demonstrates the efficacy of anti-STAT3 bacterial VHH13 (SEQ ID NO:3) sdAb in the MCF-7 human breast tumor xenograft model in nude mice.

Female athymic nude mice (Crl:NU(Ncr)-Foxnl$^{nu}$, Charles River) were twelve weeks old with a body weight (BW) range of 23.0 to 30.1 g on Day 1 of the study. The animals were fed and housed as described above.

MCF-7 human breast carcinoma cells were obtained and cultured as described above, and used for the mouse xenograph. Three days prior to tumor cell implantation, estrogen pellets (0.36 mg estradiol, 60-day release, Innovative Research of America, Sarasota, Fla.) were implanted subcutaneously between the scapulae of each test animal using a sterilized trocar.

The tumor cells used for implantation were harvested during log phase growth and resuspended in phosphate buffered saline (PBS) at a concentration of $1\times10^8$ cells/mL. On the day of implantation, each test mouse received $1\times10^7$ MCF-7 cells (0.1 mL cell suspension) implanted subcutaneously in the right flank and tumor growth was monitored as the average size approached the target range of 100-150 mm$^3$. Twenty-one days later, designated as Day 1 of the study, the animals were sorted into two groups each consisting of four mice with individual tumor volumes ranging from 108 to 144 mm$^3$ and group mean tumor volumes from 117 to 123 mm$^3$.

Anti-STAT3 bacterial VHH13 (SEQ ID NO:3) sdAb was provided as a pre-formulated ready to dose solution at a concentration 0.41867 mg/mL in 1 mL aliquots and were stored at −20° C. until needed. The 0.41867 mg/mL solution provided 1 mg/kg dosage in a dosing volume of 23.88 mL/kg. On each day of treatment, only needed vials of anti-STAT3 bacterial VHH13 (SEQ ID NO:3) sdAb were thawed to room temperature. All leftover dosing suspensions were retained at 4° C. as needed for the next dose.

Two groups of athymic nude mice were dosed according to the protocol shown in Table 34. All vehicle (control) and anti-STAT3 bacterial VHH13 (SEQ ID NO:3) sdAb doses were administered intraperitoneally (i.p.) three times daily, six hours apart for fourteen days, with two doses delivered on Day 1 and one dose delivered on the morning of Day 15 (tid×14, first day 2 doses). The dosing volume for vehicle and anti-STAT3 bacterial VHH13 (SEQ ID NO:3) sdAb was 0.478 mL per 20 grams of body weight (23.88 mL/kg) and was scaled to the body weight of each individual animal. Group 1 received the vehicle and served as the benchmark group for tumor engraftment and progression, as well as the control. Group 2 was given anti-STAT3 bacterial VHH13 (SEQ ID NO:3) sdAb at 1 mg/kg.

TABLE 34

Protocol Design for the Study

| | | Treatment Regimen | | | |
|---|---|---|---|---|---|
| Group | n | Agent | mg/kg | Route | Schedule |
| 1 | 4 | vehicle | — | ip | tid x 14 first Day 2 doses |
| 2 | 4 | VHH13 | 1 | ip | tid x 14 first Day 2 doses |

Tumors were measured twice weekly, and each animal was euthanized when its neoplasm reached the predetermined endpoint volume (1000 mm$^3$) or at the end of the study, day 39, whichever came first. When a tumor reached the endpoint volume, the animal was documented as euthanized for tumor progression (TP), with the date of euthanasia. The time to endpoint (TTE) for each mouse was calculated by the following equation:

$$TTE = \frac{\log_{10}(\text{endpoint volume}) - b}{m}$$

where TTE is expressed in days, endpoint volume is expressed in mm$^3$, b is the intercept, and m is the slope of the line obtained by linear regression of a log-transformed tumor growth data set. The data set consists of the first observation that exceeded the endpoint volume used in analysis and the three consecutive observations that immediately preceded the attainment of this endpoint volume. The calculated TTE is usually less than the TP date, the day on which the animal was euthanized for tumor size. Animals that did not reach the endpoint volume were assigned a TTE value equal to the last day of the study (D39). Any animal classified as having died from treatment-related (TR) causes was to be assigned a TTE value equal to the day of death. Any animal classified as having died from non-treatment-related (NTR) causes was to be excluded from TTE calculations.

Treatment efficacy was determined from tumor growth delay (TGD), which is defined as the increase in the median TTE, in days, for a treatment group compared to the control group:

$$TGD = T - C$$

The percent increase in the median TTE, relative to the control group, is
where:

$$\% \, TGD = \frac{T-C}{C} \times 100$$

T=median TTE for a treatment group, and
C=median TTE for the designated control group.

Treatment efficacy in each group may be indicated by the median tumor volume, MTV(n), which was defined as the median tumor volume on the last day of the study (D39) in the number of animals remaining (n) whose tumors had not attained the endpoint volume.

Treatment efficacy may also be determined from the incidence and magnitude of regression responses observed during the study. Treatment may cause partial regression (PR) or complete regression (CR) of the tumor in an animal. In a PR response, the tumor volume was 50% or less of its D1 volume for three consecutive measurements during the course of the study, and equal to or greater than 13.5 mm³ for one or more of these three measurements. In a CR response, the tumor volume was less than 13.5 mm³ for three consecutive measurements during the course of the study. Any animal with a CR response at the end of the study was additionally classified as a tumor-free survivor (TFS).

Animals were weighed daily for the first five days, then twice weekly for the remainder of the study. The mice were observed frequently for health and overt signs of any adverse treatment related TR side effects, and noteworthy clinical observations were recorded. Individual body weight loss was monitored per protocol, and any animal with weight loss exceeding 30% for one measurement, or exceeding 25% for three measurements, was to be euthanized for health as a TR death. If group mean body weight recovered, dosing may resume in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity is considered above the maximum tolerated dose (MTD). A death was to be classified as TR if it was attributable to treatment side effects as evidenced by clinical signs and/or necropsy, or may also be classified as TR if due to unknown causes during the dosing period or within 14 days of the last dose. A death was classified as NTR if there was evidence that the death was related to the tumor model, rather than treatment-related. NTR deaths are further categorized as NTRa (due to accident or human error), NTRm (due to necropsy-confirmed tumor dissemination by invasion or metastasis), and NTRu (due to unknown causes).

Prism 6.07 (GraphPad) for Windows was employed for graphical analyses. Statistics were not employed due to small sample size.

A scatter plot was constructed to show TTE values for individual mice, by group; this plot shows NTR deaths, which were excluded from all other figures. Individual animal, group median and mean tumor volumes were plotted as functions of time. When an animal exited the study because of tumor size or TR death, its final recorded tumor volume was included with the data used to calculate the median volume at subsequent time points. A Kaplan-Meier plot was constructed to show the percentage of animals in each group remaining on study versus time. Tumor growth curves were truncated after two TR deaths occurred in the same group. Group mean BW changes over the course of the study were graphed as percent change, ±SEM, from Day 1. Tumor growth and BW change curves were truncated after more than half the assessable mice in a group exited the study. FIG. 10 illustrates the mean tumor volume in the study.

Table 35 provides the mean BW losses, TR and NTR deaths for the mice. Clinical signs were recorded when observed, as shown in Tables 36-38. No TR deaths occurred during the study. Bodyweight losses were variable, severe for one animal in each group, and resulted from estrogen effects. Clinical observations including weight loss, enlarged uterine horns, and bladder crystals were present in both groups and were also attributable to estrogen effects. Estrogen toxicity resulted in two non-treatment related deaths in each group. The treatment evaluated in the study was acceptably tolerated.

TABLE 35

Response Summary

| Group | n | Treatment Regimen Agent | mg/kg | Route | Schedule | Median TTE | T-C | % TGD | MTV (n) D39 | Regressions PR | CR | TFS | Mean BW Nadir | Deaths TR | NTR |
|---|---|---|---|---|---|---|---|---|---|---|---|---|---|---|---|
| 1 | 2 | vehicle | — | ip | tid × 14 first Day 2 doses | 23.2 | — | — | — | 0 | 0 | 0 | −15.6% Day 25 | 0 | 2 |
| 2 | 2 | VHH13 | 1 | ip | tid × 14 first Day 2 doses | 32.9 | 9.7 | 42 | — | 0 | 0 | 0 | −21.9% Day 32 | 0 | 2 |

TABLE 36

Body Weight
Body Weight

| | Date | | | | | | | |
|---|---|---|---|---|---|---|---|---|
| | Jul. 27, 2015 | Jul. 28, 2015 | Jul. 29, 2015 | Jul. 30, 2015 | Jul. 31, 2015 | Aug. 3, 2015 | Aug. 6, 2015 | Aug. 10, 2015 |
| | Day of Study | | | | | | | |
| A# | 1 Wt (g) | 2 Wt (g) | 3 Wt (g) | 4 Wt (g) | 5 Wt (g) | 8 Wt (g) | 11 Wt (g) | 15 Wt (g) |
| Group 1: vehicle (ip, tid × 14 first Day 2 doses) | | | | | | | | |
| 1 | 27.50 | 28.60 | 28.10 | | 29.40 | NTRa on Aug. 1, 2015 | | |
| 2 | 26.30 | 27.30 | 27.40 | 29.30 | 27.40 | 26.80 | 26.40 | 26.50 |
| 3 | 30.10 | 31.00 | 30.50 | 27.30 | 31.10 | 29.50 | 28.20 | 26.00 |
| 4 | 23.00 | 24.20 | 24.40 | 30.00 | 25.00 | NTRu on Aug. 3, 2015 | | |
| Mean | 26.7 | 27.8 | 27.6 | 27.9 | 28.2 | 28.2 | 27.3 | 26.3 |
| STDEV | 2.9 | 2.8 | 2.5 | 2.2 | 2.6 | 1.9 | 1.3 | 0.4 |
| n | 4 | 4 | 4 | 4 | 4 | 2 | 2 | 2 |

TABLE 36-continued

Body Weight
Body Weight

Group 2: VHH13 (1 mg/kg, ip, tid × 14 first Day 2 doses)

| A# | | | | | | | | |
|---|---|---|---|---|---|---|---|---|
| 1 | 28.90 | 29.30 | 28.50 | 29.60 | 28.80 | 28.70 | 27.80 | 28.30 |
| 2 | 25.30 | 27.00 | 26.40 | 26.40 | 26.30 | 25.90 | 25.80 | 26.00 |
| 3 | 27.20 | 25.40 | 23.90 | | | | | NTRu on Jul. 30, 2015 |
| 4 | 27.60 | 27.50 | 27.10 | 27.30 | 27.20 | 26.90 | 26.10 | NTRu on Aug. 8, 2015 |
| Mean | 27.3 | 27.3 | 26.5 | 27.8 | 27.4 | 27.2 | 26.6 | 27.2 |
| STDEV | 1.5 | 1.6 | 1.9 | 1.7 | 1.3 | 1.4 | 1.1 | 1.6 |
| n | 4 | 4 | 4 | 3 | 3 | 3 | 3 | 2 |

Date

| | Aug. 13, 2015 | Aug. 17, 2015 | Aug. 20, 2015 | Aug. 24, 2015 | Aug. 27, 2015 | Aug. 31, 2015 | Sep. 3, 2015 |
|---|---|---|---|---|---|---|---|
| | | | | Day of Study | | | |
| | 18 | 22 | 25 | 29 | 32 | 36 | 39 |
| A# | Wt (g) | Wt (g) | Wt (g) | Wt (g) | Wt (g) | Wt (g) | Wt (g) |

Group 1: vehicle (ip, tid × 14 first Day 2 doses)

| A# | | | | | | | |
|---|---|---|---|---|---|---|---|
| 1 | | | | NTRa on Aug. 1, 2015 | | | |
| 2 | 26.60 | 27.20 | | TP on Aug. 17, 2015 | | | |
| 3 | 22.50 | 23.60 | 23.80 | TP on Aug. 20, 2015 | | | |
| 4 | | | | NTRu on Aug. 3, 2015 | | | |
| Mean | 24.6 | 25.4 | 23.8 | | | | |
| STDEV | 2.9 | 2.5 | | | | | |
| n | 2 | 2 | 1 | | | | |

Group 2: VHH13 (1 mg/kg, ip, tid × 14 first Day 2 doses)

| A# | | | | | | | |
|---|---|---|---|---|---|---|---|
| 1 | 28.20 | 28.80 | 29.00 | 28.90 | TP on Aug. 24, 2015 | | |
| 2 | 24.50 | 21.90 | 20.10 | 21.10 | 21.20 | 23.80 | 24.20 |
| 3 | | | | NTRu on Jul. 30, 2015 | | | |
| 4 | | | | NTRu on Aug. 8, 2015 | | | |
| Mean | 26.4 | 25.4 | 24.6 | 25 | 21.2 | 23.8 | 24.2 |
| STDEV | 2.6 | 4.9 | 6.3 | 5.5 | | | |
| n | 2 | 2 | 2 | 2 | 1 | 1 | 1 |

TABLE 37

Tumor Measurement
Caliper Measurement

Date

| | Jul. 27, 2015 | | Jul. 30, 2015 | | Aug. 3, 2015 | | Aug. 6, 2015 | | Aug. 10, 2015 | | Aug. 13, 2015 | |
|---|---|---|---|---|---|---|---|---|---|---|---|---|
| | | | | | | Day of Study | | | | | | |
| | 1 | | 4 | | 8 | | 11 | | 15 | | 18 | |
| A# | W (mm) | L (mm) | W (mm) | L (mm) | W (mm) | L (mm) | W (mm) | L (mm) | W (mm) | L (mm) | W (mm) | L (mm) |

Group 1: vehicle (ip, tid × 14 first Day 2 doses)

| | | | | | | | | | | | | |
|---|---|---|---|---|---|---|---|---|---|---|---|---|
| 1 | 6 | 6 | 7 | 8 | | | NTRa on Aug. 1, 2015 | | | | | |
| 2 | 5 | 9 | 7 | 9 | 8 | 12 | 9 | 13 | 10 | 13 | 10 | 13 |
| 3 | 6 | 7 | 7 | 10 | 9 | 10 | 10 | 12 | 11 | 12 | 11 | 12 |
| 4 | 6 | 8 | 7 | 11 | | | NTRu on Aug. 3, 2015 | | | | | |

Group 2: VHH13 (1 mg/kg, ip, tid × 14 first Day 2 doses)

| | | | | | | | | | | | | |
|---|---|---|---|---|---|---|---|---|---|---|---|---|
| 1 | 6 | 6 | 7 | 8 | 8 | 10 | 9 | 10 | 9 | 10 | 9 | 10 |
| 2 | 6 | 6 | 6 | 7 | 7 | 8 | 7 | 8 | 8 | 9 | 8 | 9 |
| 3 | 6 | 7 | | | | | | | | | | |
| 4 | 6 | 7 | 6 | 8 | 7 | 10 | 8 | 10 | | | | |

TABLE 37-continued

Tumor Measurement
Caliper Measurement

| | | | | | | | | | | | Date | | |
|---|---|---|---|---|---|---|---|---|---|---|---|---|---|
| | Aug. 17, 2015 | | Aug. 20, 2015 | | Aug. 24, 2015 | | Aug. 27, 2015 | | Aug. 31, 2015 | | Sep. 3, 2015 | | |
| | | | | | | | Day of Study | | | | | | |
| | 22 | | 25 | | 29 | | 32 | | 36 | | 39 | | |
| A# | W (mm) | L (mm) | W (mm) | L (mm) | W (mm) | L (mm) | W (mm) | L (mm) | W (mm) | L (mm) | W (mm) | L (mm) | |
| Group 1: vehicle (ip, tid × 14 first Day 2 doses) | | | | | | | | | | | | | |
| 1 | | | | | NTRa on Aug. 1, 2015 | | | | | | | | |
| 2 | 12 | 15 | | | | | TP on Aug. 17, 2015 | | | | | | |
| 3 | 11 | 13 | 12 | 14 | | | | | TP on Aug. 20, 2015 | | | | |
| 4 | | | | | NTRu on Aug. 3, 2015 | | | | | | | | |
| Group 2: VHH13 (1 mg/kg, ip, tid × 14 first Day 2 doses) | | | | | | | | | | | | | |
| 1 | 10 | 11 | 12 | 12 | 13 | 13 | | | TP on Aug. 24, 2015 | | | | |
| 2 | 9 | 10 | 9 | 10 | 10 | 10 | 10 | 10 | 12 | 12 | 13 | 13 | |
| 3 | | | | | NTRu on Jul. 30, 2015 | | | | | | | | |
| 4 | | | | | NTRu on Aug. 8, 2015 | | | | | | | | |

TABLE 38

Tumor Volume
Tumor Volume

| | | | | Date | | | |
|---|---|---|---|---|---|---|---|
| | Jul. 27, 2015 | Jul. 30, 2015 | Aug. 3, 2015 | Aug. 6, 2015 | Aug. 10, 2015 | Aug. 13, 2015 | Aug. 17, 2015 |
| | | | | Day of Study | | | |
| | | 14 | 8 | 11 | 15 | 18 | 22 |
| A# | TV (mm$^3$) | TV (mm$^3$) | TV (mm$^3$) | TV (mm$^3$) | TV (mm$^3$) | TV (mm$^3$) | TV (mm$^3$) |
| Group 1: vehicle (ip, tid × 14 first Day 2 doses) | | | | | | | |
| 1 | | 196 | 384 | 527 | NTRa on Aug. 1, 2015 | | 1080 |
| 2 | 108 | 221 | 384 | 527 | 650 | 650 | 1080 |
| 3 | 113 | 245 | 405 | 600 | 726 | 726 | 787 |
| 4 | 126 | 270 | | | NTRu on Aug. 3, 2015 | | |
| Mean | 122.6 | 232.8 | 394.5 | 563.3 | 688 | 688 | 933.3 |
| SEM | 8.1 | 15.8 | 10.5 | 36.8 | 38 | 38 | 146.8 |
| n | 4 | 4 | 2 | 2 | 2 | 2 | 2...1 |
| Group 2: VHH13 (1 mg/kg, ip, tid × 14 first Day 2 doses) | | | | | | | |
| 1 | 108 | 196 | 320 | 405 | 405 | 405 | 550 |
| 2 | 108 | 126 | 196 | 196 | 288 | 288 | 405 |
| 3 | 126 | | | | NTRu on Jul. 30, 2015 | | |
| 4 | 126 | 144 | 245 | 320 | NTRu on Aug. 8, 2015 | | |
| Mean | 117 | 155.3 | 253.7 | 307 | 346.5 | 346.5 | 477.5 |
| SEM | 5.2 | 21 | 36.1 | 60.7 | 58.5 | 58.5 | 72.5 |
| n | 4 | 3 | 3 | | | | |

| | | | Date | | |
|---|---|---|---|---|---|
| | Aug. 20, 2015 | Aug. 24, 2015 | Aug. 27, 2015 | Aug. 31, 2015 | Sep. 3, 2015 |
| | | | Day of Study | | |
| | 25 | 29 | 32 | 36 | 39 |
| A# | TV (mm$^3$) | TV (mm$^3$) | TV (mm$^3$) | TV (mm$^3$) | TV (mm$^3$) |
| Group 1: vehicle (ip, tid × 14 first Day 2 doses) | | | | | |
| 1 | | NTRa on Aug. 1, 2015 | | | |
| 2 | | TP on Aug. 17, 2015 | | | |
| 3 | 1008 | | TP on Aug. 20, 2015 | | |
| 4 | | NTRu on Aug. 3, 2015 | | | |
| Mean | 1008 | | | | |
| SEM | | | | | |
| n | | | | | |

TABLE 38-continued

Tumor Volume
Tumor Volume

Group 2: VHH13 (1 mg/kg, ip, tid × 14 first Day 2 doses)

| | | | | | |
|---|---|---|---|---|---|
| 1 | 864 | 1099 | TP on Aug. 24, 2015 | | |
| 2 | 405 | 500 | 500 | 864 | 1099 |
| 3 | | | NTRu on Jul. 30, 2015 | | |
| 4 | | | NTRu on Aug. 8, 2015 | | |
| Mean | 634.5 | 799.3 | 500 | 864 | 1098.5 |
| SEM | 229.5 | 299.3 | | | |
| n | 3 2 2 2 2 2 1 1 1 | | | | |

Table A1. MCF-7-e353 Clinical Observations

Because two out of the four mice in the control group and also in the treatment group died of estrogen toxicity, no statistical conclusion could be determined. With the data available, the median tumor growth and mean tumor volume were reduced in the treatment group when compared to the control group. This difference was present during the 14 days of treatment but also to day 25 of the study. It took the control group 25 days to reach a tumor volume of 1000 mm$^3$, whereas the treatment group took 36 days to reach a tumor volume of 1000 mm$^3$. This suggests that anti-STAT3 bacterial VHH13 (SEQ ID NO:3) sdAb slows the growth of MCF-7 tumor in vivo. Throughout the study both the control group and the treatment group maintained similar weights. This suggests that the anti-STAT3 bacterial VHH13 (SEQ ID NO:3) sdAb did not cause toxicity with respect to weight loss.

Example 13: Treatment of Human HER2+ (BT474) Breast Cancer with Anti-STAT3 Bacterial VHH13 (SEQ ID NO:3) SDAB in Xenograft Mice In this Example, the efficacy of anti-STAT3 bacterial VHH13 (SEQ ID NO:3) sdAb was determined in the BT474 human breast tumor xenograft in CB.17 SCID mice.

Two groups of 8-12 week old CB.17 SCID mice containing xenographs of 1 mm$^3$ BT474 tumor fragments in their flank were treated according to the protocol shown in Table 39 when the tumors reached an average size of 100-150 mm$^3$. All vehicle (PBS control) and anti-STAT3 bacterial VHH13 (SEQ ID NO:3) sdAb (shown in Table 39 as SB-01) doses were administered intraperitoneally (i.p.) three times daily, six hours apart for fourteen days, with two doses delivered on Day 1 (tid×14, first day 2 doses). The dosing volume for vehicle and anti-STAT3 bacterial VHH13 (SEQ ID NO:3) sdAb was 0.478 mL per 20 grams of body weight (23.88 mL/kg) and was scaled to the body weight of each individual animal. Group 1 received the vehicle and served as the benchmark group for tumor engraftment and progression, as well as the control. Group 2 was given anti-STAT3 bacterial VHH13 (SEQ ID NO:3) sdAb at 1 mg/kg.

TABLE 39

Study protocol

Regimen 1

| Gr. | N | Agent | Vehicle | mg/kg | Route | Schedule |
|---|---|---|---|---|---|---|
| 1# | 4 | vehicle | | — | ip | tid × 14 first day 2 doses |
| 2 | 4 | SB-01 | | 1 | ip | tid × 14 first day 2 doses |

During the first 14 days of the study, the treatment group received anti-STAT3 B VHH13 and the control group only received the vehicle. As shown in Table 40, during this time, the treatment group maintained and gained weight throughout the study while the control group had lower weights throughout the study. This suggests that the treatment group did not experience toxicity from anti-STAT3 bacterial VHH13 (SEQ ID NO:3) sdAb with respect to weight loss. Both groups mean tumor volume and median tumor volume were similar, and exactly the same on day 15 of the study. On day 59 of the study, both groups reached a tumor volume of 700 cubic mm$^3$. This suggests that the anti-STAT3 bacterial VHH13 (SEQ ID NO:3) sdAb did not reduce the growth of BT474 tumors in vivo when compared to the control group. FIG. 11 illustrates the group mean tumor volume.

TABLE 40

BT474 Response Summary

| | | | Treatment Regimen 1 | | | | | | | MTV | | | | | | | |
|---|---|---|---|---|---|---|---|---|---|---|---|---|---|---|---|---|---|
| Group | n | Agent | Vehicle | mg/kg | Route | Schedule | Median TTE | T-C | % TGD | Stat Sign | (n), Day 60 | PR | CR | TFS | BW Nadir | TR | NTRm | NTR |
| 1# | 4 | vehicle | | — | ip | tid × 14 first day 2 doses | 49.2 | — | — | | 288 (2) | 0 | 0 | 0 | −9.1% (3) | 0 | 0 | 0 |
| 2 | 4 | SB-01 | | 1 | ip | tid × 14 first day 2 doses | 60.0 | 10.8 | 22 | | 550 (3) | 0 | 0 | 0 | — | 0 | 0 | 0 |

Control Group

Example 14: Production of Mouse Monoclonal Antibody Directed Against Anti-STAT3 Bacterial VHH13 (SEQ ID NO:3) SDAB In this Example, mouse monoclonal antibodies were generated towards the sdAb of the invention. The animals used were BALB/c female mice, 8-10 week. A water-soluble adjuvant was used (CBL). The HAT and the HT used were from Sigma-Aldrich.

Anti-STAT3 bacterial VHH13 (SEQ ID NO:3) sdAb was used to immunize three mice and make hybridoma cell lines. The mice were immunized three times each with water-soluble adjuvant. In one mouse, the serum titer reached 1/51200. The mouse was sacrificed and hybridoma cell lines were made by fusing spleen cells with myeloma cell line Sp2/0.

The fused cells were seeded into 96 well plates by limited dilution. The fused cells were cultured in the presence of HAT, and 651 single clones were tested. Of the 651 single clones, 27 positive clones were identified that specifically bound to anti-STAT3 bacterial VHH13 (SEQ ID NO:3) sdAb antigen.

Example 15: Cytotoxicity of KRAS (G12D) Single Domain Antibodies on PANC-1 Human Pancreatic Cancer Cells This Example demonstrates the anti-proliferative effects of the anti-KRAS (G12D) (SEQ ID NO:2) sdAb using the human pancreatic cancer cell line PANC-1. For the experiments, the PANC-1 cells were grown until they reached a confluency of 90%. At that time, proliferation studies were carried out using the MTT assay as described above.

The anti-proliferative properties of anti-KRAS (G12D) (SEQ ID NO:2) sdAB on PANC-1 cells three days post treatment are shown in Table 41. PANC-1 cells treated with the anti-KRAS (G12D) (SEQ ID NO:2) sdAb showed an average growth inhibition of 19.9 and 37.7 at 50.0 and 100 µg/ml, respectively.

TABLE 41

Anti-proliferative Actions of Anti-KRAS (G12D) (SEQ ID NO: 2) sdAb on PANC-1 Cancer Cells

|  | Mean Abs ± SE | % Inhibition |
|---|---|---|
| control | 0.281 ± 0.017 |  |
| 50 µg/ml | 0.225 ± 0.006 | 19.9 |
| 100 µg/ml | 0.175 ± 0.016 | 37.7 |

Thus, the anti-KRAS (G12D) (SEQ ID NO:2) sdAb showed dose-dependent growth inhibition in the PANC-1 human pancreatic cancer cells.

Example 16: In Vitro Growth Inhibition by TNF-Alpha SDAB

This Example demonstrates the method development to determine TNF-alpha concentration and evaluation of the inhibition of TNF-alpha function. The concentration of TNF-alpha required to show measurable modulation of activity in the U937 human lung lymphoblast cell line was evaluated by quantitation of the ATP present, which signals the presence of metabolically active cells using Promega's Cell Titer-GJo® Luminescent Cell Viability assay.

The U937 cells were seeded in a clear polystyrene 96-well microculture plate (Corning® Costar® 96-well flat bottom plate, Cat. #3997) in a total volume of 90 µL/well. After 24 hours of incubation in a humidified incubator at 37° C. with 5% $CO_2$ and 95% air, 5 µL of 20×, serially diluted TNF-alpha in growth medium was added to each well in duplicate (10 pt dose response, highest concentration 20 ng/mL). Additionally, 5 µL of 20×, diluted staurosporine in growth medium was added to each well in duplicate (concentration 1 nM).

After 24 hours of culture in the presence of test agents, the concentration of compound required to show measurable modulation of TNF-alpha activity in the U937 cell line as evaluated by quantitation of the ATP present. Percent cell growth was calculated relative to untreated control wells. All tests were performed in duplicate at each concentration level.

The $EC_{50}$ value for the test agents was estimated using Prism 6.05 by curve-fitting the data using the following four parameter-logistic equation:

$$Y = \frac{\text{Top} - \text{Bottom}}{1 + \left(\frac{X}{IC_{50}}\right)^n} + \text{Bottom}$$

where Top is the maximal % of control absorbance, Bottom is the minimal % of control absorbance at the highest agent concentration, Y is the % of control absorbance, X is the agent concentration, $IC_{50}$ is the concentration of agent that inhibits cell growth by 50% compared to the control cells, and n is the slope of the curve.

FIGS. 12 and 13 demonstrate that TNF-alpha is cytotoxic to the U937 cells. The $IC_{50}$ for TNF-alpha against U937 is 95.10 pg/ml. The TNF-alpha curve shows a dose titration killing effect.

FIG. 14 demonstrates that TNF-alpha cytotoxicity against U937 is inhibited by the three different anti-TNF-alpha VHHs. When anti-TNF-alpha VHH62 (SEQ ID NO:47) sdAb, anti-TNF-alpha VHH 66 (SEQ ID NO:45) sdAb, and anti-TNF-alpha VHH69 (SEQ ID NO:46) sdAb were incubated with a constant dose of TNF-alpha, at $EC_{50}$, all three anti-TNF-alpha VHHs inhibit killing of U937 by TNF-alpha. The $IC_{50}$ of anti-TNF-alpha VHH62 (SEQ ID NO:47) sdAb was approximately 713.6 ug/ml. The $IC_{50}$ of anti-TNF-alpha VHH69 (SEQ ID NO:46) sdAb was greater than 208.055 ug/ml. The $IC_{50}$ of anti-TNF-alpha VHH66 (SEQ ID NO:45) sdAb could not be determined because it completely inhibited the cytotoxicity of TNF-alpha from concentrations of about $1 \times 10^2$ ug/ml to $1 \times 10^2$ ug/ml of anti-TNF-alpha VHH66 (SEQ ID NO:45) sdAb. In this concentration range of anti-TNF-alpha VHH66 (SEQ ID NO:45) sdAb, there is an increase in U937 cell growth, and thus complete inhibition of TNF-alpha activity.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. An anti-KRAS single domain antibody (sdAb), wherein the sdAb can passively cross a cellular membrane to target the intracellular component without exogenous compounds and without additional membrane targeting sequences, wherein the anti-KRAS sdAb comprises an anti-KRAS (G12D) sdAb comprising the amino acid sequence as set forth in SEQ ID NO:2.

2. A method of treating a disease that expresses KRAS, preventing development of a disease that expresses KRAS, or preventing recurrence of a disease that expresses KRAS in a subject using the anti-KRAS sdAb according to claim 1, the method comprising administering an effective amount of the anti-KRAS sdAb to a subject in need thereof.

3. The method of claim 2, wherein the subject is a mammal.

4. The method of claim 3, wherein the mammal is a human.

5. The method of claim 2, wherein the anti-KRAS sdAb is administered in combination with one or more compounds.

6. The method of claim 5, wherein the one or more compounds is a transcriptional inhibitor.

7. The method of claim 2, wherein administering an effective amount of the anti-KRAS sdAb to a subject in need thereof comprises intravenous administration, intramuscular administration, oral administration, rectal administration, enteral administration, parenteral administration, intraocular administration, subcutaneous administration, transdermal administration, administered as eye drops, administered as nasal spray, administered by inhalation or nebulization, topical administration, and administered as an implantable drug.

8. An isolated polypeptide, the isolated polypeptide comprising the amino acid sequence as set forth in SEQ ID NO:2.

9. A method of measuring the levels of an anti-KRAS sdAb in a sample from a subject, the method comprising the steps of:
   a) generating a mouse monoclonal antibody directed against the anti-KRAS sdAb according to claim 1;
   b) obtaining a sample from the subject;
   c) performing a quantitative immunoassay with the mouse monoclonal antibody and the sample to determine the amount of sdAb in a subject; and
   d) quantifying the amount of sdAb in the subject.

10. The method of claim 9 wherein the quantitative immunoassay comprises an enzyme-linked immunosorbent assay (ELISA), specific analyte labeling and recapture assay (SALRA), liquid chromatography, mass spectrometry, fluorescence-activated cell sorting, or a combination thereof.

* * * * *